(12) United States Patent
Balazs et al.

(10) Patent No.: US 8,497,071 B2
(45) Date of Patent: Jul. 30, 2013

(54) ISOLATION OF UNKNOWN REARRANGED T-CELL RECEPTORS FROM SINGLE CELLS

(75) Inventors: Alejandro Benjamin Balazs, Berkeley, CA (US); Jonathan Michael Tsai, Saratoga, CA (US); David Baltimore, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 397 days.

(21) Appl. No.: 12/824,744

(22) Filed: Jun. 28, 2010

(65) Prior Publication Data

US 2011/0014659 A1 Jan. 20, 2011

Related U.S. Application Data

(60) Provisional application No. 61/221,505, filed on Jun. 29, 2009.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
USPC ............................................... 435/6.12, 91.2
See application file for complete search history.

(56) References Cited

U.S. PATENT DOCUMENTS

| 5,840,304 | A | | 11/1998 | Davis et al. | |
|---|---|---|---|---|---|
| 6,087,096 | A | * | 7/2000 | Dau et al. | 435/6.16 |
| 6,114,516 | A | | 9/2000 | Hercend et al. | |
| 6,221,352 | B1 | * | 4/2001 | Howell et al. | 424/139.1 |
| 6,416,948 | B1 | * | 7/2002 | Pilarski et al. | 435/6.14 |
| 7,294,712 | B2 | | 11/2007 | Hercend et al. | |
| 2002/0110807 | A1 | | 8/2002 | Pilarski et al. | |
| 2007/0117134 | A1 | * | 5/2007 | Kou | 435/6 |

FOREIGN PATENT DOCUMENTS

WO   WO 2004/015070   2/2004

OTHER PUBLICATIONS

Roers et al., Eur. J. Immunol. 28, 2424-2431 (1998).*
Kneba et al., Blood 86(10), 3930-3937 (1995).*
Zhou et al., Laboratory Investigation 86, 314-321 (2006).*
International Search Report and Written Opinion dated Mar. 30, 2011 in Application No. PCT/US2010/040245, filed Jun. 28, 2010.

* cited by examiner

*Primary Examiner* — Kenneth Horlick
(74) *Attorney, Agent, or Firm* — Knobbe, Martens, Olson & Bear LLP

(57) ABSTRACT

Disclosed herein are methods and materials for isolating and identifying T cell receptors from single cells. In some embodiments, genomic DNA from a single T cell is isolated using whole genome amplification (WGA). A series of PCR reactions is carried out to enrich the genomic template for sequences encoding the TCR alpha and beta chains, and then to isolate the sequences encoding the TCR alpha and beta chains.

17 Claims, 8 Drawing Sheets

SEQUENCE LISTING

```
<160> NUMBER OF SEQ ID NOS: 511

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
cagaaccctg accctgccgt gtacc                                              25

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
gccattcctg aagcaaggaa acagcc                                             26

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
ggccacactg gtgtgcctgg cc                                                 22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
cggcgctgac gatctgggtg ac                                                 22

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
ccaatggctc aggaactggg aatgc                                              25

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
ggaaaaaatg caaaacaggt agtcttaaat aagcattc                                38
```

```
<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
gaccccccca atcccgccc                                                    19

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
cagacacagc aaaagagcct agaacctgg                                         29

<210> SEQ ID NO 9
<211> LENGTH: 34
<212> TYPE: DNA
<213> ORGANISM: Artificial Sequence
<220> FEATURE:
<223> OTHER INFORMATION: primer

<400> SEQUENCE: 9
gataatatag ctctcttggc tggagattgc aggt                                   34

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
taacacctat caaactaaac agaatggctt tttgg                                  35

<210> SEQ ID NO 11
<211> LENGTH: 39
<212> TYPE: DNA
<213> ORGANISM: Artificial Sequence
<220> FEATURE:
<223> OTHER INFORMATION: primer

<400> SEQUENCE: 11
aagaaacaaa caataaaagc tttgtttggc tacataatt                              39

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
aagacctggg ttccagccac tttcctact                                         29

<210> SEQ ID NO 13
<211> LENGTH: 34
<212> TYPE: DNA
<213> ORGANISM: Artificial Sequence
<220> FEATURE:
<223> OTHER INFORMATION: primer
```

<400> SEQUENCE: 13
ctcctagctc ctgaggctca ggacccctgg cttc                          34

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
acacctcttg gtcttggtct cttcagacac tt                            32

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
tgtccgctct gctcagggcc ct                                       22

<210> SEQ ID NO 16
<211> LENGTH: 32
<212> TYPE: DNA
<213> ORGANISM: Artificial Sequence
<220> FEATURE:
<223> OTHER INFORMATION: primer

<400> SEQUENCE: 16
ttttcctcac actaagaaga caagacccaa gg                            32

<210> SEQ ID NO 17
<211> LENGTH: 44
<212> TYPE: DNA
<213> ORGANISM: Artificial Sequence
<220> FEATURE:
<223> OTHER INFORMATION: primer

<400> SEQUENCE: 17
tagtgttaaa aaaaagaga agatgttgaa tacacaagtc aact                44

<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
atttcttttt ggattgaaaa ttttaatcct cagtgaac                      38

<210> SEQ ID NO 19
<211> LENGTH: 41
<212> TYPE: DNA
<213> ORGANISM: Artificial Sequence
<220> FEATURE:
<223> OTHER INFORMATION: primer

<400> SEQUENCE: 19
aaatatccat tctaggtgca ttttttaagg gtttaaaatt t                  41

-continued

```
<210> SEQ ID NO 20
<211> LENGTH: 40
<212> TYPE: DNA
<213> ORGANISM: Artificial Sequence
<220> FEATURE:
<223> OTHER INFORMATION: primer

<400> SEQUENCE: 20
acaacctgat gatagaagta actcttataa ctggaggttg                              40

<210> SEQ ID NO 21
<211> LENGTH: 32
<212> TYPE: DNA
<213> ORGANISM: Artificial Sequence
<220> FEATURE:
<223> OTHER INFORMATION: primer

<400> SEQUENCE: 21
cgatgatgga agtagctctt atggctggag at                                      32

<210> SEQ ID NO 22
<211> LENGTH: 38
<212> TYPE: DNA
<213> ORGANISM: Artificial Sequence
<220> FEATURE:
<223> OTHER INFORMATION: primer

<400> SEQUENCE: 22
cacctcacag tacagagtcc tgaaaataaa gaagaaga                                38

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23
ttcttcatgt taaggatcaa gaccattatt tgggtaa                                 37

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24
aaatgagaaa cgtttgttat tatttttttt tcgtgtttaa                              40

<210> SEQ ID NO 25
<211> LENGTH: 31
<212> TYPE: DNA
<213> ORGANISM: Artificial Sequence
<220> FEATURE:
<223> OTHER INFORMATION: primer

<400> SEQUENCE: 25
tgaggctcag cgcccttggc ttctgtccgc c                                       31

<210> SEQ ID NO 26
<211> LENGTH: 31
<212> TYPE: DNA
<213> ORGANISM: Artificial Sequence
<220> FEATURE:
<223> OTHER INFORMATION: primer
```

<400> SEQUENCE: 26
cagagtgtct atgtggctga atcgtttcca g                                                31

<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27
tcatctgtga ctgaggagcc ttgctcc                                                     27

<210> SEQ ID NO 28
<211> LENGTH: 32
<212> TYPE: DNA
<213> ORGANISM: Artificial Sequence
<220> FEATURE:
<223> OTHER INFORMATION: primer

<400> SEQUENCE: 28
acctttcggt ttggatatct ctcaacaaaa cc                                               32

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
agacggagca cggaacattt cactcag                                                     27

<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30
aagaaggttg gaattatcgt aatttgtttc taggctg                                          37

<210> SEQ ID NO 31
<211> LENGTH: 40
<212> TYPE: DNA
<213> ORGANISM: Artificial Sequence
<220> FEATURE:
<223> OTHER INFORMATION: primer

<400> SEQUENCE: 31
cttgtgagcc attctccata tttcagatat aagatttcag                                       40

<210> SEQ ID NO 32
<211> LENGTH: 39
<212> TYPE: DNA
<213> ORGANISM: Artificial Sequence
<220> FEATURE:
<223> OTHER INFORMATION: primer

<400> SEQUENCE: 32
ccaaggttta gttaaatata tcttatggtg aaaatgccc                                        39

```
<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
gttgggaaga ctggaagacc acctgg                                          26

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
ttccacagat tttggctgaa aacgttttt ct                                    32

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
gtaccaggca acccatttag gagaagttgg                                      30

<210> SEQ ID NO 36
<211> LENGTH: 34
<212> TYPE: DNA
<213> ORGANISM: Artificial Sequence
<220> FEATURE:
<223> OTHER INFORMATION: primer

<400> SEQUENCE: 36
aacctagaat cagacacaaa aactgaactc tggg                                 34

<210> SEQ ID NO 37
<211> LENGTH: 34
<212> TYPE: DNA
<213> ORGANISM: Artificial Sequence
<220> FEATURE:
<223> OTHER INFORMATION: primer

<400> SEQUENCE: 37
cccactcagg agatcttcta gaatagagct ctca                                 34

<210> SEQ ID NO 38
<211> LENGTH: 27
<212> TYPE: DNA
<213> ORGANISM: Artificial Sequence
<220> FEATURE:
<223> OTHER INFORMATION: primer

<400> SEQUENCE: 38
aggagcagct aaagtcaggg gccatgt                                         27

<210> SEQ ID NO 39
<211> LENGTH: 30
<212> TYPE: DNA
<213> ORGANISM: Artificial Sequence
<220> FEATURE:
<223> OTHER INFORMATION: primer
```

```
<400> SEQUENCE: 39
tgcagctttc taggcaggag acaagacaat                                    30

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
gttaaggaag cccattcaga agctgactgg                                    30

<210> SEQ ID NO 41
<211> LENGTH: 27
<212> TYPE: DNA
<213> ORGANISM: Artificial Sequence
<220> FEATURE:
<223> OTHER INFORMATION: primer

<400> SEQUENCE: 41
gacacagagt ctgagttctg gggcctg                                       27

<210> SEQ ID NO 42
<211> LENGTH: 29
<212> TYPE: DNA
<213> ORGANISM: Artificial Sequence
<220> FEATURE:
<223> OTHER INFORMATION: primer

<400> SEQUENCE: 42
gcaaagtaac ttctgctggg gaagctcat                                     29

<210> SEQ ID NO 43
<211> LENGTH: 34
<212> TYPE: DNA
<213> ORGANISM: Artificial Sequence
<220> FEATURE:
<223> OTHER INFORMATION: primer

<400> SEQUENCE: 43
gtgtcactct aagcccaaga gagtttcttg aagc                               34

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
ttaaaggtag tgaatcacgt tttgcccagg                                    30

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
aacccatcag agcaggagac ttttcactct                                    30
```

-continued

```
<210> SEQ ID NO 46
<211> LENGTH: 35
<212> TYPE: DNA
<213> ORGANISM: Artificial Sequence
<220> FEATURE:
<223> OTHER INFORMATION: primer

<400> SEQUENCE: 46
atactcaagg ttcagatcag aagaggaggc ttctc                          35

<210> SEQ ID NO 47
<211> LENGTH: 35
<212> TYPE: DNA
<213> ORGANISM: Artificial Sequence
<220> FEATURE:
<223> OTHER INFORMATION: primer

<400> SEQUENCE: 47
caactttcaa ggctcctaaa tctgagtttt cagtg                          35

<210> SEQ ID NO 48
<211> LENGTH: 31
<212> TYPE: DNA
<213> ORGANISM: Artificial Sequence
<220> FEATURE:
<223> OTHER INFORMATION: primer

<400> SEQUENCE: 48
aactgtgaat cctcacttca acagtgatgc c                              31

<210> SEQ ID NO 49
<211> LENGTH: 33
<212> TYPE: DNA
<213> ORGANISM: Artificial Sequence
<220> FEATURE:
<223> OTHER INFORMATION: primer

<400> SEQUENCE: 49
atatattccg aaatcctcca acagagacct gtg                            33

<210> SEQ ID NO 50
<211> LENGTH: 25
<212> TYPE: DNA
<213> ORGANISM: Artificial Sequence
<220> FEATURE:
<223> OTHER INFORMATION: primer

<400> SEQUENCE: 50
ggtcccaccg aggctttagt gagca                                     25

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
agagaaagga ttagtgacac tggcccatgg                                30

<210> SEQ ID NO 52
<211> LENGTH: 33
<212> TYPE: DNA
<213> ORGANISM: Artificial Sequence
<220> FEATURE:
<223> OTHER INFORMATION: primer
```

<400> SEQUENCE: 52
gcattttgga caaagaagaa atagttgtcc gtc                                33

<210> SEQ ID NO 53
<211> LENGTH: 36
<212> TYPE: DNA
<213> ORGANISM: Artificial Sequence
<220> FEATURE:
<223> OTHER INFORMATION: primer

<400> SEQUENCE: 53
ctgttttctc atagacaagt ggtcagttct ttttgc                             36

<210> SEQ ID NO 54
<211> LENGTH: 34
<212> TYPE: DNA
<213> ORGANISM: Artificial Sequence
<220> FEATURE:
<223> OTHER INFORMATION: primer

<400> SEQUENCE: 54
ttcatcatct aagaaagcag agtagggcct ttct                               34

<210> SEQ ID NO 55
<211> LENGTH: 43
<212> TYPE: DNA
<213> ORGANISM: Artificial Sequence
<220> FEATURE:
<223> OTHER INFORMATION: primer

<400> SEQUENCE: 55
tctcactact acagtatcct tccataatat aatctgtctg caa                     43

<210> SEQ ID NO 56
<211> LENGTH: 24
<212> TYPE: DNA
<213> ORGANISM: Artificial Sequence
<220> FEATURE:
<223> OTHER INFORMATION: primer

<400> SEQUENCE: 56
tctccagcac agggtagcga tggg                                          24

<210> SEQ ID NO 57
<211> LENGTH: 41
<212> TYPE: DNA
<213> ORGANISM: Artificial Sequence
<220> FEATURE:
<223> OTHER INFORMATION: primer

<400> SEQUENCE: 57
accagaataa ttatatccat atatgcccaa tattgaggat a                       41

<210> SEQ ID NO 58
<211> LENGTH: 37
<212> TYPE: DNA
<213> ORGANISM: Artificial Sequence
<220> FEATURE:
<223> OTHER INFORMATION: primer

<400> SEQUENCE: 58
cccctaaaaa gaaaaaaatc aatgaaaaca gatgttc                            37

```
<210> SEQ ID NO 59
<211> LENGTH: 36
<212> TYPE: DNA
<213> ORGANISM: Artificial Sequence
<220> FEATURE:
<223> OTHER INFORMATION: primer

<400> SEQUENCE: 59 cacctttttct tccacttatt gtcaccagaa tacatt                              36

<210> SEQ ID NO 60
<211> LENGTH: 34
<212> TYPE: DNA
<213> ORGANISM: Artificial Sequence
<220> FEATURE:
<223> OTHER INFORMATION: primer

<400> SEQUENCE: 60
caatacatat ggaagcctta aaccagataa gggg                                 34

<210> SEQ ID NO 61
<211> LENGTH: 34
<212> TYPE: DNA
<213> ORGANISM: Artificial Sequence
<220> FEATURE:
<223> OTHER INFORMATION: primer

<400> SEQUENCE: 61
tttcctgaga catgaagaca ttttaccctc aatc                                 34

<210> SEQ ID NO 62
<211> LENGTH: 33
<212> TYPE: DNA
<213> ORGANISM: Artificial Sequence
<220> FEATURE:
<223> OTHER INFORMATION: primer

<400> SEQUENCE: 62
caaatgttac ggtctgagag aagacaacac aag                                  33

<210> SEQ ID NO 63
<211> LENGTH: 36
<212> TYPE: DNA
<213> ORGANISM: Artificial Sequence
<220> FEATURE:
<223> OTHER INFORMATION: primer

<400> SEQUENCE: 63
agtaagttta gtgggtctca gtagccacat taagcc                               36

<210> SEQ ID NO 64
<211> LENGTH: 38
<212> TYPE: DNA
<213> ORGANISM: Artificial Sequence
<220> FEATURE:
<223> OTHER INFORMATION: primer

<400> SEQUENCE: 64
tcacctgtgc aatatatgac tacaggataa gtacaagc                             38

<210> SEQ ID NO 65
<211> LENGTH: 44
<212> TYPE: DNA
<213> ORGANISM: Artificial Sequence
<220> FEATURE:
<223> OTHER INFORMATION: primer

<400> SEQUENCE: 65
```
cttagatttc caaaaaagct tattacttgt ctcaaaaact aatc                44

<210> SEQ ID NO 66
<211> LENGTH: 29
<212> TYPE: DNA
<213> ORGANISM: Artificial Sequence
<220> FEATURE:
<223> OTHER INFORMATION: primer

<400> SEQUENCE: 66
gcacattgaa ttgcaaattg atgacaagg                                 29

<210> SEQ ID NO 67
<211> LENGTH: 40
<212> TYPE: DNA
<213> ORGANISM: Artificial Sequence
<220> FEATURE:
<223> OTHER INFORMATION: primer

<400> SEQUENCE: 67
gagttaattc atctcccctt ttaatttctc cacagtaata                     40

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
gaagaaactt tgctcccctg gccct                                     25

<210> SEQ ID NO 69
<211> LENGTH: 31
<212> TYPE: DNA
<213> ORGANISM: Artificial Sequence
<220> FEATURE:
<223> OTHER INFORMATION: primer

<400> SEQUENCE: 69
tgctgaaaaa cctacccacc attttgctta a                              31

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
aatacagact gaaaagaaga atttagcata atgtgttggt                     40

<210> SEQ ID NO 71
<211> LENGTH: 47
<212> TYPE: DNA
<213> ORGANISM: Artificial Sequence
<220> FEATURE:
<223> OTHER INFORMATION: primer

<400> SEQUENCE: 71
cccattaagt tacatgtaca gaatacattt gtagattagt aaatcag             47

<210> SEQ ID NO 72
<211> LENGTH: 32
<212> TYPE: DNA
<213> ORGANISM: Artificial Sequence

```
<220> FEATURE:
<223> OTHER INFORMATION: primer

<400> SEQUENCE: 72
ggtctaaatc agcccttaat ccacagacat tg                              32

<210> SEQ ID NO 73
<211> LENGTH: 27
<212> TYPE: DNA
<213> ORGANISM: Artificial Sequence
<220> FEATURE:
<223> OTHER INFORMATION: primer

<400> SEQUENCE: 73
gcatgcaggg catgccaaat actaagg                                    27

<210> SEQ ID NO 74
<211> LENGTH: 35
<212> TYPE: DNA
<213> ORGANISM: Artificial Sequence
<220> FEATURE:
<223> OTHER INFORMATION: primer

<400> SEQUENCE: 74
aaagagggca gtttttcctc ttggagataa tcata                           35

<210> SEQ ID NO 75
<211> LENGTH: 28
<212> TYPE: DNA
<213> ORGANISM: Artificial Sequence
<220> FEATURE:
<223> OTHER INFORMATION: primer

<400> SEQUENCE: 75
agcttctccc cacatcaagc actggact                                   28

<210> SEQ ID NO 76
<211> LENGTH: 31
<212> TYPE: DNA
<213> ORGANISM: Artificial Sequence
<220> FEATURE:
<223> OTHER INFORMATION: primer

<400> SEQUENCE: 76
ttcaaactaa tgatttgatt gattgcccct g                               31

<210> SEQ ID NO 77
<211> LENGTH: 29
<212> TYPE: DNA
<213> ORGANISM: Artificial Sequence
<220> FEATURE:
<223> OTHER INFORMATION: primer

<400> SEQUENCE: 77
agcttctgca tgatggaaga caggcttct                                  29

<210> SEQ ID NO 78
<211> LENGTH: 31
<212> TYPE: DNA
<213> ORGANISM: Artificial Sequence
<220> FEATURE:
<223> OTHER INFORMATION: primer

<400> SEQUENCE: 78
aaataattca agggaagaag ccattgctga g                               31
```

```
<210> SEQ ID NO 79
<211> LENGTH: 32
<212> TYPE: DNA
<213> ORGANISM: Artificial Sequence
<220> FEATURE:
<223> OTHER INFORMATION: primer

<400> SEQUENCE: 79
cactctcagc agtttgaact cagtgggagt ta                            32

<210> SEQ ID NO 80
<211> LENGTH: 35
<212> TYPE: DNA
<213> ORGANISM: Artificial Sequence
<220> FEATURE:
<223> OTHER INFORMATION: primer

<400> SEQUENCE: 80
aaatctccac taacttcacg ggatttattt gtttg                         35

<210> SEQ ID NO 81
<211> LENGTH: 27
<212> TYPE: DNA
<213> ORGANISM: Artificial Sequence
<220> FEATURE:
<223> OTHER INFORMATION: primer

<400> SEQUENCE: 81
cgcttcctac ttgccatgga cacagaa                                  27

<210> SEQ ID NO 82
<211> LENGTH: 36
<212> TYPE: DNA
<213> ORGANISM: Artificial Sequence
<220> FEATURE:
<223> OTHER INFORMATION: primer

<400> SEQUENCE: 82
tgctacactt tgtgcattat tcaactagtg tctcct                        36

<210> SEQ ID NO 83
<211> LENGTH: 42
<212> TYPE: DNA
<213> ORGANISM: Artificial Sequence
<220> FEATURE:
<223> OTHER INFORMATION: primer

<400> SEQUENCE: 83
ttcatttaaa aaaaaagaa aaagaaaaag aaaacaccttt tt                  42

<210> SEQ ID NO 84
<211> LENGTH: 41
<212> TYPE: DNA
<213> ORGANISM: Artificial Sequence
<220> FEATURE:
<223> OTHER INFORMATION: primer

<400> SEQUENCE: 84
cataagaaga actgttctat atgatttacg gacataacag c                  41

<210> SEQ ID NO 85
<211> LENGTH: 36
<212> TYPE: DNA
<213> ORGANISM: Artificial Sequence
<220> FEATURE:
<223> OTHER INFORMATION: primer

<400> SEQUENCE: 85
```
gtgtctggga tgtgagaact tgtcattaca gactaa                          36

<210> SEQ ID NO 86
<211> LENGTH: 40
<212> TYPE: DNA
<213> ORGANISM: Artificial Sequence
<220> FEATURE:
<223> OTHER INFORMATION: primer

<400> SEQUENCE: 86
gacagagaag attaaacaaa aaatgaacag agtggataac                      40

<210> SEQ ID NO 87
<211> LENGTH: 33
<212> TYPE: DNA
<213> ORGANISM: Artificial Sequence
<220> FEATURE:
<223> OTHER INFORMATION: primer

<400> SEQUENCE: 87
ggcagtttct gagatatttc aaactgcaca gac                             33

<210> SEQ ID NO 88
<211> LENGTH: 32
<212> TYPE: DNA
<213> ORGANISM: Artificial Sequence
<220> FEATURE:
<223> OTHER INFORMATION: primer

<400> SEQUENCE: 88
tcagtgctac ggcttccttt tgaaattaga gc                              32

<210> SEQ ID NO 89
<211> LENGTH: 32
<212> TYPE: DNA
<213> ORGANISM: Artificial Sequence
<220> FEATURE:
<223> OTHER INFORMATION: primer

<400> SEQUENCE: 89
gtccctcaaa catgaacacc aacaaccttt aa                              32

<210> SEQ ID NO 90
<211> LENGTH: 29
<212> TYPE: DNA
<213> ORGANISM: Artificial Sequence
<220> FEATURE:
<223> OTHER INFORMATION: primer

<400> SEQUENCE: 90
caacaggtcc cattggattt ctttccaga                                  29

<210> SEQ ID NO 91
<211> LENGTH: 34
<212> TYPE: DNA
<213> ORGANISM: Artificial Sequence
<220> FEATURE:
<223> OTHER INFORMATION: primer

<400> SEQUENCE: 91
attctgttgc ccagagtgac aaagtactga tgat                            34

<210> SEQ ID NO 92
<211> LENGTH: 26
<212> TYPE: DNA
<213> ORGANISM: Artificial Sequence

```
<220> FEATURE:
<223> OTHER INFORMATION: primer

<400> SEQUENCE: 92
cagcaccatt gctcactcag gtcagc                                          26

<210> SEQ ID NO 93
<211> LENGTH: 32
<212> TYPE: DNA
<213> ORGANISM: Artificial Sequence
<220> FEATURE:
<223> OTHER INFORMATION: primer

<400> SEQUENCE: 93
tgcagtatcc cctgttttaa aggaacacac ag                                   32

<210> SEQ ID NO 94
<211> LENGTH: 29
<212> TYPE: DNA
<213> ORGANISM: Artificial Sequence
<220> FEATURE:
<223> OTHER INFORMATION: primer

<400> SEQUENCE: 94
ggtttagaaa tgtccccatg aggactgca                                       29

<210> SEQ ID NO 95
<211> LENGTH: 37
<212> TYPE: DNA
<213> ORGANISM: Artificial Sequence
<220> FEATURE:
<223> OTHER INFORMATION: primer

<400> SEQUENCE: 95
ctcaaatgtc aggctagaac aaataatagg aaaaggc                              37

<210> SEQ ID NO 96
<211> LENGTH: 37
<212> TYPE: DNA
<213> ORGANISM: Artificial Sequence
<220> FEATURE:
<223> OTHER INFORMATION: primer

<400> SEQUENCE: 96
agccagaaaa agtttattta atatgcaatg aaaccca                              37

<210> SEQ ID NO 97
<211> LENGTH: 34
<212> TYPE: DNA
<213> ORGANISM: Artificial Sequence
<220> FEATURE:
<223> OTHER INFORMATION: primer

<400> SEQUENCE: 97
atgtctacta tgatccccag aatcttatgc aggc                                 34

<210> SEQ ID NO 98
<211> LENGTH: 33
<212> TYPE: DNA
<213> ORGANISM: Artificial Sequence
<220> FEATURE:
<223> OTHER INFORMATION: primer

<400> SEQUENCE: 98
ctctttctgc agtttaaagg gtttgctcaa cac                                  33
```

```
<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
ctaatgtatg agactgttag ccccagcgca                                       30

<210> SEQ ID NO 100
<211> LENGTH: 28
<212> TYPE: DNA
<213> ORGANISM: Artificial Sequence
<220> FEATURE:
<223> OTHER INFORMATION: primer

<400> SEQUENCE: 100
cggggaaggg agcaaaagta cataagga                                         28

<210> SEQ ID NO 101
<211> LENGTH: 29
<212> TYPE: DNA
<213> ORGANISM: Artificial Sequence
<220> FEATURE:
<223> OTHER INFORMATION: primer

<400> SEQUENCE: 101
ctgacactgg ggtgacattc cagaatttc                                        29

<210> SEQ ID NO 102
<211> LENGTH: 35
<212> TYPE: DNA
<213> ORGANISM: Artificial Sequence
<220> FEATURE:
<223> OTHER INFORMATION: primer

<400> SEQUENCE: 102
ggaggggcaa gtaattaaat cagaagtgtt tgaat                                 35

<210> SEQ ID NO 103
<211> LENGTH: 26
<212> TYPE: DNA
<213> ORGANISM: Artificial Sequence
<220> FEATURE:
<223> OTHER INFORMATION: primer

<400> SEQUENCE: 103
ccacaggacc agatgcctga gctagg                                           26

<210> SEQ ID NO 104
<211> LENGTH: 25
<212> TYPE: DNA
<213> ORGANISM: Artificial Sequence
<220> FEATURE:
<223> OTHER INFORMATION: primer

<400> SEQUENCE: 104
cactgcagac cagaatcctg ccctg                                            25

<210> SEQ ID NO 105
<211> LENGTH: 22
<212> TYPE: DNA
<213> ORGANISM: Artificial Sequence
<220> FEATURE:
<223> OTHER INFORMATION: primer

<400> SEQUENCE: 105
```
cagcacctcg cccaaaggac cc                                           22

<210> SEQ ID NO 106
<211> LENGTH: 24
<212> TYPE: DNA
<213> ORGANISM: Artificial Sequence
<220> FEATURE:
<223> OTHER INFORMATION: primer

<400> SEQUENCE: 106
ggaggaccaa gccctgagca caga                                         24

<210> SEQ ID NO 107
<211> LENGTH: 28
<212> TYPE: DNA
<213> ORGANISM: Artificial Sequence
<220> FEATURE:
<223> OTHER INFORMATION: primer

<400> SEQUENCE: 107
tatcaccgat gcacagaccc agaagacc                                     28

<210> SEQ ID NO 108
<211> LENGTH: 34
<212> TYPE: DNA
<213> ORGANISM: Artificial Sequence
<220> FEATURE:
<223> OTHER INFORMATION: primer

<400> SEQUENCE: 108
tcctactcac agtgactctg atctggtaaa gctc                              34

<210> SEQ ID NO 109
<211> LENGTH: 25
<212> TYPE: DNA
<213> ORGANISM: Artificial Sequence
<220> FEATURE:
<223> OTHER INFORMATION: primer

<400> SEQUENCE: 109
tcacccagag gaccccagtc agagg                                        25

<210> SEQ ID NO 110
<211> LENGTH: 26
<212> TYPE: DNA
<213> ORGANISM: Artificial Sequence
<220> FEATURE:
<223> OTHER INFORMATION: primer

<400> SEQUENCE: 110
tcccttttca ccaatgcaca gaccca                                       26

<210> SEQ ID NO 111
<211> LENGTH: 26
<212> TYPE: DNA
<213> ORGANISM: Artificial Sequence
<220> FEATURE:
<223> OTHER INFORMATION: primer

<400> SEQUENCE: 111
acctcaccca gaggacccca gtcaga                                       26

<210> SEQ ID NO 112
<211> LENGTH: 27
<212> TYPE: DNA
<213> ORGANISM: Artificial Sequence

```
<220> FEATURE:
<223> OTHER INFORMATION: primer

<400> SEQUENCE: 112 cctttcacc aatgcacaga cccagag                                              27

<210> SEQ ID NO 113
<211> LENGTH: 31
<212> TYPE: DNA
<213> ORGANISM: Artificial Sequence
<220> FEATURE:
<223> OTHER INFORMATION: primer

<400> SEQUENCE: 113
ctcacagtga tcctgatctg gtaaagctcc c                                        31

<210> SEQ ID NO 114
<211> LENGTH: 29
<212> TYPE: DNA
<213> ORGANISM: Artificial Sequence
<220> FEATURE:
<223> OTHER INFORMATION: primer

<400> SEQUENCE: 114
gcctttcatc aacacacaga cccagaaga                                           29

<210> SEQ ID NO 115
<211> LENGTH: 28
<212> TYPE: DNA
<213> ORGANISM: Artificial Sequence
<220> FEATURE:
<223> OTHER INFORMATION: primer

<400> SEQUENCE: 115
tcctgctcac agtgaccctg atctggta                                            28

<210> SEQ ID NO 116
<211> LENGTH: 24
<212> TYPE: DNA
<213> ORGANISM: Artificial Sequence
<220> FEATURE:
<223> OTHER INFORMATION: primer

<400> SEQUENCE: 116
cccaggagga ccaagccctg aatc                                                24

<210> SEQ ID NO 117
<211> LENGTH: 35
<212> TYPE: DNA
<213> ORGANISM: Artificial Sequence
<220> FEATURE:
<223> OTHER INFORMATION: primer

<400> SEQUENCE: 117
ggagcttagg aacttcagaa tgcttactac agaga                                    35

<210> SEQ ID NO 118
<211> LENGTH: 24
<212> TYPE: DNA
<213> ORGANISM: Artificial Sequence
<220> FEATURE:
<223> OTHER INFORMATION: primer

<400> SEQUENCE: 118
cttcagtctg cccacagcag ggct                                                24
```

```
<210> SEQ ID NO 119
<211> LENGTH: 28
<212> TYPE: DNA
<213> ORGANISM: Artificial Sequence
<220> FEATURE:
<223> OTHER INFORMATION: primer

<400> SEQUENCE: 119
ctcctctgct cctgttcaca aggaccct                                        28

<210> SEQ ID NO 120
<211> LENGTH: 22
<212> TYPE: DNA
<213> ORGANISM: Artificial Sequence
<220> FEATURE:
<223> OTHER INFORMATION: primer

<400> SEQUENCE: 120
aatttgccca cagcagggct gg                                              22

<210> SEQ ID NO 121
<211> LENGTH: 26
<212> TYPE: DNA
<213> ORGANISM: Artificial Sequence
<220> FEATURE:
<223> OTHER INFORMATION: primer

<400> SEQUENCE: 121
ttttgctcac agtgaccctg attggg                                          26

<210> SEQ ID NO 122
<211> LENGTH: 28
<212> TYPE: DNA
<213> ORGANISM: Artificial Sequence
<220> FEATURE:
<223> OTHER INFORMATION: primer

<400> SEQUENCE: 122
ctgctcccct ttcatcaatg cacagata                                        28

<210> SEQ ID NO 123
<211> LENGTH: 30
<212> TYPE: DNA
<213> ORGANISM: Artificial Sequence
<220> FEATURE:
<223> OTHER INFORMATION: primer

<400> SEQUENCE: 123
gctcctgctc atagtgacac tgacctggta                                      30

<210> SEQ ID NO 124
<211> LENGTH: 24
<212> TYPE: DNA
<213> ORGANISM: Artificial Sequence
<220> FEATURE:
<223> OTHER INFORMATION: primer

<400> SEQUENCE: 124
ccccaggagg accaagccct gaat                                            24

<210> SEQ ID NO 125
<211> LENGTH: 31
<212> TYPE: DNA
<213> ORGANISM: Artificial Sequence
<220> FEATURE:
<223> OTHER INFORMATION: primer

<400> SEQUENCE: 125
```
cctttcatca atgcacagat acagaagacc c						31

<210> SEQ ID NO 126
<211> LENGTH: 30
<212> TYPE: DNA
<213> ORGANISM: Artificial Sequence
<220> FEATURE:
<223> OTHER INFORMATION: primer

<400> SEQUENCE: 126
gctcctgctc acagtgacac tgatctggta						30

<210> SEQ ID NO 127
<211> LENGTH: 24
<212> TYPE: DNA
<213> ORGANISM: Artificial Sequence
<220> FEATURE:
<223> OTHER INFORMATION: primer

<400> SEQUENCE: 127
cccaggagga ccaagccctg aatc						24

<210> SEQ ID NO 128
<211> LENGTH: 26
<212> TYPE: DNA
<213> ORGANISM: Artificial Sequence
<220> FEATURE:
<223> OTHER INFORMATION: primer

<400> SEQUENCE: 128
cccctttcat caatgcacag acccag						26

<210> SEQ ID NO 129
<211> LENGTH: 28
<212> TYPE: DNA
<213> ORGANISM: Artificial Sequence
<220> FEATURE:
<223> OTHER INFORMATION: primer

<400> SEQUENCE: 129
tgctgctgct cacagtgaca ctgatctg						28

<210> SEQ ID NO 130
<211> LENGTH: 24
<212> TYPE: DNA
<213> ORGANISM: Artificial Sequence
<220> FEATURE:
<223> OTHER INFORMATION: primer

<400> SEQUENCE: 130
ttccccagga gaaccaagcc ctga						24

<210> SEQ ID NO 131
<211> LENGTH: 30
<212> TYPE: DNA
<213> ORGANISM: Artificial Sequence
<220> FEATURE:
<223> OTHER INFORMATION: primer

<400> SEQUENCE: 131 ccctttatc aatgcacaga cccagaagac						30

<210> SEQ ID NO 132
<211> LENGTH: 27
<212> TYPE: DNA
<213> ORGANISM: Artificial Sequence

```
<220> FEATURE:
<223> OTHER INFORMATION: primer

<400> SEQUENCE: 132
tccgctcctg ctcacagtga cactgat                                27

<210> SEQ ID NO 133
<211> LENGTH: 23
<212> TYPE: DNA
<213> ORGANISM: Artificial Sequence
<220> FEATURE:
<223> OTHER INFORMATION: primer

<400> SEQUENCE: 133
tttcccagga ggaccaagcc ctg                                    23

<210> SEQ ID NO 134
<211> LENGTH: 29
<212> TYPE: DNA
<213> ORGANISM: Artificial Sequence
<220> FEATURE:
<223> OTHER INFORMATION: primer

<400> SEQUENCE: 134
cctttcatca atgcacagac ccagaagac                              29

<210> SEQ ID NO 135
<211> LENGTH: 33
<212> TYPE: DNA
<213> ORGANISM: Artificial Sequence
<220> FEATURE:
<223> OTHER INFORMATION: primer

<400> SEQUENCE: 135
ttctgttcac agtgacactg atctggtaaa gcc                         33

<210> SEQ ID NO 136
<211> LENGTH: 26
<212> TYPE: DNA
<213> ORGANISM: Artificial Sequence
<220> FEATURE:
<223> OTHER INFORMATION: primer

<400> SEQUENCE: 136
ccaggaagac caagccctga atcagg                                 26

<210> SEQ ID NO 137
<211> LENGTH: 30
<212> TYPE: DNA
<213> ORGANISM: Artificial Sequence
<220> FEATURE:
<223> OTHER INFORMATION: primer

<400> SEQUENCE: 137
ctgctcacag tgaccctgat ctggtaaagc                             30

<210> SEQ ID NO 138
<211> LENGTH: 25
<212> TYPE: DNA
<213> ORGANISM: Artificial Sequence
<220> FEATURE:
<223> OTHER INFORMATION: primer

<400> SEQUENCE: 138
caaaagccct gctttctcac cccag                                  25
```

```
<210> SEQ ID NO 139
<211> LENGTH: 23
<212> TYPE: DNA
<213> ORGANISM: Artificial Sequence
<220> FEATURE:
<223> OTHER INFORMATION: primer

<400> SEQUENCE: 139
ctatttcccc aggcagggct ggg                                           23

<210> SEQ ID NO 140
<211> LENGTH: 27
<212> TYPE: DNA
<213> ORGANISM: Artificial Sequence
<220> FEATURE:
<223> OTHER INFORMATION: primer

<400> SEQUENCE: 140
ctgctcctgc tcacagtgac cctgatc                                       27

<210> SEQ ID NO 141
<211> LENGTH: 30
<212> TYPE: DNA
<213> ORGANISM: Artificial Sequence
<220> FEATURE:
<223> OTHER INFORMATION: primer

<400> SEQUENCE: 141
ctcacagagg gcctggtcta gaatattcca                                    30

<210> SEQ ID NO 142
<211> LENGTH: 28
<212> TYPE: DNA
<213> ORGANISM: Artificial Sequence
<220> FEATURE:
<223> OTHER INFORMATION: primer

<400> SEQUENCE: 142
ttctttgctc atgttcacag agggcctg                                      28

<210> SEQ ID NO 143
<211> LENGTH: 22
<212> TYPE: DNA
<213> ORGANISM: Artificial Sequence
<220> FEATURE:
<223> OTHER INFORMATION: primer

<400> SEQUENCE: 143
ttcgtgccca caagggcctc at                                            22

<210> SEQ ID NO 144
<211> LENGTH: 34
<212> TYPE: DNA
<213> ORGANISM: Artificial Sequence
<220> FEATURE:
<223> OTHER INFORMATION: primer

<400> SEQUENCE: 144
ctcatacttg taagctcctt catctggaaa tgtg                               34

<210> SEQ ID NO 145
<211> LENGTH: 30
<212> TYPE: DNA
<213> ORGANISM: Artificial Sequence
<220> FEATURE:
<223> OTHER INFORMATION: primer

<400> SEQUENCE: 145
```
cagagcctga gacagacaga tgcttcattc 30

<210> SEQ ID NO 146
<211> LENGTH: 26
<212> TYPE: DNA
<213> ORGANISM: Artificial Sequence
<220> FEATURE:
<223> OTHER INFORMATION: primer

<400> SEQUENCE: 146
tactgcacat cagaacccat cgctgg 26

<210> SEQ ID NO 147
<211> LENGTH: 22
<212> TYPE: DNA
<213> ORGANISM: Artificial Sequence
<220> FEATURE:
<223> OTHER INFORMATION: primer

<400> SEQUENCE: 147
tgcagcaagt gcctttgccc tg 22

<210> SEQ ID NO 148
<211> LENGTH: 29
<212> TYPE: DNA
<213> ORGANISM: Artificial Sequence
<220> FEATURE:
<223> OTHER INFORMATION: primer

<400> SEQUENCE: 148
cattctcttc caacaagtgc ttggagctc 29

<210> SEQ ID NO 149
<211> LENGTH: 25
<212> TYPE: DNA
<213> ORGANISM: Artificial Sequence
<220> FEATURE:
<223> OTHER INFORMATION: primer

<400> SEQUENCE: 149
gaggcagtgg tcacaactct cccca 25

<210> SEQ ID NO 150
<211> LENGTH: 35
<212> TYPE: DNA
<213> ORGANISM: Artificial Sequence
<220> FEATURE:
<223> OTHER INFORMATION: primer

<400> SEQUENCE: 150
tctctctctc ttagagcctg tgtctgtaac ttcag 35

<210> SEQ ID NO 151
<211> LENGTH: 27
<212> TYPE: DNA
<213> ORGANISM: Artificial Sequence
<220> FEATURE:
<223> OTHER INFORMATION: primer

<400> SEQUENCE: 151
cagaaagggg atgaaaaagc ctcatcc 27

<210> SEQ ID NO 152
<211> LENGTH: 25
<212> TYPE: DNA
<213> ORGANISM: Artificial Sequence

```
<220> FEATURE:
<223> OTHER INFORMATION: primer

<400> SEQUENCE: 152
atgccctgct tccctcaaca tccag                                        25

<210> SEQ ID NO 153
<211> LENGTH: 24
<212> TYPE: DNA
<213> ORGANISM: Artificial Sequence
<220> FEATURE:
<223> OTHER INFORMATION: primer

<400> SEQUENCE: 153
cccatcctgc ttccccacta ctgg                                         24

<210> SEQ ID NO 154
<211> LENGTH: 31
<212> TYPE: DNA
<213> ORGANISM: Artificial Sequence
<220> FEATURE:
<223> OTHER INFORMATION: primer

<400> SEQUENCE: 154
atcagggact aaattcatca cagcaccaag c                                 31

<210> SEQ ID NO 155
<211> LENGTH: 24
<212> TYPE: DNA
<213> ORGANISM: Artificial Sequence
<220> FEATURE:
<223> OTHER INFORMATION: primer

<400> SEQUENCE: 155
acagaaacca cctggagccc ccag                                         24

<210> SEQ ID NO 156
<211> LENGTH: 24
<212> TYPE: DNA
<213> ORGANISM: Artificial Sequence
<220> FEATURE:
<223> OTHER INFORMATION: primer

<400> SEQUENCE: 156
tggacccact tttccctgtg acgg                                         24

<210> SEQ ID NO 157
<211> LENGTH: 28
<212> TYPE: DNA
<213> ORGANISM: Artificial Sequence
<220> FEATURE:
<223> OTHER INFORMATION: primer

<400> SEQUENCE: 157
catttcccag gacagagtcc tccctcat                                     28

<210> SEQ ID NO 158
<211> LENGTH: 25
<212> TYPE: DNA
<213> ORGANISM: Artificial Sequence
<220> FEATURE:
<223> OTHER INFORMATION: primer

<400> SEQUENCE: 158
ctggattcca gccccttttt gcaag                                        25
```

```
<210> SEQ ID NO 159
<211> LENGTH: 28
<212> TYPE: DNA
<213> ORGANISM: Artificial Sequence
<220> FEATURE:
<223> OTHER INFORMATION: primer

<400> SEQUENCE: 159
ggtcctcctg gaactccgac cttatgat                                    28

<210> SEQ ID NO 160
<211> LENGTH: 29
<212> TYPE: DNA
<213> ORGANISM: Artificial Sequence
<220> FEATURE:
<223> OTHER INFORMATION: primer

<400> SEQUENCE: 160
aagcagagaa ctctgccttc aagggacaa                                   29

<210> SEQ ID NO 161
<211> LENGTH: 27
<212> TYPE: DNA
<213> ORGANISM: Artificial Sequence
<220> FEATURE:
<223> OTHER INFORMATION: primer

<400> SEQUENCE: 161
aactgatcat tgcagtcaaa cccaggc                                     27

<210> SEQ ID NO 162
<211> LENGTH: 21
<212> TYPE: DNA
<213> ORGANISM: Artificial Sequence
<220> FEATURE:
<223> OTHER INFORMATION: primer

<400> SEQUENCE: 162
cgtgcaggct gggctgctca c                                           21

<210> SEQ ID NO 163
<211> LENGTH: 19
<212> TYPE: DNA
<213> ORGANISM: Artificial Sequence
<220> FEATURE:
<223> OTHER INFORMATION: primer

<400> SEQUENCE: 163
gcccatcccg ccctctcgg                                              19

<210> SEQ ID NO 164
<211> LENGTH: 24
<212> TYPE: DNA
<213> ORGANISM: Artificial Sequence
<220> FEATURE:
<223> OTHER INFORMATION: primer

<400> SEQUENCE: 164
cagactcagc tcgggtcctt ccca                                        24

<210> SEQ ID NO 165
<211> LENGTH: 18
<212> TYPE: DNA
<213> ORGANISM: Artificial Sequence
<220> FEATURE:
<223> OTHER INFORMATION: primer

<400> SEQUENCE: 165
```

```
gggcgccccc tccccagt                                                      18

<210> SEQ ID NO 166
<211> LENGTH: 24
<212> TYPE: DNA
<213> ORGANISM: Artificial Sequence
<220> FEATURE:
<223> OTHER INFORMATION: primer

<400> SEQUENCE: 166
gcacaaaaac ccgagcgcag tctc                                               24

<210> SEQ ID NO 167
<211> LENGTH: 22
<212> TYPE: DNA
<213> ORGANISM: Artificial Sequence
<220> FEATURE:
<223> OTHER INFORMATION: primer

<400> SEQUENCE: 167
caaaaaccag acccaagccg cc                                                 22

<210> SEQ ID NO 168
<211> LENGTH: 21
<212> TYPE: DNA
<213> ORGANISM: Artificial Sequence
<220> FEATURE:
<223> OTHER INFORMATION: primer

<400> SEQUENCE: 168
cgccgccttc cacctgaatc c                                                  21

<210> SEQ ID NO 169
<211> LENGTH: 19
<212> TYPE: DNA
<213> ORGANISM: Artificial Sequence
<220> FEATURE:
<223> OTHER INFORMATION: primer

<400> SEQUENCE: 169
cgactccggg gaccgaggg                                                     19

<210> SEQ ID NO 170
<211> LENGTH: 29
<212> TYPE: DNA
<213> ORGANISM: Artificial Sequence
<220> FEATURE:
<223> OTHER INFORMATION: primer

<400> SEQUENCE: 170
ggacaaaaca ttgaccagcc cactgagat                                          29

<210> SEQ ID NO 171
<211> LENGTH: 30
<212> TYPE: DNA
<213> ORGANISM: Artificial Sequence
<220> FEATURE:
<223> OTHER INFORMATION: primer

<400> SEQUENCE: 171
aaggaccaag tgtttcagcc ttccacagtg                                         30

<210> SEQ ID NO 172
<211> LENGTH: 25
<212> TYPE: DNA
<213> ORGANISM: Artificial Sequence
```

```
<220> FEATURE:
<223> OTHER INFORMATION: primer

<400> SEQUENCE: 172
cagtcagtgg ctcagccgga agatc                                          25

<210> SEQ ID NO 173
<211> LENGTH: 24
<212> TYPE: DNA
<213> ORGANISM: Artificial Sequence
<220> FEATURE:
<223> OTHER INFORMATION: primer

<400> SEQUENCE: 173
aagaccaccc agcccatctc catg                                           24

<210> SEQ ID NO 174
<211> LENGTH: 31
<212> TYPE: DNA
<213> ORGANISM: Artificial Sequence
<220> FEATURE:
<223> OTHER INFORMATION: primer

<400> SEQUENCE: 174
gaggatgtgg agcagagtct tttcctgagt g                                   31

<210> SEQ ID NO 175
<211> LENGTH: 30
<212> TYPE: DNA
<213> ORGANISM: Artificial Sequence
<220> FEATURE:
<223> OTHER INFORMATION: primer

<400> SEQUENCE: 175
caaaagatag aacagaattc cgaggccctg                                     30

<210> SEQ ID NO 176
<211> LENGTH: 25
<212> TYPE: DNA
<213> ORGANISM: Artificial Sequence
<220> FEATURE:
<223> OTHER INFORMATION: primer

<400> SEQUENCE: 176
gaaaaccagg tggagcacag ccctc                                          25

<210> SEQ ID NO 177
<211> LENGTH: 27
<212> TYPE: DNA
<213> ORGANISM: Artificial Sequence
<220> FEATURE:
<223> OTHER INFORMATION: primer

<400> SEQUENCE: 177
cagtctgtga gccagcataa ccaccac                                        27

<210> SEQ ID NO 178
<211> LENGTH: 24
<212> TYPE: DNA
<213> ORGANISM: Artificial Sequence
<220> FEATURE:
<223> OTHER INFORMATION: primer

<400> SEQUENCE: 178
cagtcggtga cccagcttga cagc                                           24
```

```
<210> SEQ ID NO 179
<211> LENGTH: 27
<212> TYPE: DNA
<213> ORGANISM: Artificial Sequence
<220> FEATURE:
<223> OTHER INFORMATION: primer

<400> SEQUENCE: 179
cagtcagtga cccagcctga catccac                                      27

<210> SEQ ID NO 180
<211> LENGTH: 23
<212> TYPE: DNA
<213> ORGANISM: Artificial Sequence
<220> FEATURE:
<223> OTHER INFORMATION: primer

<400> SEQUENCE: 180
cagtcggtga cccagcttgg cag                                          23

<210> SEQ ID NO 181
<211> LENGTH: 29
<212> TYPE: DNA
<213> ORGANISM: Artificial Sequence
<220> FEATURE:
<223> OTHER INFORMATION: primer

<400> SEQUENCE: 181
gattcagtgg tccagacaga aggccaagt                                    29

<210> SEQ ID NO 182
<211> LENGTH: 30
<212> TYPE: DNA
<213> ORGANISM: Artificial Sequence
<220> FEATURE:
<223> OTHER INFORMATION: primer

<400> SEQUENCE: 182
aaaaaccaag tggagcagag tcctcagtcc                                   30

<210> SEQ ID NO 183
<211> LENGTH: 25
<212> TYPE: DNA
<213> ORGANISM: Artificial Sequence
<220> FEATURE:
<223> OTHER INFORMATION: primer

<400> SEQUENCE: 183
caacggaagg aggtggagca ggatc                                        25

<210> SEQ ID NO 184
<211> LENGTH: 29
<212> TYPE: DNA
<213> ORGANISM: Artificial Sequence
<220> FEATURE:
<223> OTHER INFORMATION: primer

<400> SEQUENCE: 184
caacagaagg aggtggagca gaattctgg                                    29

<210> SEQ ID NO 185
<211> LENGTH: 27
<212> TYPE: DNA
<213> ORGANISM: Artificial Sequence
<220> FEATURE:
<223> OTHER INFORMATION: primer

<400> SEQUENCE: 185
```
gagaatgtgg agcagcatcc ttcaacc                                        27

<210> SEQ ID NO 186
<211> LENGTH: 27
<212> TYPE: DNA
<213> ORGANISM: Artificial Sequence
<220> FEATURE:
<223> OTHER INFORMATION: primer

<400> SEQUENCE: 186
gagagtgtgg ggctgcatct tcctacc                                        27

<210> SEQ ID NO 187
<211> LENGTH: 33
<212> TYPE: DNA
<213> ORGANISM: Artificial Sequence
<220> FEATURE:
<223> OTHER INFORMATION: primer

<400> SEQUENCE: 187
cagaagataa ctcaaaccca accaggaatg ttc                                 33

<210> SEQ ID NO 188
<211> LENGTH: 26
<212> TYPE: DNA
<213> ORGANISM: Artificial Sequence
<220> FEATURE:
<223> OTHER INFORMATION: primer

<400> SEQUENCE: 188
aattcagtga cccagatgga agggcc                                         26

<210> SEQ ID NO 189
<211> LENGTH: 27
<212> TYPE: DNA
<213> ORGANISM: Artificial Sequence
<220> FEATURE:
<223> OTHER INFORMATION: primer

<400> SEQUENCE: 189
caacagaagg aggtggagca ggatcct                                        27

<210> SEQ ID NO 190
<211> LENGTH: 26
<212> TYPE: DNA
<213> ORGANISM: Artificial Sequence
<220> FEATURE:
<223> OTHER INFORMATION: primer

<400> SEQUENCE: 190
cagtctgtga cccagcttga cagcca                                         26

<210> SEQ ID NO 191
<211> LENGTH: 27
<212> TYPE: DNA
<213> ORGANISM: Artificial Sequence
<220> FEATURE:
<223> OTHER INFORMATION: primer

<400> SEQUENCE: 191
cagagagtga ctcagcccga gaagctc                                        27

<210> SEQ ID NO 192
<211> LENGTH: 27
<212> TYPE: DNA
<213> ORGANISM: Artificial Sequence

```
<220> FEATURE:
<223> OTHER INFORMATION: primer

<400> SEQUENCE: 192
caacagggag aagaggatcc tcaggcc                                              27

<210> SEQ ID NO 193
<211> LENGTH: 26
<212> TYPE: DNA
<213> ORGANISM: Artificial Sequence
<220> FEATURE:
<223> OTHER INFORMATION: primer

<400> SEQUENCE: 193
gactcggtta cccagacaga aggccc                                               26

<210> SEQ ID NO 194
<211> LENGTH: 33
<212> TYPE: DNA
<213> ORGANISM: Artificial Sequence
<220> FEATURE:
<223> OTHER INFORMATION: primer

<400> SEQUENCE: 194
cagaaggtaa ctcaagcgca gactgaaatt tct                                       33

<210> SEQ ID NO 195
<211> LENGTH: 25
<212> TYPE: DNA
<213> ORGANISM: Artificial Sequence
<220> FEATURE:
<223> OTHER INFORMATION: primer

<400> SEQUENCE: 195
gaagaccagg tgacgcagag tcccg                                                25

<210> SEQ ID NO 196
<211> LENGTH: 26
<212> TYPE: DNA
<213> ORGANISM: Artificial Sequence
<220> FEATURE:
<223> OTHER INFORMATION: primer

<400> SEQUENCE: 196
aaacaggagg tgacgcagat tcctgc                                               26

<210> SEQ ID NO 197
<211> LENGTH: 31
<212> TYPE: DNA
<213> ORGANISM: Artificial Sequence
<220> FEATURE:
<223> OTHER INFORMATION: primer

<400> SEQUENCE: 197
atacaagtgg agcagagtcc tccagacctg a                                         31

<210> SEQ ID NO 198
<211> LENGTH: 29
<212> TYPE: DNA
<213> ORGANISM: Artificial Sequence
<220> FEATURE:
<223> OTHER INFORMATION: primer

<400> SEQUENCE: 198
caacagaagg agaaaagtga ccagcagca                                            29
```

```
<210> SEQ ID NO 199
<211> LENGTH: 33
<212> TYPE: DNA
<213> ORGANISM: Artificial Sequence
<220> FEATURE:
<223> OTHER INFORMATION: primer

<400> SEQUENCE: 199
atactgaacg tggaacaaag tcctcagtca ctg                                   33

<210> SEQ ID NO 200
<211> LENGTH: 31
<212> TYPE: DNA
<213> ORGANISM: Artificial Sequence
<220> FEATURE:
<223> OTHER INFORMATION: primer

<400> SEQUENCE: 200
caacaggtaa tgcaaattcc tcagtaccag c                                     31

<210> SEQ ID NO 201
<211> LENGTH: 21
<212> TYPE: DNA
<213> ORGANISM: Artificial Sequence
<220> FEATURE:
<223> OTHER INFORMATION: primer

<400> SEQUENCE: 201
aagaccaccc agccccctc c                                                 21

<210> SEQ ID NO 202
<211> LENGTH: 24
<212> TYPE: DNA
<213> ORGANISM: Artificial Sequence
<220> FEATURE:
<223> OTHER INFORMATION: primer

<400> SEQUENCE: 202
cagtcggtga cccagcttga tggc                                             24

<210> SEQ ID NO 203
<211> LENGTH: 25
<212> TYPE: DNA
<213> ORGANISM: Artificial Sequence
<220> FEATURE:
<223> OTHER INFORMATION: primer

<400> SEQUENCE: 203
cagctgctgg agcagagccc tcagt                                            25

<210> SEQ ID NO 204
<211> LENGTH: 33
<212> TYPE: DNA
<213> ORGANISM: Artificial Sequence
<220> FEATURE:
<223> OTHER INFORMATION: primer

<400> SEQUENCE: 204
caacagaaga atgatgacca gcaagttaag caa                                   33

<210> SEQ ID NO 205
<211> LENGTH: 27
<212> TYPE: DNA
<213> ORGANISM: Artificial Sequence
<220> FEATURE:
<223> OTHER INFORMATION: primer

<400> SEQUENCE: 205
```
caacaaccag tgcagagtcc tcaagcc                                27

<210> SEQ ID NO 206
<211> LENGTH: 33
<212> TYPE: DNA
<213> ORGANISM: Artificial Sequence
<220> FEATURE:
<223> OTHER INFORMATION: primer

<400> SEQUENCE: 206
aagaccacac agccaaattc aatggagagt aac                         33

<210> SEQ ID NO 207
<211> LENGTH: 30
<212> TYPE: DNA
<213> ORGANISM: Artificial Sequence
<220> FEATURE:
<223> OTHER INFORMATION: primer

<400> SEQUENCE: 207
caagaactgg agcagagtcc tcagtccttg                             30

<210> SEQ ID NO 208
<211> LENGTH: 36
<212> TYPE: DNA
<213> ORGANISM: Artificial Sequence
<220> FEATURE:
<223> OTHER INFORMATION: primer

<400> SEQUENCE: 208
caacagctga atcagagtcc tcaatctatg tttatc                      36

<210> SEQ ID NO 209
<211> LENGTH: 33
<212> TYPE: DNA
<213> ORGANISM: Artificial Sequence
<220> FEATURE:
<223> OTHER INFORMATION: primer

<400> SEQUENCE: 209
gaagacaagg tggtacaaag ccctctatct ctg                         33

<210> SEQ ID NO 210
<211> LENGTH: 33
<212> TYPE: DNA
<213> ORGANISM: Artificial Sequence
<220> FEATURE:
<223> OTHER INFORMATION: primer

<400> SEQUENCE: 210
cagacagtca ctcagtctca accagagatg tct                         33

<210> SEQ ID NO 211
<211> LENGTH: 30
<212> TYPE: DNA
<213> ORGANISM: Artificial Sequence
<220> FEATURE:
<223> OTHER INFORMATION: primer

<400> SEQUENCE: 211
gagctgaaag tggaacaaaa ccctctgttc                             30

<210> SEQ ID NO 212
<211> LENGTH: 29
<212> TYPE: DNA
<213> ORGANISM: Artificial Sequence

```
<220> FEATURE:
<223> OTHER INFORMATION: primer

<400> SEQUENCE: 212
aattcagtca agcagacggg ccaaataac                                      29

<210> SEQ ID NO 213
<211> LENGTH: 28
<212> TYPE: DNA
<213> ORGANISM: Artificial Sequence
<220> FEATURE:
<223> OTHER INFORMATION: primer

<400> SEQUENCE: 213
gccaaaaatg aagtggagca gagtcctc                                       28

<210> SEQ ID NO 214
<211> LENGTH: 27
<212> TYPE: DNA
<213> ORGANISM: Artificial Sequence
<220> FEATURE:
<223> OTHER INFORMATION: primer

<400> SEQUENCE: 214
atggggagaa gtggaaactc tggttcc                                        27

<210> SEQ ID NO 215
<211> LENGTH: 34
<212> TYPE: DNA
<213> ORGANISM: Artificial Sequence
<220> FEATURE:
<223> OTHER INFORMATION: primer

<400> SEQUENCE: 215
atcagatata atgaatacat gggtcccttt ccca                                34

<210> SEQ ID NO 216
<211> LENGTH: 25
<212> TYPE: DNA
<213> ORGANISM: Artificial Sequence
<220> FEATURE:
<223> OTHER INFORMATION: primer

<400> SEQUENCE: 216
atttggccgg atgctgagtc tggtc                                          25

<210> SEQ ID NO 217
<211> LENGTH: 27
<212> TYPE: DNA
<213> ORGANISM: Artificial Sequence
<220> FEATURE:
<223> OTHER INFORMATION: primer

<400> SEQUENCE: 217
atatgggtgt acagccagcc tggtccc                                        27

<210> SEQ ID NO 218
<211> LENGTH: 31
<212> TYPE: DNA
<213> ORGANISM: Artificial Sequence
<220> FEATURE:
<223> OTHER INFORMATION: primer

<400> SEQUENCE: 218
atttggttgc acttggagtc ttgttccact c                                   31
```

```
<210> SEQ ID NO 219
<211> LENGTH: 32
<212> TYPE: DNA
<213> ORGANISM: Artificial Sequence
<220> FEATURE:
<223> OTHER INFORMATION: primer

<400> SEQUENCE: 219
atacggatga acaataaggc tggttcctct tc                                     32

<210> SEQ ID NO 220
<211> LENGTH: 30
<212> TYPE: DNA
<213> ORGANISM: Artificial Sequence
<220> FEATURE:
<223> OTHER INFORMATION: primer

<400> SEQUENCE: 220
atttggtatg accaccactt ggttcccctt                                        30

<210> SEQ ID NO 221
<211> LENGTH: 27
<212> TYPE: DNA
<213> ORGANISM: Artificial Sequence
<220> FEATURE:
<223> OTHER INFORMATION: primer

<400> SEQUENCE: 221
atttggactg accagaagtc gggtgcc                                           27

<210> SEQ ID NO 222
<211> LENGTH: 37
<212> TYPE: DNA
<213> ORGANISM: Artificial Sequence
<220> FEATURE:
<223> OTHER INFORMATION: primer

<400> SEQUENCE: 222
atttgcttta acaaatagtc ttgttcctgc tccaaag                                37

<210> SEQ ID NO 223
<211> LENGTH: 32
<212> TYPE: DNA
<213> ORGANISM: Artificial Sequence
<220> FEATURE:
<223> OTHER INFORMATION: primer

<400> SEQUENCE: 223
attgagttcc acttttagct gagtgcctgt cc                                     32

<210> SEQ ID NO 224
<211> LENGTH: 33
<212> TYPE: DNA
<213> ORGANISM: Artificial Sequence
<220> FEATURE:
<223> OTHER INFORMATION: primer

<400> SEQUENCE: 224
atctggagag actagaagca tagtccccTT ccc                                    33

<210> SEQ ID NO 225
<211> LENGTH: 26
<212> TYPE: DNA
<213> ORGANISM: Artificial Sequence
<220> FEATURE:
<223> OTHER INFORMATION: primer

<400> SEQUENCE: 225
```

```
atcaggcctg accagcagtc tggtcc                                        26

<210> SEQ ID NO 226
<211> LENGTH: 30
<212> TYPE: DNA
<213> ORGANISM: Artificial Sequence
<220> FEATURE:
<223> OTHER INFORMATION: primer

<400> SEQUENCE: 226
atttgggatg acttggagct ttgttccaat                                    30

<210> SEQ ID NO 227
<211> LENGTH: 34
<212> TYPE: DNA
<213> ORGANISM: Artificial Sequence
<220> FEATURE:
<223> OTHER INFORMATION: primer

<400> SEQUENCE: 227
atcaggtttt actgataatc ttgtcccact ccca                               34

<210> SEQ ID NO 228
<211> LENGTH: 32
<212> TYPE: DNA
<213> ORGANISM: Artificial Sequence
<220> FEATURE:
<223> OTHER INFORMATION: primer

<400> SEQUENCE: 228
attggaactc actgataagg tgggttccct tc                                 32

<210> SEQ ID NO 229
<211> LENGTH: 32
<212> TYPE: DNA
<213> ORGANISM: Artificial Sequence
<220> FEATURE:
<223> OTHER INFORMATION: primer

<400> SEQUENCE: 229
attaagatcc acctttaaca tggttcccct tg                                 32

<210> SEQ ID NO 230
<211> LENGTH: 32
<212> TYPE: DNA
<213> ORGANISM: Artificial Sequence
<220> FEATURE:
<223> OTHER INFORMATION: primer

<400> SEQUENCE: 230
atttggttta actagcaccc tggttcctcc tc                                 32

<210> SEQ ID NO 231
<211> LENGTH: 32
<212> TYPE: DNA
<213> ORGANISM: Artificial Sequence
<220> FEATURE:
<223> OTHER INFORMATION: primer

<400> SEQUENCE: 231
atcaggccag acagtcaact gagttcctct tc                                 32

<210> SEQ ID NO 232
<211> LENGTH: 33
<212> TYPE: DNA
<213> ORGANISM: Artificial Sequence
```

```
<220> FEATURE:
<223> OTHER INFORMATION: primer

<400> SEQUENCE: 232
atttggagtg acattatgtt tggatccctt tcc                        33

<210> SEQ ID NO 233
<211> LENGTH: 32
<212> TYPE: DNA
<213> ORGANISM: Artificial Sequence
<220> FEATURE:
<223> OTHER INFORMATION: primer

<400> SEQUENCE: 233
atttgctctt acagttactg tggttccggc tc                         32

<210> SEQ ID NO 234
<211> LENGTH: 33
<212> TYPE: DNA
<213> ORGANISM: Artificial Sequence
<220> FEATURE:
<223> OTHER INFORMATION: primer

<400> SEQUENCE: 234
atttggtttt acattgagtt tggtcccaga tcc                        33

<210> SEQ ID NO 235
<211> LENGTH: 33
<212> TYPE: DNA
<213> ORGANISM: Artificial Sequence
<220> FEATURE:
<223> OTHER INFORMATION: primer

<400> SEQUENCE: 235
atcaggtaaa acagtcaatt gtgtcccaga tcc                        33

<210> SEQ ID NO 236
<211> LENGTH: 31
<212> TYPE: DNA
<213> ORGANISM: Artificial Sequence
<220> FEATURE:
<223> OTHER INFORMATION: primer

<400> SEQUENCE: 236
attgggtttc acagataact ccgttccctg t                          31

<210> SEQ ID NO 237
<211> LENGTH: 25
<212> TYPE: DNA
<213> ORGANISM: Artificial Sequence
<220> FEATURE:
<223> OTHER INFORMATION: primer

<400> SEQUENCE: 237
atctggggtg accacaacct gggtc                                 25

<210> SEQ ID NO 238
<211> LENGTH: 25
<212> TYPE: DNA
<213> ORGANISM: Artificial Sequence
<220> FEATURE:
<223> OTHER INFORMATION: primer

<400> SEQUENCE: 238
atctggggtg accacaacct gggtc                                 25
```

```
<210> SEQ ID NO 239
<211> LENGTH: 26
<212> TYPE: DNA
<213> ORGANISM: Artificial Sequence
<220> FEATURE:
<223> OTHER INFORMATION: primer

<400> SEQUENCE: 239
atagggcagc acggacaatc tggttc                                          26

<210> SEQ ID NO 240
<211> LENGTH: 30
<212> TYPE: DNA
<213> ORGANISM: Artificial Sequence
<220> FEATURE:
<223> OTHER INFORMATION: primer

<400> SEQUENCE: 240
atttggcttc acagtgagcg tagtcccatc                                      30

<210> SEQ ID NO 241
<211> LENGTH: 30
<212> TYPE: DNA
<213> ORGANISM: Artificial Sequence
<220> FEATURE:
<223> OTHER INFORMATION: primer

<400> SEQUENCE: 241
atttggtatg accgagagtt tggtccccttt                                     30

<210> SEQ ID NO 242
<211> LENGTH: 32
<212> TYPE: DNA
<213> ORGANISM: Artificial Sequence
<220> FEATURE:
<223> OTHER INFORMATION: primer

<400> SEQUENCE: 242
atttgcaatc acagaaagtc ttgtgcccctt tc                                  32

<210> SEQ ID NO 243
<211> LENGTH: 32
<212> TYPE: DNA
<213> ORGANISM: Artificial Sequence
<220> FEATURE:
<223> OTHER INFORMATION: primer

<400> SEQUENCE: 243
attggggaga atatgaagtc gtgtcccttt tc                                   32

<210> SEQ ID NO 244
<211> LENGTH: 26
<212> TYPE: DNA
<213> ORGANISM: Artificial Sequence
<220> FEATURE:
<223> OTHER INFORMATION: primer

<400> SEQUENCE: 244
attgggcttc accaccagct gagttc                                          26

<210> SEQ ID NO 245
<211> LENGTH: 26
<212> TYPE: DNA
<213> ORGANISM: Artificial Sequence
<220> FEATURE:
<223> OTHER INFORMATION: primer

<400> SEQUENCE: 245
```

```
atttggctgg acagcaagca gagtgc                                          26

<210> SEQ ID NO 246
<211> LENGTH: 31
<212> TYPE: DNA
<213> ORGANISM: Artificial Sequence
<220> FEATURE:
<223> OTHER INFORMATION: primer

<400> SEQUENCE: 246
atctggcttt ataattagct tggtcccagc g                                    31

<210> SEQ ID NO 247
<211> LENGTH: 32
<212> TYPE: DNA
<213> ORGANISM: Artificial Sequence
<220> FEATURE:
<223> OTHER INFORMATION: primer

<400> SEQUENCE: 247
atttggaaag acttgtaatc tggtcccagt cc                                   32

<210> SEQ ID NO 248
<211> LENGTH: 31
<212> TYPE: DNA
<213> ORGANISM: Artificial Sequence
<220> FEATURE:
<223> OTHER INFORMATION: primer

<400> SEQUENCE: 248
atgtggtaaa acaatcactt gagtgccgga c                                    31

<210> SEQ ID NO 249
<211> LENGTH: 31
<212> TYPE: DNA
<213> ORGANISM: Artificial Sequence
<220> FEATURE:
<223> OTHER INFORMATION: primer

<400> SEQUENCE: 249 atagggaat aacggtgagt ctcgttccag t                                     31

<210> SEQ ID NO 250
<211> LENGTH: 33
<212> TYPE: DNA
<213> ORGANISM: Artificial Sequence
<220> FEATURE:
<223> OTHER INFORMATION: primer

<400> SEQUENCE: 250
atctggtttt acttggtaaa gttgtcccctt gcc                                 33

<210> SEQ ID NO 251
<211> LENGTH: 28
<212> TYPE: DNA
<213> ORGANISM: Artificial Sequence
<220> FEATURE:
<223> OTHER INFORMATION: primer

<400> SEQUENCE: 251
attcggattt actgccaggc ttgttccc                                        28

<210> SEQ ID NO 252
<211> LENGTH: 29
<212> TYPE: DNA
<213> ORGANISM: Artificial Sequence
```

```
<220> FEATURE:
<223> OTHER INFORMATION: primer

<400> SEQUENCE: 252
atggggtttg accattaacc ttgttcccc                                    29

<210> SEQ ID NO 253
<211> LENGTH: 29
<212> TYPE: DNA
<213> ORGANISM: Artificial Sequence
<220> FEATURE:
<223> OTHER INFORMATION: primer

<400> SEQUENCE: 253
atttgctaaa accttcagcc tggtgcctg                                    29

<210> SEQ ID NO 254
<211> LENGTH: 25
<212> TYPE: DNA
<213> ORGANISM: Artificial Sequence
<220> FEATURE:
<223> OTHER INFORMATION: primer

<400> SEQUENCE: 254
atggggtgtg accaacagcg aggtg                                        25

<210> SEQ ID NO 255
<211> LENGTH: 38
<212> TYPE: DNA
<213> ORGANISM: Artificial Sequence
<220> FEATURE:
<223> OTHER INFORMATION: primer

<400> SEQUENCE: 255
atttggttta acagagagtt tagtgccttt tccaaaga                          38

<210> SEQ ID NO 256
<211> LENGTH: 32
<212> TYPE: DNA
<213> ORGANISM: Artificial Sequence
<220> FEATURE:
<223> OTHER INFORMATION: primer

<400> SEQUENCE: 256
atttggtttt actgtcagtc tggtccctgc tc                                32

<210> SEQ ID NO 257
<211> LENGTH: 30
<212> TYPE: DNA
<213> ORGANISM: Artificial Sequence
<220> FEATURE:
<223> OTHER INFORMATION: primer

<400> SEQUENCE: 257
atcgagcgtg acctgaagtc ttgttccagt                                   30

<210> SEQ ID NO 258
<211> LENGTH: 31
<212> TYPE: DNA
<213> ORGANISM: Artificial Sequence
<220> FEATURE:
<223> OTHER INFORMATION: primer

<400> SEQUENCE: 258
atagggctgg atgattagat gagtcccttt g                                 31
```

```
<210> SEQ ID NO 259
<211> LENGTH: 28
<212> TYPE: DNA
<213> ORGANISM: Artificial Sequence
<220> FEATURE:
<223> OTHER INFORMATION: primer

<400> SEQUENCE: 259
attgggccta actgctaaac gagtcccg                                          28

<210> SEQ ID NO 260
<211> LENGTH: 31
<212> TYPE: DNA
<213> ORGANISM: Artificial Sequence
<220> FEATURE:
<223> OTHER INFORMATION: primer

<400> SEQUENCE: 260
ataggacttg actctcagaa tggttcctgc g                                      31

<210> SEQ ID NO 261
<211> LENGTH: 32
<212> TYPE: DNA
<213> ORGANISM: Artificial Sequence
<220> FEATURE:
<223> OTHER INFORMATION: primer

<400> SEQUENCE: 261
attgggtatg atggtgagtc ttgttccagt cc                                     32

<210> SEQ ID NO 262
<211> LENGTH: 30
<212> TYPE: DNA
<213> ORGANISM: Artificial Sequence
<220> FEATURE:
<223> OTHER INFORMATION: primer

<400> SEQUENCE: 262
atttggaatg accgtcaaac ttgtccctgt                                        30

<210> SEQ ID NO 263
<211> LENGTH: 31
<212> TYPE: DNA
<213> ORGANISM: Artificial Sequence
<220> FEATURE:
<223> OTHER INFORMATION: primer

<400> SEQUENCE: 263
atttggaatg actgataagc ttgtccctgg c                                      31

<210> SEQ ID NO 264
<211> LENGTH: 33
<212> TYPE: DNA
<213> ORGANISM: Artificial Sequence
<220> FEATURE:
<223> OTHER INFORMATION: primer

<400> SEQUENCE: 264
atttggcttc acagttagtc atgtctcctt tcc                                    33

<210> SEQ ID NO 265
<211> LENGTH: 30
<212> TYPE: DNA
<213> ORGANISM: Artificial Sequence
<220> FEATURE:
<223> OTHER INFORMATION: primer

<400> SEQUENCE: 265
```

```
atttggatgg acagtcaaga tggtcccttg                                    30

<210> SEQ ID NO 266
<211> LENGTH: 33
<212> TYPE: DNA
<213> ORGANISM: Artificial Sequence
<220> FEATURE:
<223> OTHER INFORMATION: primer

<400> SEQUENCE: 266
atttggattc acggttaaga gagttccttt tcc                                 33

<210> SEQ ID NO 267
<211> LENGTH: 27
<212> TYPE: DNA
<213> ORGANISM: Artificial Sequence
<220> FEATURE:
<223> OTHER INFORMATION: primer

<400> SEQUENCE: 267
gaacctgaag tcacccagac tcccagc                                       27

<210> SEQ ID NO 268
<211> LENGTH: 30
<212> TYPE: DNA
<213> ORGANISM: Artificial Sequence
<220> FEATURE:
<223> OTHER INFORMATION: primer

<400> SEQUENCE: 268
gctgtttccc agactccaaa atacctggtc                                    30

<210> SEQ ID NO 269
<211> LENGTH: 30
<212> TYPE: DNA
<213> ORGANISM: Artificial Sequence
<220> FEATURE:
<223> OTHER INFORMATION: primer

<400> SEQUENCE: 269
gaagttaccc agacaccaaa acacctggtc                                    30

<210> SEQ ID NO 270
<211> LENGTH: 35
<212> TYPE: DNA
<213> ORGANISM: Artificial Sequence
<220> FEATURE:
<223> OTHER INFORMATION: primer

<400> SEQUENCE: 270
ggagtcactc aaactccaag atatctgatc aaaac                              35

<210> SEQ ID NO 271
<211> LENGTH: 27
<212> TYPE: DNA
<213> ORGANISM: Artificial Sequence
<220> FEATURE:
<223> OTHER INFORMATION: primer

<400> SEQUENCE: 271
ggtgtcactc agaccccaaa attccag                                       27

<210> SEQ ID NO 272
<211> LENGTH: 28
<212> TYPE: DNA
<213> ORGANISM: Artificial Sequence
```

```
<220> FEATURE:
<223> OTHER INFORMATION: primer

<400> SEQUENCE: 272
ggagtctccc agtccctgag acacaagg                                    28

<210> SEQ ID NO 273
<211> LENGTH: 28
<212> TYPE: DNA
<213> ORGANISM: Artificial Sequence
<220> FEATURE:
<223> OTHER INFORMATION: primer

<400> SEQUENCE: 273
ggagttacgc agacaccaag acacctgg                                    28

<210> SEQ ID NO 274
<211> LENGTH: 26
<212> TYPE: DNA
<213> ORGANISM: Artificial Sequence
<220> FEATURE:
<223> OTHER INFORMATION: primer

<400> SEQUENCE: 274
ggtgtcactc agaccccaaa attccg                                      26

<210> SEQ ID NO 275
<211> LENGTH: 28
<212> TYPE: DNA
<213> ORGANISM: Artificial Sequence
<220> FEATURE:
<223> OTHER INFORMATION: primer

<400> SEQUENCE: 275
ggagttacgc agacaccaag acacctgg                                    28

<210> SEQ ID NO 276
<211> LENGTH: 26
<212> TYPE: DNA
<213> ORGANISM: Artificial Sequence
<220> FEATURE:
<223> OTHER INFORMATION: primer

<400> SEQUENCE: 276
ggtgtcactc agaccccaaa attccg                                      26

<210> SEQ ID NO 277
<211> LENGTH: 27
<212> TYPE: DNA
<213> ORGANISM: Artificial Sequence
<220> FEATURE:
<223> OTHER INFORMATION: primer

<400> SEQUENCE: 277
ggagtctccc agtcccccag taacaag                                     27

<210> SEQ ID NO 278
<211> LENGTH: 25
<212> TYPE: DNA
<213> ORGANISM: Artificial Sequence
<220> FEATURE:
<223> OTHER INFORMATION: primer

<400> SEQUENCE: 278
gggatcaccc aggcaccaac atctc                                       25
```

```
<210> SEQ ID NO 279
<211> LENGTH: 27
<212> TYPE: DNA
<213> ORGANISM: Artificial Sequence
<220> FEATURE:
<223> OTHER INFORMATION: primer

<400> SEQUENCE: 279
ggagtctccc agaccccag taacaag                                        27

<210> SEQ ID NO 280
<211> LENGTH: 26
<212> TYPE: DNA
<213> ORGANISM: Artificial Sequence
<220> FEATURE:
<223> OTHER INFORMATION: primer

<400> SEQUENCE: 280
ggagtcaccc aaagtcccac acacct                                        26

<210> SEQ ID NO 281
<211> LENGTH: 26
<212> TYPE: DNA
<213> ORGANISM: Artificial Sequence
<220> FEATURE:
<223> OTHER INFORMATION: primer

<400> SEQUENCE: 281
ggagtcacac aaaccccaaa gcacct                                        26

<210> SEQ ID NO 282
<211> LENGTH: 28
<212> TYPE: DNA
<213> ORGANISM: Artificial Sequence
<220> FEATURE:
<223> OTHER INFORMATION: primer

<400> SEQUENCE: 282
gaaatcaccc agagcccaag acacaaga                                      28

<210> SEQ ID NO 283
<211> LENGTH: 31
<212> TYPE: DNA
<213> ORGANISM: Artificial Sequence
<220> FEATURE:
<223> OTHER INFORMATION: primer

<400> SEQUENCE: 283
gaagttgccc agtcccccag atataagatt a                                  31

<210> SEQ ID NO 284
<211> LENGTH: 29
<212> TYPE: DNA
<213> ORGANISM: Artificial Sequence
<220> FEATURE:
<223> OTHER INFORMATION: primer

<400> SEQUENCE: 284
ggaatcaccc agagcccaag atacaagat                                     29

<210> SEQ ID NO 285
<211> LENGTH: 36
<212> TYPE: DNA
<213> ORGANISM: Artificial Sequence
<220> FEATURE:
<223> OTHER INFORMATION: primer

<400> SEQUENCE: 285
```
ggagttgccc agtctcccag atataagatt atagag        36

<210> SEQ ID NO 286
<211> LENGTH: 27
<212> TYPE: DNA
<213> ORGANISM: Artificial Sequence
<220> FEATURE:
<223> OTHER INFORMATION: primer

<400> SEQUENCE: 286
ggtgtcactc agaccccaaa attccag        27

<210> SEQ ID NO 287
<211> LENGTH: 28
<212> TYPE: DNA
<213> ORGANISM: Artificial Sequence
<220> FEATURE:
<223> OTHER INFORMATION: primer

<400> SEQUENCE: 287
ggagtctccc agtccccaag gtacaaag        28

<210> SEQ ID NO 288
<211> LENGTH: 26
<212> TYPE: DNA
<213> ORGANISM: Artificial Sequence
<220> FEATURE:
<223> OTHER INFORMATION: primer

<400> SEQUENCE: 288
ggagtcaccc aaagtcccac acacct        26

<210> SEQ ID NO 289
<211> LENGTH: 26
<212> TYPE: DNA
<213> ORGANISM: Artificial Sequence
<220> FEATURE:
<223> OTHER INFORMATION: primer

<400> SEQUENCE: 289
ggtgtcactc agaccccaaa attccg        26

<210> SEQ ID NO 290
<211> LENGTH: 26
<212> TYPE: DNA
<213> ORGANISM: Artificial Sequence
<220> FEATURE:
<223> OTHER INFORMATION: primer

<400> SEQUENCE: 290
ggagtctccc agtccccaag gtacga        26

<210> SEQ ID NO 291
<211> LENGTH: 26
<212> TYPE: DNA
<213> ORGANISM: Artificial Sequence
<220> FEATURE:
<223> OTHER INFORMATION: primer

<400> SEQUENCE: 291
ggagtcaccc aaagtcccac acacct        26

<210> SEQ ID NO 292
<211> LENGTH: 27
<212> TYPE: DNA
<213> ORGANISM: Artificial Sequence

```
<220> FEATURE:
<223> OTHER INFORMATION: primer

<400> SEQUENCE: 292
ggtgtcactc agaccccaaa attccac                                        27

<210> SEQ ID NO 293
<211> LENGTH: 30
<212> TYPE: DNA
<213> ORGANISM: Artificial Sequence
<220> FEATURE:
<223> OTHER INFORMATION: primer

<400> SEQUENCE: 293
ggagtctccc agtctcccag gtacaaagtc                                     30

<210> SEQ ID NO 294
<211> LENGTH: 26
<212> TYPE: DNA
<213> ORGANISM: Artificial Sequence
<220> FEATURE:
<223> OTHER INFORMATION: primer

<400> SEQUENCE: 294
ggagtcaccc aaagtcccac acacct                                         26

<210> SEQ ID NO 295
<211> LENGTH: 29
<212> TYPE: DNA
<213> ORGANISM: Artificial Sequence
<220> FEATURE:
<223> OTHER INFORMATION: primer

<400> SEQUENCE: 295
ggtgtcactc agaccccaaa attccacat                                      29

<210> SEQ ID NO 296
<211> LENGTH: 30
<212> TYPE: DNA
<213> ORGANISM: Artificial Sequence
<220> FEATURE:
<223> OTHER INFORMATION: primer

<400> SEQUENCE: 296
ggagtctccc agtctcccag gtacaaagtc                                     30

<210> SEQ ID NO 297
<211> LENGTH: 26
<212> TYPE: DNA
<213> ORGANISM: Artificial Sequence
<220> FEATURE:
<223> OTHER INFORMATION: primer

<400> SEQUENCE: 297
ggagtcaccc aaagtcccac acacct                                         26

<210> SEQ ID NO 298
<211> LENGTH: 29
<212> TYPE: DNA
<213> ORGANISM: Artificial Sequence
<220> FEATURE:
<223> OTHER INFORMATION: primer

<400> SEQUENCE: 298
ggtgtcactc agaccccaaa attccacat                                      29
```

```
<210> SEQ ID NO 299
<211> LENGTH: 30
<212> TYPE: DNA
<213> ORGANISM: Artificial Sequence
<220> FEATURE:
<223> OTHER INFORMATION: primer

<400> SEQUENCE: 299
ggagtctccc agtcccctag gtacaaagtc                                    30

<210> SEQ ID NO 300
<211> LENGTH: 28
<212> TYPE: DNA
<213> ORGANISM: Artificial Sequence
<220> FEATURE:
<223> OTHER INFORMATION: primer

<400> SEQUENCE: 300
ggagtcacac aaagtcccac acacctga                                      28

<210> SEQ ID NO 301
<211> LENGTH: 27
<212> TYPE: DNA
<213> ORGANISM: Artificial Sequence
<220> FEATURE:
<223> OTHER INFORMATION: primer

<400> SEQUENCE: 301
ggagtctccc agaaccccag acacaag                                       27

<210> SEQ ID NO 302
<211> LENGTH: 29
<212> TYPE: DNA
<213> ORGANISM: Artificial Sequence
<220> FEATURE:
<223> OTHER INFORMATION: primer

<400> SEQUENCE: 302
ggagtcatcc agtccccaag acatctgat                                     29

<210> SEQ ID NO 303
<211> LENGTH: 27
<212> TYPE: DNA
<213> ORGANISM: Artificial Sequence
<220> FEATURE:
<223> OTHER INFORMATION: primer

<400> SEQUENCE: 303
ggaatcaccc agagcccaag acacaag                                       27

<210> SEQ ID NO 304
<211> LENGTH: 38
<212> TYPE: DNA
<213> ORGANISM: Artificial Sequence
<220> FEATURE:
<223> OTHER INFORMATION: primer

<400> SEQUENCE: 304
ggagtggttc agtctcccag atataagatt atagagaa                           38

<210> SEQ ID NO 305
<211> LENGTH: 25
<212> TYPE: DNA
<213> ORGANISM: Artificial Sequence
<220> FEATURE:
<223> OTHER INFORMATION: primer

<400> SEQUENCE: 305
```

```
ggagttatcc agtcaccccg ccatg                                    25

<210> SEQ ID NO 306
<211> LENGTH: 24
<212> TYPE: DNA
<213> ORGANISM: Artificial Sequence
<220> FEATURE:
<223> OTHER INFORMATION: primer

<400> SEQUENCE: 306
ggagttatcc agtcaccccg gcac                                     24

<210> SEQ ID NO 307
<211> LENGTH: 27
<212> TYPE: DNA
<213> ORGANISM: Artificial Sequence
<220> FEATURE:
<223> OTHER INFORMATION: primer

<400> SEQUENCE: 307
agagtcaccc agacaccaag gcacaag                                  27

<210> SEQ ID NO 308
<211> LENGTH: 27
<212> TYPE: DNA
<213> ORGANISM: Artificial Sequence
<220> FEATURE:
<223> OTHER INFORMATION: primer

<400> SEQUENCE: 308
ggagttactc agttccccag ccacagc                                  27

<210> SEQ ID NO 309
<211> LENGTH: 30
<212> TYPE: DNA
<213> ORGANISM: Artificial Sequence
<220> FEATURE:
<223> OTHER INFORMATION: primer

<400> SEQUENCE: 309
atggtcatcc agaacccaag ataccaggtt                               30

<210> SEQ ID NO 310
<211> LENGTH: 23
<212> TYPE: DNA
<213> ORGANISM: Artificial Sequence
<220> FEATURE:
<223> OTHER INFORMATION: primer

<400> SEQUENCE: 310
gagcctggag tcagccagac ccc                                      23

<210> SEQ ID NO 311
<211> LENGTH: 24
<212> TYPE: DNA
<213> ORGANISM: Artificial Sequence
<220> FEATURE:
<223> OTHER INFORMATION: primer

<400> SEQUENCE: 311
ggcgtcatgc agaacccaag acac                                     24

<210> SEQ ID NO 312
<211> LENGTH: 31
<212> TYPE: DNA
<213> ORGANISM: Artificial Sequence
```

```
<220> FEATURE:
<223> OTHER INFORMATION: primer

<400> SEQUENCE: 312
ggaatcactc agtccccaaa gtacctgttc a                                    31

<210> SEQ ID NO 313
<211> LENGTH: 26
<212> TYPE: DNA
<213> ORGANISM: Artificial Sequence
<220> FEATURE:
<223> OTHER INFORMATION: primer

<400> SEQUENCE: 313
gctgtcgtct ctcaacatcc gagctg                                          26

<210> SEQ ID NO 314
<211> LENGTH: 24
<212> TYPE: DNA
<213> ORGANISM: Artificial Sequence
<220> FEATURE:
<223> OTHER INFORMATION: primer

<400> SEQUENCE: 314
attccagctc actggggctg gatg                                            24

<210> SEQ ID NO 315
<211> LENGTH: 31
<212> TYPE: DNA
<213> ORGANISM: Artificial Sequence
<220> FEATURE:
<223> OTHER INFORMATION: primer

<400> SEQUENCE: 315
aaagtcacac agactccagg acatttggtc a                                    31

<210> SEQ ID NO 316
<211> LENGTH: 30
<212> TYPE: DNA
<213> ORGANISM: Artificial Sequence
<220> FEATURE:
<223> OTHER INFORMATION: primer

<400> SEQUENCE: 316
gatgttaccc agaccccaag gaataggatc                                      30

<210> SEQ ID NO 317
<211> LENGTH: 35
<212> TYPE: DNA
<213> ORGANISM: Artificial Sequence
<220> FEATURE:
<223> OTHER INFORMATION: primer

<400> SEQUENCE: 317
gacatctacc agaccccaag ataccttgtt atagg                                35

<210> SEQ ID NO 318
<211> LENGTH: 35
<212> TYPE: DNA
<213> ORGANISM: Artificial Sequence
<220> FEATURE:
<223> OTHER INFORMATION: primer

<400> SEQUENCE: 318
gtagttacac aattcccaag acacagaatc attgg                                35
```

```
<210> SEQ ID NO 319
<211> LENGTH: 30
<212> TYPE: DNA
<213> ORGANISM: Artificial Sequence
<220> FEATURE:
<223> OTHER INFORMATION: primer

<400> SEQUENCE: 319
caagtgaccc agaacccaag atacctcatc                                    30

<210> SEQ ID NO 320
<211> LENGTH: 35
<212> TYPE: DNA
<213> ORGANISM: Artificial Sequence
<220> FEATURE:
<223> OTHER INFORMATION: primer

<400> SEQUENCE: 320
tcctctacaa ctgtgagtct ggtgccttgt ccaaa                              35

<210> SEQ ID NO 321
<211> LENGTH: 31
<212> TYPE: DNA
<213> ORGANISM: Artificial Sequence
<220> FEATURE:
<223> OTHER INFORMATION: primer

<400> SEQUENCE: 321
tcctctacaa cggttaacct ggtccccgaa c                                  31

<210> SEQ ID NO 322
<211> LENGTH: 34
<212> TYPE: DNA
<213> ORGANISM: Artificial Sequence
<220> FEATURE:
<223> OTHER INFORMATION: primer

<400> SEQUENCE: 322
tcctctacaa cagtgagcca acttccctct ccaa                               34

<210> SEQ ID NO 323
<211> LENGTH: 31
<212> TYPE: DNA
<213> ORGANISM: Artificial Sequence
<220> FEATURE:
<223> OTHER INFORMATION: primer

<400> SEQUENCE: 323
tcctccaaga cagagagctg ggttccactg c                                  31

<210> SEQ ID NO 324
<211> LENGTH: 33
<212> TYPE: DNA
<213> ORGANISM: Artificial Sequence
<220> FEATURE:
<223> OTHER INFORMATION: primer

<400> SEQUENCE: 324
tcctctagga tggagagtcg agtcccatca cca                                33

<210> SEQ ID NO 325
<211> LENGTH: 30
<212> TYPE: DNA
<213> ORGANISM: Artificial Sequence
<220> FEATURE:
<223> OTHER INFORMATION: primer

<400> SEQUENCE: 325
```
tcctctgtca cagtgagcct ggtcccgttc                                    30

<210> SEQ ID NO 326
<211> LENGTH: 28
<212> TYPE: DNA
<213> ORGANISM: Artificial Sequence
<220> FEATURE:
<223> OTHER INFORMATION: primer

<400> SEQUENCE: 326
tcctctagca cggtgagccg tgtccctg                                      28

<210> SEQ ID NO 327
<211> LENGTH: 32
<212> TYPE: DNA
<213> ORGANISM: Artificial Sequence
<220> FEATURE:
<223> OTHER INFORMATION: primer

<400> SEQUENCE: 327
tcctccagta cggtcagcct agagccttct cc                                 32

<210> SEQ ID NO 328
<211> LENGTH: 27
<212> TYPE: DNA
<213> ORGANISM: Artificial Sequence
<220> FEATURE:
<223> OTHER INFORMATION: primer

<400> SEQUENCE: 328
tcctccagaa ccaggagtcc tccgccc                                       27

<210> SEQ ID NO 329
<211> LENGTH: 25
<212> TYPE: DNA
<213> ORGANISM: Artificial Sequence
<220> FEATURE:
<223> OTHER INFORMATION: primer

<400> SEQUENCE: 329
tcctcgagca ctgtcagccg ggtgc                                         25

<210> SEQ ID NO 330
<211> LENGTH: 26
<212> TYPE: DNA
<213> ORGANISM: Artificial Sequence
<220> FEATURE:
<223> OTHER INFORMATION: primer

<400> SEQUENCE: 330
tcctccagca ctgagagccg ggtccc                                        26

<210> SEQ ID NO 331
<211> LENGTH: 24
<212> TYPE: DNA
<213> ORGANISM: Artificial Sequence
<220> FEATURE:
<223> OTHER INFORMATION: primer

<400> SEQUENCE: 331
tcctcgagca ccaggagccg cgtg                                          24

<210> SEQ ID NO 332
<211> LENGTH: 25
<212> TYPE: DNA
<213> ORGANISM: Artificial Sequence

```
<220> FEATURE:
<223> OTHER INFORMATION: primer

<400> SEQUENCE: 332
tcctccagca cggtcagcct gctgc                                    25

<210> SEQ ID NO 333
<211> LENGTH: 26
<212> TYPE: DNA
<213> ORGANISM: Artificial Sequence
<220> FEATURE:
<223> OTHER INFORMATION: primer

<400> SEQUENCE: 333
tcctctgtga ccgtgagcct ggtgcc                                   26

<210> SEQ ID NO 334
<211> LENGTH: 46
<212> TYPE: DNA
<213> ORGANISM: Artificial Sequence
<220> FEATURE:
<223> OTHER INFORMATION: primer

<400> SEQUENCE: 334
tacaggaggg ctcggcagga caaaacattg accagcccac tgagat            46

<210> SEQ ID NO 335
<211> LENGTH: 47
<212> TYPE: DNA
<213> ORGANISM: Artificial Sequence
<220> FEATURE:
<223> OTHER INFORMATION: primer

<400> SEQUENCE: 335
tacaggaggg ctcggcaaag gaccaagtgt ttcagccttc cacagtg           47

<210> SEQ ID NO 336
<211> LENGTH: 42
<212> TYPE: DNA
<213> ORGANISM: Artificial Sequence
<220> FEATURE:
<223> OTHER INFORMATION: primer

<400> SEQUENCE: 336
tacaggaggg ctcggcacag tcagtggctc agccggaaga tc                42

<210> SEQ ID NO 337
<211> LENGTH: 41
<212> TYPE: DNA
<213> ORGANISM: Artificial Sequence
<220> FEATURE:
<223> OTHER INFORMATION: primer

<400> SEQUENCE: 337
tacaggaggg ctcggcaaag accacccagc ccatctccat g                 41

<210> SEQ ID NO 338
<211> LENGTH: 47
<212> TYPE: DNA
<213> ORGANISM: Artificial Sequence
<220> FEATURE:
<223> OTHER INFORMATION: primer

<400> SEQUENCE: 338
tacaggaggg ctcggcaagg atgtggagca gagtctttt ctgagtg            47
```

```
<210> SEQ ID NO 339
<211> LENGTH: 47
<212> TYPE: DNA
<213> ORGANISM: Artificial Sequence
<220> FEATURE:
<223> OTHER INFORMATION: primer

<400> SEQUENCE: 339
tacaggaggg ctcggcacaa aagatagaac agaattccga ggccctg          47

<210> SEQ ID NO 340
<211> LENGTH: 42
<212> TYPE: DNA
<213> ORGANISM: Artificial Sequence
<220> FEATURE:
<223> OTHER INFORMATION: primer

<400> SEQUENCE: 340
tacaggaggg ctcggcagaa aaccaggtgg agcacagccc tc               42

<210> SEQ ID NO 341
<211> LENGTH: 44
<212> TYPE: DNA
<213> ORGANISM: Artificial Sequence
<220> FEATURE:
<223> OTHER INFORMATION: primer

<400> SEQUENCE: 341
tacaggaggg ctcggcacag tctgtgagcc agcataacca ccac             44

<210> SEQ ID NO 342
<211> LENGTH: 41
<212> TYPE: DNA
<213> ORGANISM: Artificial Sequence
<220> FEATURE:
<223> OTHER INFORMATION: primer

<400> SEQUENCE: 342
tacaggaggg ctcggcacag tcggtgaccc agcttgacag c                41

<210> SEQ ID NO 343
<211> LENGTH: 44
<212> TYPE: DNA
<213> ORGANISM: Artificial Sequence
<220> FEATURE:
<223> OTHER INFORMATION: primer

<400> SEQUENCE: 343
tacaggaggg ctcggcacag tcagtgaccc agcctgacat ccac             44

<210> SEQ ID NO 344
<211> LENGTH: 40
<212> TYPE: DNA
<213> ORGANISM: Artificial Sequence
<220> FEATURE:
<223> OTHER INFORMATION: primer

<400> SEQUENCE: 344
tacaggaggg ctcggcacag tcggtgaccc agcttggcag                  40

<210> SEQ ID NO 345
<211> LENGTH: 46
<212> TYPE: DNA
<213> ORGANISM: Artificial Sequence
<220> FEATURE:
<223> OTHER INFORMATION: primer

<400> SEQUENCE: 345
```
tacaggaggg ctcggcagat tcagtggtcc agacagaagg ccaagt                46

<210> SEQ ID NO 346
<211> LENGTH: 47
<212> TYPE: DNA
<213> ORGANISM: Artificial Sequence
<220> FEATURE:
<223> OTHER INFORMATION: primer

<400> SEQUENCE: 346
tacaggaggg ctcggcaaaa aaccaagtgg agcagagtcc tcagtcc              47

<210> SEQ ID NO 347
<211> LENGTH: 42
<212> TYPE: DNA
<213> ORGANISM: Artificial Sequence
<220> FEATURE:
<223> OTHER INFORMATION: primer

<400> SEQUENCE: 347
tacaggaggg ctcggcacaa cggaaggagg tggagcagga tc                   42

<210> SEQ ID NO 348
<211> LENGTH: 46
<212> TYPE: DNA
<213> ORGANISM: Artificial Sequence
<220> FEATURE:
<223> OTHER INFORMATION: primer

<400> SEQUENCE: 348
tacaggaggg ctcggcacaa cagaaggagg tggagcagaa ttctgg               46

<210> SEQ ID NO 349
<211> LENGTH: 44
<212> TYPE: DNA
<213> ORGANISM: Artificial Sequence
<220> FEATURE:
<223> OTHER INFORMATION: primer

<400> SEQUENCE: 349
tacaggaggg ctcggcagag aatgtggagc agcatccttc aacc                 44

<210> SEQ ID NO 350
<211> LENGTH: 44
<212> TYPE: DNA
<213> ORGANISM: Artificial Sequence
<220> FEATURE:
<223> OTHER INFORMATION: primer

<400> SEQUENCE: 350
tacaggaggg ctcggcagag agtgtggggc tgcatcttcc tacc                 44

<210> SEQ ID NO 351
<211> LENGTH: 50
<212> TYPE: DNA
<213> ORGANISM: Artificial Sequence
<220> FEATURE:
<223> OTHER INFORMATION: primer

<400> SEQUENCE: 351
tacaggaggg ctcggcacag aagataactc aaacccaacc aggaatgttc           50

<210> SEQ ID NO 352
<211> LENGTH: 43
<212> TYPE: DNA
<213> ORGANISM: Artificial Sequence -continued

```
<220> FEATURE:
<223> OTHER INFORMATION: primer

<400> SEQUENCE: 352
tacaggaggg ctcggcaaat tcagtgaccc agatggaagg gcc                43

<210> SEQ ID NO 353
<211> LENGTH: 44
<212> TYPE: DNA
<213> ORGANISM: Artificial Sequence
<220> FEATURE:
<223> OTHER INFORMATION: primer

<400> SEQUENCE: 353
tacaggaggg ctcggcacaa cagaaggagg tggagcagga tcct               44

<210> SEQ ID NO 354
<211> LENGTH: 43
<212> TYPE: DNA
<213> ORGANISM: Artificial Sequence
<220> FEATURE:
<223> OTHER INFORMATION: primer

<400> SEQUENCE: 354
tacaggaggg ctcggcacag tctgtgaccc agcttgacag cca                43

<210> SEQ ID NO 355
<211> LENGTH: 44
<212> TYPE: DNA
<213> ORGANISM: Artificial Sequence
<220> FEATURE:
<223> OTHER INFORMATION: primer

<400> SEQUENCE: 355
tacaggaggg ctcggcacag agagtgactc agcccgagaa gctc               44

<210> SEQ ID NO 356
<211> LENGTH: 44
<212> TYPE: DNA
<213> ORGANISM: Artificial Sequence
<220> FEATURE:
<223> OTHER INFORMATION: primer

<400> SEQUENCE: 356
tacaggaggg ctcggcacaa cagggagaag aggatcctca ggcc               44

<210> SEQ ID NO 357
<211> LENGTH: 43
<212> TYPE: DNA
<213> ORGANISM: Artificial Sequence
<220> FEATURE:
<223> OTHER INFORMATION: primer

<400> SEQUENCE: 357
tacaggaggg ctcggcagac tcggttaccc agacagaagg ccc                43

<210> SEQ ID NO 358
<211> LENGTH: 50
<212> TYPE: DNA
<213> ORGANISM: Artificial Sequence
<220> FEATURE:
<223> OTHER INFORMATION: primer

<400> SEQUENCE: 358
tacaggaggg ctcggcacag aaggtaactc aagcgcagac tgaaatttct         50
```

```
<210> SEQ ID NO 359
<211> LENGTH: 42
<212> TYPE: DNA
<213> ORGANISM: Artificial Sequence
<220> FEATURE:
<223> OTHER INFORMATION: primer

<400> SEQUENCE: 359
tacaggaggg ctcggcagaa gaccaggtga cgcagagtcc cg          42

<210> SEQ ID NO 360
<211> LENGTH: 43
<212> TYPE: DNA
<213> ORGANISM: Artificial Sequence
<220> FEATURE:
<223> OTHER INFORMATION: primer

<400> SEQUENCE: 360
tacaggaggg ctcggcaaaa caggaggtga cgcagattcc tgc         43

<210> SEQ ID NO 361
<211> LENGTH: 48
<212> TYPE: DNA
<213> ORGANISM: Artificial Sequence
<220> FEATURE:
<223> OTHER INFORMATION: primer

<400> SEQUENCE: 361
tacaggaggg ctcggcaata caagtggagc agagtcctcc agacctga    48

<210> SEQ ID NO 362
<211> LENGTH: 46
<212> TYPE: DNA
<213> ORGANISM: Artificial Sequence
<220> FEATURE:
<223> OTHER INFORMATION: primer

<400> SEQUENCE: 362
tacaggaggg ctcggcacaa cagaaggaga aaagtgacca gcagca      46

<210> SEQ ID NO 363
<211> LENGTH: 49
<212> TYPE: DNA
<213> ORGANISM: Artificial Sequence
<220> FEATURE:
<223> OTHER INFORMATION: primer

<400> SEQUENCE: 363
tacaggaggg ctcggcatac tgaacgtgga acaaagtcct cagtcactg   49

<210> SEQ ID NO 364
<211> LENGTH: 48
<212> TYPE: DNA
<213> ORGANISM: Artificial Sequence
<220> FEATURE:
<223> OTHER INFORMATION: primer

<400> SEQUENCE: 364
tacaggaggg ctcggcacaa caggtaatgc aaattcctca gtaccagc    48

<210> SEQ ID NO 365
<211> LENGTH: 38
<212> TYPE: DNA
<213> ORGANISM: Artificial Sequence
<220> FEATURE:
<223> OTHER INFORMATION: primer

<400> SEQUENCE: 365
```
tacaggaggg ctcggcaaag accacccagc cccctcc         38

<210> SEQ ID NO 366
<211> LENGTH: 41
<212> TYPE: DNA
<213> ORGANISM: Artificial Sequence
<220> FEATURE:
<223> OTHER INFORMATION: primer

<400> SEQUENCE: 366
tacaggaggg ctcggcacag tcggtgaccc agcttgatgg c         41

<210> SEQ ID NO 367
<211> LENGTH: 42
<212> TYPE: DNA
<213> ORGANISM: Artificial Sequence
<220> FEATURE:
<223> OTHER INFORMATION: primer

<400> SEQUENCE: 367
tacaggaggg ctcggcacag ctgctggagc agagccctca gt         42

<210> SEQ ID NO 368
<211> LENGTH: 50
<212> TYPE: DNA
<213> ORGANISM: Artificial Sequence
<220> FEATURE:
<223> OTHER INFORMATION: primer

<400> SEQUENCE: 368
tacaggaggg ctcggcacaa cagaagaatg atgaccagca agttaagcaa         50

<210> SEQ ID NO 369
<211> LENGTH: 44
<212> TYPE: DNA
<213> ORGANISM: Artificial Sequence
<220> FEATURE:
<223> OTHER INFORMATION: primer

<400> SEQUENCE: 369
tacaggaggg ctcggcacaa caaccagtgc agagtcctca agcc         44

<210> SEQ ID NO 370
<211> LENGTH: 49
<212> TYPE: DNA
<213> ORGANISM: Artificial Sequence
<220> FEATURE:
<223> OTHER INFORMATION: primer

<400> SEQUENCE: 370
tacaggaggg ctcggcaaga ccacacagcc aaattcaatg gagagtaac         49

<210> SEQ ID NO 371
<211> LENGTH: 47
<212> TYPE: DNA
<213> ORGANISM: Artificial Sequence
<220> FEATURE:
<223> OTHER INFORMATION: primer

<400> SEQUENCE: 371
tacaggaggg ctcggcacaa gaactggagc agagtcctca gtccttg         47

<210> SEQ ID NO 372
<211> LENGTH: 53
<212> TYPE: DNA
<213> ORGANISM: Artificial Sequence

```
<220> FEATURE:
<223> OTHER INFORMATION: primer

<400> SEQUENCE: 372
tacaggaggg ctcggcacaa cagctgaatc agagtcctca atctatgttt atc        53

<210> SEQ ID NO 373
<211> LENGTH: 49
<212> TYPE: DNA
<213> ORGANISM: Artificial Sequence
<220> FEATURE:
<223> OTHER INFORMATION: primer

<400> SEQUENCE: 373
tacaggaggg ctcggcaaag acaaggtggt acaaagccct ctatctctg             49

<210> SEQ ID NO 374
<211> LENGTH: 49
<212> TYPE: DNA
<213> ORGANISM: Artificial Sequence
<220> FEATURE:
<223> OTHER INFORMATION: primer

<400> SEQUENCE: 374
tacaggaggg ctcggcaaga cagtcactca gtctcaacca gagatgtct             49

<210> SEQ ID NO 375
<211> LENGTH: 47
<212> TYPE: DNA
<213> ORGANISM: Artificial Sequence
<220> FEATURE:
<223> OTHER INFORMATION: primer

<400> SEQUENCE: 375
tacaggaggg ctcggcagag ctgaaagtgg aacaaaaccc tctgttc               47

<210> SEQ ID NO 376
<211> LENGTH: 46
<212> TYPE: DNA
<213> ORGANISM: Artificial Sequence
<220> FEATURE:
<223> OTHER INFORMATION: primer

<400> SEQUENCE: 376
tacaggaggg ctcggcaaat tcagtcaagc agacgggcca aataac                46

<210> SEQ ID NO 377
<211> LENGTH: 45
<212> TYPE: DNA
<213> ORGANISM: Artificial Sequence
<220> FEATURE:
<223> OTHER INFORMATION: primer

<400> SEQUENCE: 377
tacaggaggg ctcggcagcc aaaaatgaag tggagcagag tcctc                 45

<210> SEQ ID NO 378
<211> LENGTH: 42
<212> TYPE: DNA
<213> ORGANISM: Artificial Sequence
<220> FEATURE:
<223> OTHER INFORMATION: primer

<400> SEQUENCE: 378
gtcagggttc tggatatggg gagaagtgga aactctggtt cc                    42
```

-continued

<210> SEQ ID NO 379
<211> LENGTH: 49
<212> TYPE: DNA
<213> ORGANISM: Artificial Sequence
<220> FEATURE:
<223> OTHER INFORMATION: primer

<400> SEQUENCE: 379
gtcagggttc tggatatcag atataatgaa tacatgggtc cctttccca                49

<210> SEQ ID NO 380
<211> LENGTH: 40
<212> TYPE: DNA
<213> ORGANISM: Artificial Sequence
<220> FEATURE:
<223> OTHER INFORMATION: primer

<400> SEQUENCE: 380
gtcagggttc tggatatttg gccggatgct gagtctggtc                40

<210> SEQ ID NO 381
<211> LENGTH: 42
<212> TYPE: DNA
<213> ORGANISM: Artificial Sequence
<220> FEATURE:
<223> OTHER INFORMATION: primer

<400> SEQUENCE: 381
gtcagggttc tggatatatg ggtgtacagc cagcctggtc cc                42

<210> SEQ ID NO 382
<211> LENGTH: 46
<212> TYPE: DNA
<213> ORGANISM: Artificial Sequence
<220> FEATURE:
<223> OTHER INFORMATION: primer

<400> SEQUENCE: 382
gtcagggttc tggatatttg gttgcacttg gagtcttgtt ccactc                46

<210> SEQ ID NO 383
<211> LENGTH: 47
<212> TYPE: DNA
<213> ORGANISM: Artificial Sequence
<220> FEATURE:
<223> OTHER INFORMATION: primer

<400> SEQUENCE: 383
gtcagggttc tggatatacg gatgaacaat aaggctggtt cctcttc                47

<210> SEQ ID NO 384
<211> LENGTH: 45
<212> TYPE: DNA
<213> ORGANISM: Artificial Sequence
<220> FEATURE:
<223> OTHER INFORMATION: primer

<400> SEQUENCE: 384
gtcagggttc tggatatttg gtatgaccac cacttggttc ccctt                45

<210> SEQ ID NO 385
<211> LENGTH: 42
<212> TYPE: DNA
<213> ORGANISM: Artificial Sequence
<220> FEATURE:
<223> OTHER INFORMATION: primer

<400> SEQUENCE: 385
gtcagggttc tggatatttg gactgaccag aagtcgggtg cc                      42

<210> SEQ ID NO 386
<211> LENGTH: 52
<212> TYPE: DNA
<213> ORGANISM: Artificial Sequence
<220> FEATURE:
<223> OTHER INFORMATION: primer

<400> SEQUENCE: 386
gtcagggttc tggatatttg ctttaacaaa tagtcttgtt cctgctccaa ag           52

<210> SEQ ID NO 387
<211> LENGTH: 47
<212> TYPE: DNA
<213> ORGANISM: Artificial Sequence
<220> FEATURE:
<223> OTHER INFORMATION: primer

<400> SEQUENCE: 387
gtcagggttc tggatattga gttccacttt tagctgagtg cctgtcc                 47

<210> SEQ ID NO 388
<211> LENGTH: 48
<212> TYPE: DNA
<213> ORGANISM: Artificial Sequence
<220> FEATURE:
<223> OTHER INFORMATION: primer

<400> SEQUENCE: 388
gtcagggttc tggatatctg gagagactag aagcatagtc cccttccc                48

<210> SEQ ID NO 389
<211> LENGTH: 41
<212> TYPE: DNA
<213> ORGANISM: Artificial Sequence
<220> FEATURE:
<223> OTHER INFORMATION: primer

<400> SEQUENCE: 389
gtcagggttc tggatatcag gcctgaccag cagtctggtc c                       41

<210> SEQ ID NO 390
<211> LENGTH: 45
<212> TYPE: DNA
<213> ORGANISM: Artificial Sequence
<220> FEATURE:
<223> OTHER INFORMATION: primer

<400> SEQUENCE: 390
gtcagggttc tggatatttg ggatgacttg gagctttgtt ccaat                   45

<210> SEQ ID NO 391
<211> LENGTH: 49
<212> TYPE: DNA
<213> ORGANISM: Artificial Sequence
<220> FEATURE:
<223> OTHER INFORMATION: primer

<400> SEQUENCE: 391
gtcagggttc tggatatcag gttttactga taatcttgtc ccactccca               49

<210> SEQ ID NO 392
<211> LENGTH: 47
<212> TYPE: DNA
<213> ORGANISM: Artificial Sequence

```
<220> FEATURE:
<223> OTHER INFORMATION: primer

<400> SEQUENCE: 392
gtcagggttc tggatattgg aactcactga taaggtgggt tcccttc        47

<210> SEQ ID NO 393
<211> LENGTH: 47
<212> TYPE: DNA
<213> ORGANISM: Artificial Sequence
<220> FEATURE:
<223> OTHER INFORMATION: primer

<400> SEQUENCE: 393
gtcagggttc tggatattaa gatccacctt taacatggtt ccccttg        47

<210> SEQ ID NO 394
<211> LENGTH: 47
<212> TYPE: DNA
<213> ORGANISM: Artificial Sequence
<220> FEATURE:
<223> OTHER INFORMATION: primer

<400> SEQUENCE: 394
gtcagggttc tggatatttg gtttaactag caccctggtt cctcctc        47

<210> SEQ ID NO 395
<211> LENGTH: 47
<212> TYPE: DNA
<213> ORGANISM: Artificial Sequence
<220> FEATURE:
<223> OTHER INFORMATION: primer

<400> SEQUENCE: 395
gtcagggttc tggatatcag gccagacagt caactgagtt cctcttc        47

<210> SEQ ID NO 396
<211> LENGTH: 48
<212> TYPE: DNA
<213> ORGANISM: Artificial Sequence
<220> FEATURE:
<223> OTHER INFORMATION: primer

<400> SEQUENCE: 396
gtcagggttc tggatatttg gagtgacatt atgtttggat ccctttcc       48

<210> SEQ ID NO 397
<211> LENGTH: 47
<212> TYPE: DNA
<213> ORGANISM: Artificial Sequence
<220> FEATURE:
<223> OTHER INFORMATION: primer

<400> SEQUENCE: 397
gtcagggttc tggatatttg ctcttacagt tactgtggtt ccggctc        47

<210> SEQ ID NO 398
<211> LENGTH: 48
<212> TYPE: DNA
<213> ORGANISM: Artificial Sequence
<220> FEATURE:
<223> OTHER INFORMATION: primer

<400> SEQUENCE: 398
gtcagggttc tggatatttg gttttacatt gagtttggtc ccagatcc       48
```

```
<210> SEQ ID NO 399
<211> LENGTH: 48
<212> TYPE: DNA
<213> ORGANISM: Artificial Sequence
<220> FEATURE:
<223> OTHER INFORMATION: primer

<400> SEQUENCE: 399
gtcagggttc tggatatcag gtaaaacagt caattgtgtc ccagatcc          48

<210> SEQ ID NO 400
<211> LENGTH: 46
<212> TYPE: DNA
<213> ORGANISM: Artificial Sequence
<220> FEATURE:
<223> OTHER INFORMATION: primer

<400> SEQUENCE: 400
gtcagggttc tggatattgg gtttcacaga taactccgtt ccctgt            46

<210> SEQ ID NO 401
<211> LENGTH: 40
<212> TYPE: DNA
<213> ORGANISM: Artificial Sequence
<220> FEATURE:
<223> OTHER INFORMATION: primer

<400> SEQUENCE: 401
gtcagggttc tggatatctg gggtgaccac aacctgggtc                   40

<210> SEQ ID NO 402
<211> LENGTH: 40
<212> TYPE: DNA
<213> ORGANISM: Artificial Sequence
<220> FEATURE:
<223> OTHER INFORMATION: primer

<400> SEQUENCE: 402
gtcagggttc tggatatctg gggtgaccac aacctgggtc                   40

<210> SEQ ID NO 403
<211> LENGTH: 41
<212> TYPE: DNA
<213> ORGANISM: Artificial Sequence
<220> FEATURE:
<223> OTHER INFORMATION: primer

<400> SEQUENCE: 403
gtcagggttc tggatatagg gcagcacgga caatctggtt c                 41

<210> SEQ ID NO 404
<211> LENGTH: 45
<212> TYPE: DNA
<213> ORGANISM: Artificial Sequence
<220> FEATURE:
<223> OTHER INFORMATION: primer

<400> SEQUENCE: 404
gtcagggttc tggatatttg gcttcacagt gagcgtagtc ccatc             45

<210> SEQ ID NO 405
<211> LENGTH: 45
<212> TYPE: DNA
<213> ORGANISM: Artificial Sequence
<220> FEATURE:
<223> OTHER INFORMATION: primer

<400> SEQUENCE: 405
```
gtcagggttc tggatatttg gtatgaccga gagtttggtc ccctt 45

<210> SEQ ID NO 406
<211> LENGTH: 47
<212> TYPE: DNA
<213> ORGANISM: Artificial Sequence
<220> FEATURE:
<223> OTHER INFORMATION: primer

<400> SEQUENCE: 406
gtcagggttc tggatatttg caatcacaga aagtcttgtg cccttc 47

<210> SEQ ID NO 407
<211> LENGTH: 47
<212> TYPE: DNA
<213> ORGANISM: Artificial Sequence
<220> FEATURE:
<223> OTHER INFORMATION: primer

<400> SEQUENCE: 407
gtcagggttc tggatattgg ggagaatatg aagtcgtgtc cctttc 47

<210> SEQ ID NO 408
<211> LENGTH: 41
<212> TYPE: DNA
<213> ORGANISM: Artificial Sequence
<220> FEATURE:
<223> OTHER INFORMATION: primer

<400> SEQUENCE: 408
gtcagggttc tggatattgg gcttcaccac cagctgagtt c 41

<210> SEQ ID NO 409
<211> LENGTH: 41
<212> TYPE: DNA
<213> ORGANISM: Artificial Sequence
<220> FEATURE:
<223> OTHER INFORMATION: primer

<400> SEQUENCE: 409
gtcagggttc tggatatttg gctggacagc aagcagagtg c 41

<210> SEQ ID NO 410
<211> LENGTH: 46
<212> TYPE: DNA
<213> ORGANISM: Artificial Sequence
<220> FEATURE:
<223> OTHER INFORMATION: primer

<400> SEQUENCE: 410
gtcagggttc tggatatctg gctttataat tagcttggtc ccagcg 46

<210> SEQ ID NO 411
<211> LENGTH: 47
<212> TYPE: DNA
<213> ORGANISM: Artificial Sequence
<220> FEATURE:
<223> OTHER INFORMATION: primer

<400> SEQUENCE: 411
gtcagggttc tggatatttg gaaagacttg taatctggtc ccagtcc 47

<210> SEQ ID NO 412
<211> LENGTH: 46
<212> TYPE: DNA
<213> ORGANISM: Artificial Sequence

```
<220> FEATURE:
<223> OTHER INFORMATION: primer

<400> SEQUENCE: 412
gtcagggttc tggatatgtg gtaaaacaat cacttgagtg ccggac         46

<210> SEQ ID NO 413
<211> LENGTH: 46
<212> TYPE: DNA
<213> ORGANISM: Artificial Sequence
<220> FEATURE:
<223> OTHER INFORMATION: primer

<400> SEQUENCE: 413
gtcagggttc tggatatagg ggaataacgg tgagtctcgt tccagt         46

<210> SEQ ID NO 414
<211> LENGTH: 48
<212> TYPE: DNA
<213> ORGANISM: Artificial Sequence
<220> FEATURE:
<223> OTHER INFORMATION: primer

<400> SEQUENCE: 414
gtcagggttc tggatatctg gttttacttg gtaaagttgt cccttgcc       48

<210> SEQ ID NO 415
<211> LENGTH: 43
<212> TYPE: DNA
<213> ORGANISM: Artificial Sequence
<220> FEATURE:
<223> OTHER INFORMATION: primer

<400> SEQUENCE: 415
gtcagggttc tggatattcg gatttactgc caggcttgtt ccc            43

<210> SEQ ID NO 416
<211> LENGTH: 44
<212> TYPE: DNA
<213> ORGANISM: Artificial Sequence
<220> FEATURE:
<223> OTHER INFORMATION: primer

<400> SEQUENCE: 416
gtcagggttc tggatatggg gtttgaccat taaccttgtt cccc           44

<210> SEQ ID NO 417
<211> LENGTH: 44
<212> TYPE: DNA
<213> ORGANISM: Artificial Sequence
<220> FEATURE:
<223> OTHER INFORMATION: primer

<400> SEQUENCE: 417
gtcagggttc tggatatttg ctaaaacctt cagcctggtg cctg           44

<210> SEQ ID NO 418
<211> LENGTH: 40
<212> TYPE: DNA
<213> ORGANISM: Artificial Sequence
<220> FEATURE:
<223> OTHER INFORMATION: primer

<400> SEQUENCE: 418
gtcagggttc tggatatggg gtgtgaccaa cagcgaggtg               40
```

<210> SEQ ID NO 419
<211> LENGTH: 53
<212> TYPE: DNA
<213> ORGANISM: Artificial Sequence
<220> FEATURE:
<223> OTHER INFORMATION: primer

<400> SEQUENCE: 419
gtcagggttc tggatatttg gtttaacaga gagtttagtg cctttccaa aga                53

<210> SEQ ID NO 420
<211> LENGTH: 47
<212> TYPE: DNA
<213> ORGANISM: Artificial Sequence
<220> FEATURE:
<223> OTHER INFORMATION: primer

<400> SEQUENCE: 420
gtcagggttc tggatatttg gttttactgt cagtctggtc cctgctc                      47

<210> SEQ ID NO 421
<211> LENGTH: 45
<212> TYPE: DNA
<213> ORGANISM: Artificial Sequence
<220> FEATURE:
<223> OTHER INFORMATION: primer

<400> SEQUENCE: 421
gtcagggttc tggatatcga gcgtgacctg aagtcttgtt ccagt                        45

<210> SEQ ID NO 422
<211> LENGTH: 46
<212> TYPE: DNA
<213> ORGANISM: Artificial Sequence
<220> FEATURE:
<223> OTHER INFORMATION: primer

<400> SEQUENCE: 422
gtcagggttc tggatatagg gctggatgat tagatgagtc cctttg                       46

<210> SEQ ID NO 423
<211> LENGTH: 43
<212> TYPE: DNA
<213> ORGANISM: Artificial Sequence
<220> FEATURE:
<223> OTHER INFORMATION: primer

<400> SEQUENCE: 423
gtcagggttc tggatattgg gcctaactgc taaacgagtc ccg                          43

<210> SEQ ID NO 424
<211> LENGTH: 46
<212> TYPE: DNA
<213> ORGANISM: Artificial Sequence
<220> FEATURE:
<223> OTHER INFORMATION: primer

<400> SEQUENCE: 424
gtcagggttc tggatatagg acttgactct cagaatggtt cctgcg                       46

<210> SEQ ID NO 425
<211> LENGTH: 47
<212> TYPE: DNA
<213> ORGANISM: Artificial Sequence
<220> FEATURE:
<223> OTHER INFORMATION: primer

<400> SEQUENCE: 425

```
gtcagggttc tggatattgg gtatgatggt gagtcttgtt ccagtcc            47
```

<210> SEQ ID NO 426
<211> LENGTH: 45
<212> TYPE: DNA
<213> ORGANISM: Artificial Sequence
<220> FEATURE:
<223> OTHER INFORMATION: primer

<400> SEQUENCE: 426

```
gtcagggttc tggatatttg gaatgaccgt caaacttgtc cctgt              45
```

<210> SEQ ID NO 427
<211> LENGTH: 46
<212> TYPE: DNA
<213> ORGANISM: Artificial Sequence
<220> FEATURE:
<223> OTHER INFORMATION: primer

<400> SEQUENCE: 427

```
gtcagggttc tggatatttg gaatgactga taagcttgtc cctggc             46
```

<210> SEQ ID NO 428
<211> LENGTH: 48
<212> TYPE: DNA
<213> ORGANISM: Artificial Sequence
<220> FEATURE:
<223> OTHER INFORMATION: primer

<400> SEQUENCE: 428

```
gtcagggttc tggatatttg gcttcacagt tagtcatgtc tcctttcc           48
```

<210> SEQ ID NO 429
<211> LENGTH: 45
<212> TYPE: DNA
<213> ORGANISM: Artificial Sequence
<220> FEATURE:
<223> OTHER INFORMATION: primer

<400> SEQUENCE: 429

```
gtcagggttc tggatatttg gatggacagt caagatggtc ccttg              45
```

<210> SEQ ID NO 430
<211> LENGTH: 48
<212> TYPE: DNA
<213> ORGANISM: Artificial Sequence
<220> FEATURE:
<223> OTHER INFORMATION: primer

<400> SEQUENCE: 430

```
gtcagggttc tggatatttg gattcacggt taagagagtt cctttttcc          48
```

<210> SEQ ID NO 431
<211> LENGTH: 45
<212> TYPE: DNA
<213> ORGANISM: Artificial Sequence
<220> FEATURE:
<223> OTHER INFORMATION: primer

<400> SEQUENCE: 431

```
gtcagggttc tggatatttg ggttgatagt cagcctggtt ccttg              45
```

<210> SEQ ID NO 432
<211> LENGTH: 49
<212> TYPE: DNA
<213> ORGANISM: Artificial Sequence

```
<220> FEATURE:
<223> OTHER INFORMATION: primer

<400> SEQUENCE: 432
gtcagggttc tggatatttg gatttatttt tgtactcatc cccttccc                    49

<210> SEQ ID NO 433
<211> LENGTH: 55
<212> TYPE: DNA
<213> ORGANISM: Artificial Sequence
<220> FEATURE:
<223> OTHER INFORMATION: primer

<400> SEQUENCE: 433
gtcagggttc tggatatctg gtctaacact cagagttatt ccttttccaa atgtc           55

<210> SEQ ID NO 434
<211> LENGTH: 48
<212> TYPE: DNA
<213> ORGANISM: Artificial Sequence
<220> FEATURE:
<223> OTHER INFORMATION: primer

<400> SEQUENCE: 434
gtcagggttc tggatatatg ggtttactgt cagtttcgtt ccctttcc                    48

<210> SEQ ID NO 435
<211> LENGTH: 46
<212> TYPE: DNA
<213> ORGANISM: Artificial Sequence
<220> FEATURE:
<223> OTHER INFORMATION: primer

<400> SEQUENCE: 435
gtcagggttc tggatatcag gattcactgt gagctgtgtt ccttcc                      46

<210> SEQ ID NO 436
<211> LENGTH: 42
<212> TYPE: DNA
<213> ORGANISM: Artificial Sequence
<220> FEATURE:
<223> OTHER INFORMATION: primer

<400> SEQUENCE: 436
gtcagggttc tggatattca ctctcacttg cgtccccatt cc                          42

<210> SEQ ID NO 437
<211> LENGTH: 46
<212> TYPE: DNA
<213> ORGANISM: Artificial Sequence
<220> FEATURE:
<223> OTHER INFORMATION: primer

<400> SEQUENCE: 437
gtcagggttc tggatatcca ggctcacaat taactcagtc cccttc                      46

<210> SEQ ID NO 438
<211> LENGTH: 48
<212> TYPE: DNA
<213> ORGANISM: Artificial Sequence
<220> FEATURE:
<223> OTHER INFORMATION: primer

<400> SEQUENCE: 438
gtcagggttc tggatattga gtttcatgat tcctctagtg ttggctcc                    48
```

```
<210> SEQ ID NO 439
<211> LENGTH: 42
<212> TYPE: DNA
<213> ORGANISM: Artificial Sequence
<220> FEATURE:
<223> OTHER INFORMATION: primer

<400> SEQUENCE: 439
caagagggct cggcagaacc tgaagtcacc cagactccca gc                42

<210> SEQ ID NO 440
<211> LENGTH: 45
<212> TYPE: DNA
<213> ORGANISM: Artificial Sequence
<220> FEATURE:
<223> OTHER INFORMATION: primer

<400> SEQUENCE: 440
caagagggct cggcagctgt ttcccagact ccaaaatacc tggtc             45

<210> SEQ ID NO 441
<211> LENGTH: 45
<212> TYPE: DNA
<213> ORGANISM: Artificial Sequence
<220> FEATURE:
<223> OTHER INFORMATION: primer

<400> SEQUENCE: 441
caagagggct cggcagaagt tacccagaca ccaaaacacc tggtc             45

<210> SEQ ID NO 442
<211> LENGTH: 50
<212> TYPE: DNA
<213> ORGANISM: Artificial Sequence
<220> FEATURE:
<223> OTHER INFORMATION: primer

<400> SEQUENCE: 442
caagagggct cggcaggagt cactcaaact ccaagatatc tgatcaaaac        50

<210> SEQ ID NO 443
<211> LENGTH: 42
<212> TYPE: DNA
<213> ORGANISM: Artificial Sequence
<220> FEATURE:
<223> OTHER INFORMATION: primer

<400> SEQUENCE: 443
caagagggct cggcaggtgt cactcagacc ccaaaattcc ag                42

<210> SEQ ID NO 444
<211> LENGTH: 43
<212> TYPE: DNA
<213> ORGANISM: Artificial Sequence
<220> FEATURE:
<223> OTHER INFORMATION: primer

<400> SEQUENCE: 444
caagagggct cggcaggagt ctcccagtcc ctgagacaca agg               43

<210> SEQ ID NO 445
<211> LENGTH: 43
<212> TYPE: DNA
<213> ORGANISM: Artificial Sequence
<220> FEATURE:
<223> OTHER INFORMATION: primer
```

-continued

<400> SEQUENCE: 445
caagagggct cggcaggagt tacgcagaca ccaagacacc tgg       43

<210> SEQ ID NO 446
<211> LENGTH: 41
<212> TYPE: DNA
<213> ORGANISM: Artificial Sequence
<220> FEATURE:
<223> OTHER INFORMATION: primer

<400> SEQUENCE: 446
caagagggct cggcaggtgt cactcagacc ccaaaattcc g         41

<210> SEQ ID NO 447
<211> LENGTH: 43
<212> TYPE: DNA
<213> ORGANISM: Artificial Sequence
<220> FEATURE:
<223> OTHER INFORMATION: primer

<400> SEQUENCE: 447
caagagggct cggcaggagt tacgcagaca ccaagacacc tgg       43

<210> SEQ ID NO 448
<211> LENGTH: 41
<212> TYPE: DNA
<213> ORGANISM: Artificial Sequence
<220> FEATURE:
<223> OTHER INFORMATION: primer

<400> SEQUENCE: 448
caagagggct cggcaggtgt cactcagacc ccaaaattcc g         41

<210> SEQ ID NO 449
<211> LENGTH: 42
<212> TYPE: DNA
<213> ORGANISM: Artificial Sequence
<220> FEATURE:
<223> OTHER INFORMATION: primer

<400> SEQUENCE: 449
caagagggct cggcaggagt ctcccagtcc cccagtaaca ag        42

<210> SEQ ID NO 450
<211> LENGTH: 40
<212> TYPE: DNA
<213> ORGANISM: Artificial Sequence
<220> FEATURE:
<223> OTHER INFORMATION: primer

<400> SEQUENCE: 450
caagagggct cggcagggat cacccaggca ccaacatctc          40

<210> SEQ ID NO 451
<211> LENGTH: 42
<212> TYPE: DNA
<213> ORGANISM: Artificial Sequence
<220> FEATURE:
<223> OTHER INFORMATION: primer

<400> SEQUENCE: 451
caagagggct cggcaggagt ctcccagacc cccagtaaca ag        42

```
<210> SEQ ID NO 452
<211> LENGTH: 41
<212> TYPE: DNA
<213> ORGANISM: Artificial Sequence
<220> FEATURE:
<223> OTHER INFORMATION: primer

<400> SEQUENCE: 452
caagagggct cggcaggagt cacccaaagt cccacacacc t                  41

<210> SEQ ID NO 453
<211> LENGTH: 41
<212> TYPE: DNA
<213> ORGANISM: Artificial Sequence
<220> FEATURE:
<223> OTHER INFORMATION: primer

<400> SEQUENCE: 453
caagagggct cggcaggagt cacacaaacc ccaaagcacc t                  41

<210> SEQ ID NO 454
<211> LENGTH: 43
<212> TYPE: DNA
<213> ORGANISM: Artificial Sequence
<220> FEATURE:
<223> OTHER INFORMATION: primer

<400> SEQUENCE: 454
caagagggct cggcagaaat cacccagagc ccaagacaca aga                43

<210> SEQ ID NO 455
<211> LENGTH: 46
<212> TYPE: DNA
<213> ORGANISM: Artificial Sequence
<220> FEATURE:
<223> OTHER INFORMATION: primer

<400> SEQUENCE: 455
caagagggct cggcagaagt tgcccagtcc cccagatata agatta             46

<210> SEQ ID NO 456
<211> LENGTH: 44
<212> TYPE: DNA
<213> ORGANISM: Artificial Sequence
<220> FEATURE:
<223> OTHER INFORMATION: primer

<400> SEQUENCE: 456
caagagggct cggcaggaat cacccagagc ccaagataca agat               44

<210> SEQ ID NO 457
<211> LENGTH: 51
<212> TYPE: DNA
<213> ORGANISM: Artificial Sequence
<220> FEATURE:
<223> OTHER INFORMATION: primer

<400> SEQUENCE: 457
caagagggct cggcaggagt tgcccagtct cccagatata agattataga g       51

<210> SEQ ID NO 458
<211> LENGTH: 42
<212> TYPE: DNA
<213> ORGANISM: Artificial Sequence
<220> FEATURE:
<223> OTHER INFORMATION: primer
```

<400> SEQUENCE: 458
caagagggct cggcaggtgt cactcagacc ccaaaattcc ag    42

<210> SEQ ID NO 459
<211> LENGTH: 43
<212> TYPE: DNA
<213> ORGANISM: Artificial Sequence
<220> FEATURE:
<223> OTHER INFORMATION: primer

<400> SEQUENCE: 459
caagagggct cggcaggagt ctcccagtcc ccaaggtaca aag    43

<210> SEQ ID NO 460
<211> LENGTH: 41
<212> TYPE: DNA
<213> ORGANISM: Artificial Sequence
<220> FEATURE:
<223> OTHER INFORMATION: primer

<400> SEQUENCE: 460
caagagggct cggcaggagt cacccaaagt cccacacacc t    41

<210> SEQ ID NO 461
<211> LENGTH: 41
<212> TYPE: DNA
<213> ORGANISM: Artificial Sequence
<220> FEATURE:
<223> OTHER INFORMATION: primer

<400> SEQUENCE: 461
caagagggct cggcaggtgt cactcagacc ccaaaattcc g    41

<210> SEQ ID NO 462
<211> LENGTH: 41
<212> TYPE: DNA
<213> ORGANISM: Artificial Sequence
<220> FEATURE:
<223> OTHER INFORMATION: primer

<400> SEQUENCE: 462
caagagggct cggcaggagt ctcccagtcc ccaaggtacg a    41

<210> SEQ ID NO 463
<211> LENGTH: 41
<212> TYPE: DNA
<213> ORGANISM: Artificial Sequence
<220> FEATURE:
<223> OTHER INFORMATION: primer

<400> SEQUENCE: 463
caagagggct cggcaggagt cacccaaagt cccacacacc t    41

<210> SEQ ID NO 464
<211> LENGTH: 42
<212> TYPE: DNA
<213> ORGANISM: Artificial Sequence
<220> FEATURE:
<223> OTHER INFORMATION: primer

<400> SEQUENCE: 464
caagagggct cggcaggtgt cactcagacc ccaaaattcc ac    42

```
<210> SEQ ID NO 465
<211> LENGTH: 45
<212> TYPE: DNA
<213> ORGANISM: Artificial Sequence
<220> FEATURE:
<223> OTHER INFORMATION: primer

<400> SEQUENCE: 465
caagagggct cggcaggagt ctcccagtct cccaggtaca aagtc          45

<210> SEQ ID NO 466
<211> LENGTH: 41
<212> TYPE: DNA
<213> ORGANISM: Artificial Sequence
<220> FEATURE:
<223> OTHER INFORMATION: primer

<400> SEQUENCE: 466
caagagggct cggcaggagt cacccaaagt cccacacacc t              41

<210> SEQ ID NO 467
<211> LENGTH: 44
<212> TYPE: DNA
<213> ORGANISM: Artificial Sequence
<220> FEATURE:
<223> OTHER INFORMATION: primer

<400> SEQUENCE: 467
caagagggct cggcaggtgt cactcagacc ccaaaattcc acat           44

<210> SEQ ID NO 468
<211> LENGTH: 45
<212> TYPE: DNA
<213> ORGANISM: Artificial Sequence
<220> FEATURE:
<223> OTHER INFORMATION: primer

<400> SEQUENCE: 468
caagagggct cggcaggagt ctcccagtct cccaggtaca aagtc          45

<210> SEQ ID NO 469
<211> LENGTH: 41
<212> TYPE: DNA
<213> ORGANISM: Artificial Sequence
<220> FEATURE:
<223> OTHER INFORMATION: primer

<400> SEQUENCE: 469
caagagggct cggcaggagt cacccaaagt cccacacacc t              41

<210> SEQ ID NO 470
<211> LENGTH: 44
<212> TYPE: DNA
<213> ORGANISM: Artificial Sequence
<220> FEATURE:
<223> OTHER INFORMATION: primer

<400> SEQUENCE: 470
caagagggct cggcaggtgt cactcagacc ccaaaattcc acat           44

<210> SEQ ID NO 471
<211> LENGTH: 45
<212> TYPE: DNA
<213> ORGANISM: Artificial Sequence
<220> FEATURE:
<223> OTHER INFORMATION: primer
```

<400> SEQUENCE: 471
caagagggct cggcaggagt ctcccagtcc cctaggtaca aagtc  45

<210> SEQ ID NO 472
<211> LENGTH: 43
<212> TYPE: DNA
<213> ORGANISM: Artificial Sequence
<220> FEATURE:
<223> OTHER INFORMATION: primer

<400> SEQUENCE: 472
caagagggct cggcaggagt cacacaaagt cccacacacc tga  43

<210> SEQ ID NO 473
<211> LENGTH: 42
<212> TYPE: DNA
<213> ORGANISM: Artificial Sequence
<220> FEATURE:
<223> OTHER INFORMATION: primer

<400> SEQUENCE: 473
caagagggct cggcaggagt ctcccagaac cccagacaca ag  42

<210> SEQ ID NO 474
<211> LENGTH: 44
<212> TYPE: DNA
<213> ORGANISM: Artificial Sequence
<220> FEATURE:
<223> OTHER INFORMATION: primer

<400> SEQUENCE: 474
caagagggct cggcaggagt catccagtcc ccaagacatc tgat  44

<210> SEQ ID NO 475
<211> LENGTH: 42
<212> TYPE: DNA
<213> ORGANISM: Artificial Sequence
<220> FEATURE:
<223> OTHER INFORMATION: primer

<400> SEQUENCE: 475
caagagggct cggcaggaat cacccagagc ccaagacaca ag  42

<210> SEQ ID NO 476
<211> LENGTH: 53
<212> TYPE: DNA
<213> ORGANISM: Artificial Sequence
<220> FEATURE:
<223> OTHER INFORMATION: primer

<400> SEQUENCE: 476
caagagggct cggcaggagt ggttcagtct cccagatata agattataga gaa  53

<210> SEQ ID NO 477
<211> LENGTH: 40
<212> TYPE: DNA
<213> ORGANISM: Artificial Sequence
<220> FEATURE:
<223> OTHER INFORMATION: primer

<400> SEQUENCE: 477
caagagggct cggcaggagt tatccagtca ccccgccatg  40

```
<210> SEQ ID NO 478
<211> LENGTH: 39
<212> TYPE: DNA
<213> ORGANISM: Artificial Sequence
<220> FEATURE:
<223> OTHER INFORMATION: primer

<400> SEQUENCE: 478
caagagggct cggcaggagt tatccagtca ccccggcac                          39

<210> SEQ ID NO 479
<211> LENGTH: 42
<212> TYPE: DNA
<213> ORGANISM: Artificial Sequence
<220> FEATURE:
<223> OTHER INFORMATION: primer

<400> SEQUENCE: 479
caagagggct cggcaagagt cacccagaca ccaaggcaca ag                      42

<210> SEQ ID NO 480
<211> LENGTH: 42
<212> TYPE: DNA
<213> ORGANISM: Artificial Sequence
<220> FEATURE:
<223> OTHER INFORMATION: primer

<400> SEQUENCE: 480
caagagggct cggcaggagt tactcagttc cccagccaca gc                      42

<210> SEQ ID NO 481
<211> LENGTH: 45
<212> TYPE: DNA
<213> ORGANISM: Artificial Sequence
<220> FEATURE:
<223> OTHER INFORMATION: primer

<400> SEQUENCE: 481
caagagggct cggcaatggt catccagaac ccaagatacc aggtt                   45

<210> SEQ ID NO 482
<211> LENGTH: 38
<212> TYPE: DNA
<213> ORGANISM: Artificial Sequence
<220> FEATURE:
<223> OTHER INFORMATION: primer

<400> SEQUENCE: 482
caagagggct cggcagagcc tggagtcagc cagacccc                           38

<210> SEQ ID NO 483
<211> LENGTH: 39
<212> TYPE: DNA
<213> ORGANISM: Artificial Sequence
<220> FEATURE:
<223> OTHER INFORMATION: primer

<400> SEQUENCE: 483
caagagggct cggcaggcgt catgcagaac ccaagacac                          39

<210> SEQ ID NO 484
<211> LENGTH: 46
<212> TYPE: DNA
<213> ORGANISM: Artificial Sequence
<220> FEATURE:
<223> OTHER INFORMATION: primer
```

```
<400> SEQUENCE: 484
caagagggct cggcaggaat cactcagtcc ccaaagtacc tgttca         46

<210> SEQ ID NO 485
<211> LENGTH: 41
<212> TYPE: DNA
<213> ORGANISM: Artificial Sequence
<220> FEATURE:
<223> OTHER INFORMATION: primer

<400> SEQUENCE: 485
caagagggct cggcagctgt cgtctctcaa catccgagct g              41

<210> SEQ ID NO 486
<211> LENGTH: 39
<212> TYPE: DNA
<213> ORGANISM: Artificial Sequence
<220> FEATURE:
<223> OTHER INFORMATION: primer

<400> SEQUENCE: 486
caagagggct cggcaattcc agctcactgg ggctggatg                 39

<210> SEQ ID NO 487
<211> LENGTH: 46
<212> TYPE: DNA
<213> ORGANISM: Artificial Sequence
<220> FEATURE:
<223> OTHER INFORMATION: primer

<400> SEQUENCE: 487
caagagggct cggcaaaagt cacacagact ccaggacatt tggtca         46

<210> SEQ ID NO 488
<211> LENGTH: 45
<212> TYPE: DNA
<213> ORGANISM: Artificial Sequence
<220> FEATURE:
<223> OTHER INFORMATION: primer

<400> SEQUENCE: 488
caagagggct cggcagatgt tacccagacc ccaaggaata ggatc          45

<210> SEQ ID NO 489
<211> LENGTH: 50
<212> TYPE: DNA
<213> ORGANISM: Artificial Sequence
<220> FEATURE:
<223> OTHER INFORMATION: primer

<400> SEQUENCE: 489
caagagggct cggcagacat ctaccagacc ccaagatacc ttgttatagg     50

<210> SEQ ID NO 490
<211> LENGTH: 50
<212> TYPE: DNA
<213> ORGANISM: Artificial Sequence
<220> FEATURE:
<223> OTHER INFORMATION: primer

<400> SEQUENCE: 490
caagagggct cggcagtagt tacacaattc ccaagacaca gaatcattgg     50
```

```
<210> SEQ ID NO 491
<211> LENGTH: 45
<212> TYPE: DNA
<213> ORGANISM: Artificial Sequence
<220> FEATURE:
<223> OTHER INFORMATION: primer

<400> SEQUENCE: 491
caagagggct cggcacaagt gacccagaac ccaagatacc tcatc            45

<210> SEQ ID NO 492
<211> LENGTH: 48
<212> TYPE: DNA
<213> ORGANISM: Artificial Sequence
<220> FEATURE:
<223> OTHER INFORMATION: primer

<400> SEQUENCE: 492
caagagggct cggcatcgag atatctagtc aaaaggacgg gagagaaa         48

<210> SEQ ID NO 493
<211> LENGTH: 42
<212> TYPE: DNA
<213> ORGANISM: Artificial Sequence
<220> FEATURE:
<223> OTHER INFORMATION: primer

<400> SEQUENCE: 493
caagagggct cggcagctgt catctctcaa aagccaagca gg               42

<210> SEQ ID NO 494
<211> LENGTH: 50
<212> TYPE: DNA
<213> ORGANISM: Artificial Sequence
<220> FEATURE:
<223> OTHER INFORMATION: primer

<400> SEQUENCE: 494
aacaccttgt tcaggtcctc tacaactgtg agtctggtgc cttgtccaaa       50

<210> SEQ ID NO 495
<211> LENGTH: 46
<212> TYPE: DNA
<213> ORGANISM: Artificial Sequence
<220> FEATURE:
<223> OTHER INFORMATION: primer

<400> SEQUENCE: 495
aacaccttgt tcaggtcctc tacaacggtt aacctggtcc ccgaac           46

<210> SEQ ID NO 496
<211> LENGTH: 49
<212> TYPE: DNA
<213> ORGANISM: Artificial Sequence
<220> FEATURE:
<223> OTHER INFORMATION: primer

<400> SEQUENCE: 496
aacaccttgt tcaggtcctc tacaacagtg agccaacttc cctctccaa        49

<210> SEQ ID NO 497
<211> LENGTH: 46
<212> TYPE: DNA
<213> ORGANISM: Artificial Sequence
<220> FEATURE:
<223> OTHER INFORMATION: primer
```

```
<400> SEQUENCE: 497
aacaccttgt tcaggtcctc caagacagag agctgggttc cactgc          46

<210> SEQ ID NO 498
<211> LENGTH: 48
<212> TYPE: DNA
<213> ORGANISM: Artificial Sequence
<220> FEATURE:
<223> OTHER INFORMATION: primer

<400> SEQUENCE: 498
aacaccttgt tcaggtcctc taggatggag agtcgagtcc catcacca        48

<210> SEQ ID NO 499
<211> LENGTH: 45
<212> TYPE: DNA
<213> ORGANISM: Artificial Sequence
<220> FEATURE:
<223> OTHER INFORMATION: primer

<400> SEQUENCE: 499
aacaccttgt tcaggtcctc tgtcacagtg agcctggtcc cgttc           45

<210> SEQ ID NO 500
<211> LENGTH: 43
<212> TYPE: DNA
<213> ORGANISM: Artificial Sequence
<220> FEATURE:
<223> OTHER INFORMATION: primer

<400> SEQUENCE: 500
aacaccttgt tcaggtcctc tagcacggtg agccgtgtcc ctg             43

<210> SEQ ID NO 501
<211> LENGTH: 47
<212> TYPE: DNA
<213> ORGANISM: Artificial Sequence
<220> FEATURE:
<223> OTHER INFORMATION: primer

<400> SEQUENCE: 501
aacaccttgt tcaggtcctc cagtacggtc agcctagagc cttctcc         47

<210> SEQ ID NO 502
<211> LENGTH: 42
<212> TYPE: DNA
<213> ORGANISM: Artificial Sequence
<220> FEATURE:
<223> OTHER INFORMATION: primer

<400> SEQUENCE: 502
aacaccttgt tcaggtcctc cagaaccagg agtcctccgc cc              42

<210> SEQ ID NO 503
<211> LENGTH: 40
<212> TYPE: DNA
<213> ORGANISM: Artificial Sequence
<220> FEATURE:
<223> OTHER INFORMATION: primer

<400> SEQUENCE: 503
aacaccttgt tcaggtcctc gagcactgtc agccgggtgc                 40
```

```
<210> SEQ ID NO 504
<211> LENGTH: 41
<212> TYPE: DNA
<213> ORGANISM: Artificial Sequence
<220> FEATURE:
<223> OTHER INFORMATION: primer

<400> SEQUENCE: 504
aacaccttgt tcaggtcctc cagcactgag agccgggtcc c         41

<210> SEQ ID NO 505
<211> LENGTH: 39
<212> TYPE: DNA
<213> ORGANISM: Artificial Sequence
<220> FEATURE:
<223> OTHER INFORMATION: primer

<400> SEQUENCE: 505
aacaccttgt tcaggtcctc gagcaccagg agccgcgtg           39

<210> SEQ ID NO 506
<211> LENGTH: 40
<212> TYPE: DNA
<213> ORGANISM: Artificial Sequence
<220> FEATURE:
<223> OTHER INFORMATION: primer

<400> SEQUENCE: 506
aacaccttgt tcaggtcctc cagcacggtc agcctgctgc           40

<210> SEQ ID NO 507
<211> LENGTH: 41
<212> TYPE: DNA
<213> ORGANISM: Artificial Sequence
<220> FEATURE:
<223> OTHER INFORMATION: primer

<400> SEQUENCE: 507
aacaccttgt tcaggtcctc tgtgaccgtg agcctggtgc c         41

<210> SEQ ID NO 508
<211> LENGTH: 23
<212> TYPE: DNA
<213> ORGANISM: Artificial Sequence
<220> FEATURE:
<223> OTHER INFORMATION: primer

<400> SEQUENCE: 508
cgtggttaca ggagggctcg gca                            23

<210> SEQ ID NO 509
<211> LENGTH: 26
<212> TYPE: DNA
<213> ORGANISM: Artificial Sequence
<220> FEATURE:
<223> OTHER INFORMATION: primer

<400> SEQUENCE: 509
cacggcaggg tcagggttct ggatat                         26

<210> SEQ ID NO 510
<211> LENGTH: 21
<212> TYPE: DNA
<213> ORGANISM: Artificial Sequence
<220> FEATURE:
<223> OTHER INFORMATION: primer
```

-continued

```
<400> SEQUENCE: 510
tggctccaag agggctcggc a                                              21

<210> SEQ ID NO 511
<211> LENGTH: 26
<212> TYPE: DNA
<213> ORGANISM: Artificial Sequence
<220> FEATURE:
<223> OTHER INFORMATION: primer

<400> SEQUENCE: 511
gggtgggaac accttgttca ggtcct                                         26
```

ISOLATION OF UNKNOWN REARRANGED T-CELL RECEPTORS FROM SINGLE CELLS

CROSS-REFERENCE TO RELATED APPLICATIONS

The present application claims priority to U.S. Provisional Application No. 61/221,505, filed Jun. 29, 2009, which is incorporated by reference herein.

REFERENCE TO SEQUENCE LISTING, TABLE, OR COMPUTER PROGRAM LISTING

The present application is being filed along with a Sequence Listing in electronic format. The Sequence Listing is provided as a file entitled Sequence_Listing-CALTE062A.txt, created Jun. 24, 2010, which is 85,981 bytes in size. The information in the electronic format of the Sequence Listing is incorporated herein by reference in its entirety.

BACKGROUND OF THE INVENTION

Field of the Invention

The human immune system is comprised of innate and adaptive mechanisms that clear foreign particles from the body. The adaptive immune response includes the humoral response, which involves B lymphocytes and antibody secretion, and a cell-mediated response, which involves T lymphocytes. The cell-mediated immune response functions by activating macrophages, natural killer cells, and CD8+ cytotoxic T-lymphocytes (CTLs) that act to destroy pathogens, as well as CD4+ helper T-cells that activate the humoral immune response. The specificity of the cell-mediated response comes from the T-cell receptors (TCRs) found on the T-cell surface. These TCRs recognize a specific combination of antigen and major histocompatibility complex (MHC) molecules and trigger T-cell function. TCR recognition on CD8+ CTLs can lead to the induction of apoptosis of the target cell, and the initiation of the humoral immune response from CD4+ T-helper cells.

A single TCR consists of two unique peptide chains (alpha and beta), each of which is produced by a genomic recombination of two segments known as variable and joining regions (V and J, respectively). A TCR includes one of 44 alpha variable (V) regions, 76 alpha junctional (J) regions, 54 beta V regions, and 14 beta J regions. Thus, amplification of this region is complex, and requires at least 188 unique oligonucleotides. There are 3344 different alpha chain combinations and 216 beta combinations, leading to 722,304 possible chain pairings. This diversity is greatly amplified by additional mutagenesis occurring from DNA repair following the RAG1-RAG2 recombination process. As a consequence, simply identifying the different V and J regions is not sufficient information to isolate a functional TCR.

This complexity and variability make difficult the isolation of an unknown TCR from an inhomogeneous population of cells. Isolation of the TCR from a single cell has been suggested as a high throughput solution to the problem of alpha-beta mispairing. However, unlike plasma cells, T-cells do not express high transcript levels of TCR, making it difficult to isolate sufficient cDNA template for reliable amplification.

Because there are 722,304 possible chain pairings, previous protocols have not permitted the isolation of a TCR sequence using a single PCR reaction using all 188 oligonucleotides simultaneously. Instead, prior art methods have utilized an array of simultaneous PCR reactions, each using a different, restricted pool of primers, followed by additional iterations of PCR using progressively smaller pools of primers.

SUMMARY OF THE INVENTION

Methods and compositions for isolating and identifying the sequence of the recombinant region of the alpha and/or beta chains of a T cell receptor (TCR) from a single T cell are provided. In some embodiments, a series of amplification reactions are used to isolate the alpha or beta chain of the TCR.

In one aspect, methods of isolating DNA encoding the variable regions of a T cell receptor (TCR) alpha or beta chain are provided. In some embodiments the methods comprise isolating genomic DNA from a single T cell and then amplifying a gene segment encompassing the TCR alpha or beta chain variable region by an enrichment amplification reaction to produce a first enrichment product. The first enrichment product comprises the V and J regions of the TCR alpha or beta chain from the single cell. The amplification reaction comprises incubating the isolated genomic DNA with a set of outer primers comprising at least one primer complementary to each of the V and J regions of the TCR alpha chain or beta chain. The amplification reaction may be a PCR reaction, such as a touchdown PCR reaction.

In some embodiments the first enrichment product is further amplified in an isolation amplification reaction to produce a second isolation product. The isolation amplification reaction may comprise incubating the first enrichment product with a set of inner primers comprising at least one primer complementary to each of the V and J regions of the TCR alpha chain or beta chain. The isolation product may be further amplified in a cloning amplification reaction to facilitate cloning into a vector. Further the product of the cloning amplification reaction may be further amplified in a homologous amplification reaction to increase yield of the desired product.

In other embodiments, methods of isolating the variable regions of a T-cell receptor (TCR) alpha or beta chain comprise: (a) isolating a single T cell; (b) performing whole genome amplification to amplify the genomic DNA of the T cell; (c) incubating the amplified genomic DNA with a set of outer primers in a genomic TCR alpha enrichment amplification reaction or genomic TCR beta enrichment amplification reaction to produce an enrichment product, wherein the set of primers comprises at least one outer primer complementary to substantially each V and J region of the TCR alpha chain or TCR beta chain; and (d) incubating the enrichment product with a set of inner primers in an TCR alpha isolation amplification reaction or TCR beta isolation amplification reaction to produce an isolation product, wherein the set of inner primers comprises at least one inner primer complementary to each of the V and J regions of the TCR alpha chain or TCR beta chain.

In some embodiments, the methods comprise the additional step of (e) incubating the isolation product with a set of cloning primers in a cloning amplification reaction to produce a cloning product, wherein the set of cloning primers comprises at least one cloning primer complementary to each of the V and J regions of the TCR alpha chain or TCR beta chain. A further homologous amplification reaction may also be used.

In other embodiments, kits are provided. For example, a kit may comprise a T-cell receptor (TCR) alpha outer primer set, a TCR beta outer primer set, a TCR alpha inner primer set and a TCR beta inner primer set. In some embodiments, each of the TCR alpha inner and outer primer sets comprises at least one primer complementary to each of the V and J regions of a TCR alpha chain and each of the TCR beta inner and outer primer sets comprises at least one primer complementary to each of the V and J regions of a TCR beta chain.

BRIEF DESCRIPTION OF THE DRAWINGS

FIG. 3 shows the results of the design and testing of primers against all alpha and beta V and J regions in the genome.

FIG. 4 illustrates the results of Jurkat TCR PCR with increasing numbers of oligonucliotides in the pool.

DETAILED DESCRIPTION OF THE INVENTION

Methods and compositions are provided for identifying the alpha and beta chains of specific TCRs from individual T-cells. In some embodiments, a single T cells is isolated and the genomic DNA of that T cell is amplified using whole genome amplification (WGA). An optional screening assay, for example a PCR-based assay, can be used to screen the product of the WGA to verify that genomic DNA encoding the T cell receptor is present. This can be accomplished, for example, by amplifying constant regions of the T cell receptor. If the appropriate genomic DNA is present, separate amplification reactions for the alpha and beta chain of the TCR are then performed. Several rounds of PCR may be carried out using different primer sets, as described in detail below, in order to isolate and amplify the DNA encoding the alpha and beta chains of the TCR. Generally, the product of each round of PCR is used as the template for the subsequent round of PCR.

Figure 1:
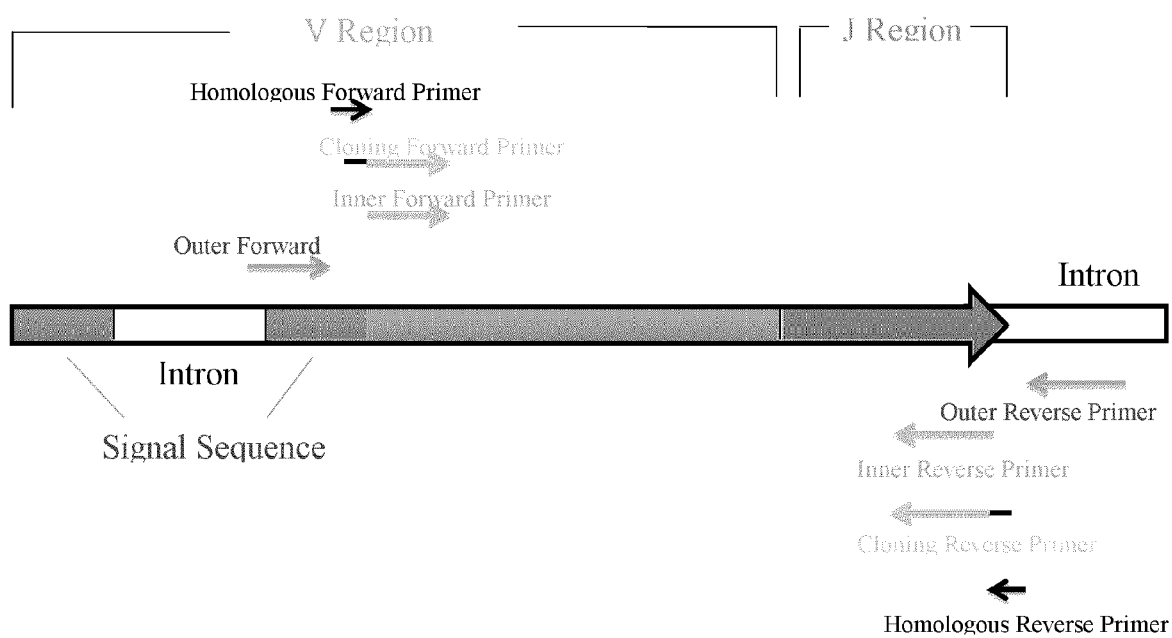
FIG. 1 is a representation of the structure of the genes encoding the TCR alpha and beta chains. The relative positions of outer, inner, cloning, and homologous primer annealing sites are also shown.

FIG. 1 summarizes various sets of primers that can be used in each round of amplification. The first round of amplification is typically an enrichment round in which outer forward and reverse primers are used on amplified genomic DNA to enrich for DNA sequences encompassing the TCR alpha or beta chain. The second round of PCR is an isolation round. Inner forward and reverse primers are used on the enriched product of round 1 to isolate TCR sequences from non-specific product. An optional third round of PCR is a cloning round. Cloning primers that overlap the inner primers are used to generate TCR sequences that contain ends with homology to a cloning vector, which may also function as an expression vector. An optional fourth round of PCR is a homologous "clean-up" round. Homologous primers are used to isolate TCR sequences with vector homology on their ends from non-specific product.

Following isolation, the amplified nucleic acid can be sequenced to determine the identity of the alpha and beta chains of the TCR from the single isolated T-cell. Furthermore, it can cloned into an expression vector for subsequent expression in a cell of interest.

Analysis of Populations of T Cells

In some embodiments, TCR sequences are isolated from a single T-cell that has itself been isolated from a population of T Cells. The population of T cells may be selected for a certain activity or set of activities, and TCRs isolated from one or more individual cells in the population. For example, populations of T cells with specificity for disease antigens such as melanoma antigens (for example MART1, NY-ESO, NA-17, GP-100, or Tyrosinase) can be isolated using FACs of patient T cells stained with tetramers for these antigens (see Example 3). In some embodiments, the population of T cells is a subpopulation of T cells with a certain activity; the subpopulation may be selected using an activity, a marker, and/or a set of markers.

Individual T cells are isolated from the population and the TCR alpha and beta chain sequences of the individual T cells are separately isolated by PCR. By way of example, a single cell may be isolated from tissue, from bodily fluid, or from cell culture. Examples of methods for isolating T Cells include Fluorescence Activated Cell Sorting (FACs), and serial dilutions. Other methods are known in the art.

Whole Genome Amplification:

Once an individual T-cell has been isolated, at least the portion of the genome encoding the TCR alpha and beta chains is amplified. For example, whole genome amplification (WGA) may be carried out. WGA has been used in a variety of applications, for example, large-scale genotyping (e.g. SNP typing, RFLP analysis), comparative genome hybridization (e.g. Southern blotting), and molecular cloning. In some embodiments, WGA is used to amplify the genomic DNA of the single isolated T cell.

One skilled in the art will appreciate that any number of WGA methods or kits can be used to perform the WGA step. In some embodiments, a PCR-based method of WGA is used (See, e.g. Zhang et at (1992). Proc Natl Acad Sci USA 89: 5847-51, incorporated herein by reference in its entirety). In other embodiments, an Omniplex method of WGA is used (Langmore, J. T. (2002). Genome Res. 14: 901-07, incorporated herein by reference in its entirety). Other methods of amplification of genomic DNA known in the art may be used.

In some embodiments, a multiple displacement amplification (MDA) method of WGA is used: Briefly, DNA synthesis is initiated by the addition of random hexamers to DNA, which prime the reaction. The Phi29 polymerase is used to elongate from each hexamer and continues until it reaches a downstream synthesis reaction. The upstream reaction then displaces the downstream reaction and continues replication and displacement. Additional priming and synthesis is able to occur on the displaced strands in a branching pattern, allowing for mass amplification from low levels of template. Phi29 is a highly processive enzyme, able to replicate long stretches of DNA (up to 100 kb). The polymerase also contains a 3' to 5' proofreading mechanism, making it 100 times more accurate than conventional PCR enzymes such as Taq (Telenius, H et at (1992). Genomics 13: 718-25). Dean et at ((2002). Proc. Natl. Acad. Sci. USA 99: 5261-66, incorporated herein by reference in its entirety) disclose a method of MDA which comprises an isothermal strand-displacing reaction, that can amplify 1-10 copies of human genomic DNA to produce 20-30 μg of product. MDA may be used to amplify DNA from crude sources, for example whole blood cells or whole tissue culture cells (Id. at 5263). Dean et al report that relative to PCR-based WGA methods, MDA increases genomic coverage, reduces amplification bias, and generates longer products (>10 kb for MDA versus ~1 kb for PCR-based amplification) (Id. at 5265-66).

One skilled in the art will appreciate that in some embodiments, the invention can comprise a method of WGA other than PCR, MDA, or Omniplex. In other embodiments, other known methods of amplifying at least the relevant portion of the genomic DNA of the cell are used.

In the some embodiments, after a single T cell is isolated, the cell is lysed. The lysis is performed using methods known in the art. For example, each cell can be sorted into 1.5 ul of alkaline lysis buffer (ALB), incubated at −20° C. for 30 minutes, and then incubated at 65° C. for 10 minutes to lyse that cell. After lysis, WGA is performed using a commercial kit, such as a Qiagen Repli-g Midi kit (catalog number 150043), which comprises an MDA method of WGA (See Qiagen "REPLI-g® Mini/Midi Handbook" February 2008, incorporated herein by reference in its entirety).

Screening of WGA Products:

Following WGA, or other amplification of genomic DNA, a screening assay is performed on the amplification products to verify that the appropriate genomic DNA was amplified and that the reaction was not contaminated. For example, such a screening assay can verify there was no bacterial contamination in the WGA reaction. In some embodiments, the screening assay comprises a PCR reaction. In some embodiments, the PCR primers are directed against a known un-rearranged human gene, for example ataxia telangiectasia mutated (ATM) (see Example 2). In other embodiments, the screening PCR primers are directed to the constant regions of the alpha and beta chains of the TCR. For example, the screening primers can comprise the primers described in Table 1. In the presence of amplified genomic DNA template, the sizes of the alpha and beta constant region products generated by these primers are 420 bp and 530 bp respectively. Other primer combinations can also be used to identify the presence of the TCR constant regions.

encoding the TCR alpha and beta chains of a single T cell. In other embodiments, the TCR alpha or beta chain may be isolated individually or in sequence.

In some embodiments, each series of amplifications comprises two rounds of amplification reactions: First, parallel enrichment reactions are performed to enrich previously-amplified genomic DNA for sequences encompassing the variable regions of the TCR alpha and beta chains. If both the TCR alpha and beta regions are to be identified, one reaction is carried out using primers to enrich for sequences encoding the variable region of the TCR alpha chain and a separate reaction is carried out to enrich for sequences encoding the variable region of the TCR beta chain. These may be referred to as the TCR alpha enrichment reaction and the TCR beta enrichment reaction, respectively. In some embodiments these reactions are carried out in parallel. In some embodiments, each of the enrichment reactions comprises forward and reverse primers that anneal to substantially all variable regions of the TCR alpha or beta chain. That is, in each enrichment reaction, the genomic DNA is incubated with a set of primers comprising at least one primer complementary to each of the V and J regions of the TCR alpha chain or TCR beta chain. In other embodiments a subset of primers is utilized. The primers for this step are referred to as outer primers (FIG. 1) and are described in more detail below.

Second, an isolation reaction is performed on the product of the enrichment reactions to isolate sequence encoding the variable region of the TCR alpha and beta chains. These reactions may be referred to as the TCR alpha isolation reaction and TCR beta isolation reaction, respectively. As with the enrichment reactions, each of the isolation reactions may be performed using a set of primers that anneal to substantially all variable regions of the TCR alpha or beta chain. Thus, the product of the enrichment reaction may be incubated with a set of forward and reverse primers comprising at least one primer complementary to each of the V and J regions of the TCR alpha chain or TCR beta chain. In other embodiments a

TABLE 1

Example Constant Region Diagnostic Primer Sequences

| SEQ ID NO: | Primer | Sequence |
|---|---|---|
| 1 | Fwd TCR-Alpha Constant Screening | CAGAACCCTGACCCTGCCGTGTACC |
| 2 | Rev TCR-Alpha Constant Screening | GCCATTCCTGAAGCAAGGAAACAGCC |
| 3 | Fwd TCR-Beta Constant Screening | GGCCACACTGGTGTGCCTGGCC |
| 4 | Rev TCR-Beta Constant Screening | CGGCGCTGACGATCTGGGTGAC |

In some embodiments, other techniques may be used to perform the screening assay on WGA amplification products, for example DNA comparative genome hybridization such as microarray screening or Southern blotting.

Design of Primers for Isolating TCR Alpha and Beta Chains:

The generalized structure of the gene encoding the TCR receptor alpha or beta chains is depicted in FIG. 1. In some embodiments, the alpha and beta chains of the TCR are isolated using a series of amplification reactions, preferably PCR reactions, comprising two or more sets of nested primers. In order to identify both the alpha and beta chains, two series of amplifications may be performed in parallel—one for the alpha chain and one for the beta chain—to isolate the genes subset of primers is utilized. The primers for this step are referred to as inner primers (FIG. 1) and are described in more detail below.

In some embodiments, the amplification reaction series also comprises a third cloning amplification reaction, such as a PCR reaction, in which end sequences with homology to a cloning vector are added to the isolated TCR alpha and/or beta chain sequence. These reactions may be referred to as the TCR alpha cloning reaction and TCR beta cloning reaction, respectively. As with the enrichment and isolation reactions, each of the cloning reactions may be performed using a set of primers that anneal to substantially all variable regions of the TCR alpha or beta chain. Thus, the product of the isolation reaction may be incubated with a set of forward and reverse primers comprising at least one primer complementary to each of the V and J regions of the TCR alpha chain or TCR beta chain, where the primers additionally comprise sequences with homology to a cloning vector. In other embodiments a subset of primers is utilized. The primers for this step are referred to as cloning primers (FIG. 1) and are described in more detail below.

In some embodiments, the amplification reaction series also comprises a fourth homologous amplification reaction, such as a fourth PCR reaction, to further isolate and amplify DNA segments comprising end sequences homologous to a cloning vector. This reaction may be referred to as the homologous reaction. The primers used in the homologous reaction are preferably homologous to the cloning vector sequences. The product of the cloning reaction is incubated with these forward and reverse primers. The primers for this step are referred to as homologous primers (FIG. 1) and are described in more detail below.

In some embodiments, the product of the isolation round using the inner primers is sequenced directly. In some embodiments, the product of the isolation round using the inner primers is cloned into a vector, for example TOPO-TA or TOPO-Blunt.

In other embodiments, the product of the amplification using the cloning primers is sequenced. This product may be cloned into a vector, for example an expression vector.

In other embodiments, the product of the amplification using the homologous primers is sequenced. It may be cloned into a vector, for example an expression vector.

Primers may be designed so that each set of inner and outer primers for the alpha chain contains at least one primer that anneals to each of the 44 possible alpha variable ("alpha V") regions and 76 possible alpha junctional ("alpha J") regions. Similarly, each set of inner and outer primers for the beta chain preferably contains at least one primer that anneals to each of the 54 possible beta variable ("beta V") regions and the 14 possible beta junctional ("beta J") regions. In some of these embodiments, one primer may anneal to two or more different possible regions. In some embodiments, the sequence of the primers is selected based on their predicted annealing temperatures to genomic sequences within the TCR gene.

Alpha Chain Primers.

In some embodiments, the primer sets for isolating sequence encoding the TCR alpha chain comprise outer primers and inner primers, as described herein; in other embodiments the primers sets comprise outer primers, inner primers and cloning primers, as described herein; in still other embodiments, the primer sets comprise outer primers, inner primers, cloning primers and homologous primers, as described herein:

Outer primers: Outer primers comprise forward and reverse outer primers (FIG. 1), in order to amplify the V and J regions. Each outer forward primer anneals to sequence about 5-40 base pairs upstream of the signal sequence junction of the alpha V region. In these embodiments, the outer primer set comprises at least one forward primer that anneals to each of the 44 possible alpha V regions. Each outer reverse primer anneals to sequence about 5-40 base pairs downstream of the exon/intron junction of the alpha J region. In these embodiments, the outer primer set comprises at least one reverse primer that anneals to each of the 76 possible alpha J regions. By way of example, one possible set of alpha chain outer primers is disclosed in Tables 3-1 and 3-2.

Inner primers: Inner primers comprise forward and reverse inner primers (FIG. 1), in order to amplify the V and J regions. Preferably a set of inner primers is used comprising at least one primer complementary to each V and J region of the TCR alpha chain. Each inner forward primer anneals to sequence at the start of the first amino acid downstream of the signal sequence of the alpha V region. In these embodiments, the forward inner primer set comprises at least one inner primer that anneals to each of the 44 possible alpha V regions. Each inner reverse primer anneals to sequence at or near the downstream end of the alpha J region. In these embodiments, the inner reverse primer set comprises at least one reverse primer that anneals to each of the 76 possible alpha J regions. By way of example, one possible set of alpha chain inner primers is disclosed in Tables 3-5 and 3-6.

Cloning primers: Cloning primers comprise forward and reverse cloning primers (FIG. 1), in order to amplify the V and J regions. Each cloning forward primer is designed to anneal to sequence that overlaps the sequence of an inner forward primer. Thus, a set of cloning primers that comprises at least one primer complementary to each V and J regions of the TCR alpha chain are used. In the preferred embodiments, the 5' end of each cloning forward primer also comprises about 10 to about 50, more preferably about 15 bases of homology to a desired vector, the "vector region," in order to facilitate cloning into a desired vector. For example, it may facilitate cloning by direct recombination into a vector, such as an expression vector, for example a lentiviral expression vector. Each cloning forward primer is designed to create a product that can be cloned directly into a vector. For an expression vector, the primers may be designed such that the product may be cloned within the correct reading frame, starting with the amino acid directly after the signal sequence. In other embodiments, the 5' end of each cloning forward primer instead comprises restriction sites that allow ligation into a desired vector, such as an expression vector. In some embodiments—for example embodiments in which TCR sequence is desired but functional TCR need not be expressed—the cloning forward primer does not necessarily produce an in-frame product, and the vector need not be an expression vector. Each cloning reverse primer is designed to anneal to sequence that overlaps the sequence of an inner reverse primer. In the preferred embodiments, the 5' end of each cloning reverse primer also comprises about 10 to about 50, more preferably about 15 bases of homology to facilitate insertion into a vector, for example direct recombination into an expression vector, for example a lentiviral vector. In other embodiments, the 5' end of each cloning reverse primer comprises restriction sites that allow ligation into a vector, such as an expression vector. By way of example, one possible set of alpha chain cloning primers is disclosed in Tables 3-9 and 3-10.

Homologous primers: Homologous "clean-up" primers are designed to anneal to the vector region of the product of the cloning reaction. That is, the homologous primers are designed to anneal to the 5' ends of the product of the cloning primers that are homologous to the vector of choice. The homologous forward primer anneals to the homologous region from the cloning forward (V) primer. The homologous reverse primer anneals to the homologous region from the cloning reverse (J) primer. See FIG. 1. Preferably, the homologous primers are specific to only the 15 bases of homology at the end of the cloning product. In other embodiments—for example, embodiments wherein the primers contain 5' restriction sites for cloning into a vector—each homologous primer anneals to the 5' sequence added by the cloning primers. By way of example, one possible set of homologous primers is disclosed in Table 3-13.

Beta Chain Primers.

In some embodiments, the primer sets for isolating sequence encoding the TCR beta chain comprise outer primers and inner primers as described herein; in other embodiments the primers sets comprise outer primers, inner primers and cloning primers as described herein; in other embodiments, the primer sets comprise outer primers, inner primers, cloning primers and homologous primers as described herein:

Outer primers: Outer primers comprise forward and reverse outer primers (FIG. 1), in order to amplify the V and J regions. Each outer forward primer anneals to sequence about 5-40 base pairs upstream of the signal sequence junction of the beta V region. In these embodiments, the outer primer set comprises at least one forward primer that anneals to each of the 54 possible beta V regions. Each outer reverse primer anneals to sequence about 5-40 base pairs downstream of the exon/intron junction of the beta J region. In these embodiments, the outer primer set comprises at least one reverse primer that anneals to each of the 14 possible beta J regions. By way of example, one possible set of beta chain outer primers is disclosed in Tables 3-3 and 3-4.

Inner primers: Inner primers comprise forward and reverse inner primers (FIG. 1), in order to amplify the V and J regions. Preferably a set of inner primers is used comprising at least one primer complementary to each V and J region of the TCR beta chain. Each inner forward primer anneals to sequence at the start of the first amino acid downstream of the signal sequence of the beta V region. In these embodiments, the forward primer set comprises at least one inner primer that anneals to each of the 54 possible beta V regions. Each inner reverse primer anneals to sequence at or near the downstream end of the beta J region. In these embodiments, the inner primer set comprises at least one reverse primer that anneals to each of the 14 possible beta J regions. By way of example, one possible set of beta chain inner primers is disclosed in Tables 3-7 and 3-8.

Cloning primers: Cloning primers comprise forward and reverse cloning primers (FIG. 1). Each cloning forward primer is designed to anneal to sequence that overlaps the sequence of an inner forward primer. Thus, a set of cloning primers that comprises at least one primer complementary to each V and J regions of the TCR beta chain are used. In the preferred embodiments, the 5' end of each cloning forward primer also comprises about 10 to about 50, more preferably about 15 bases of homology to a desired vector, the "vector region," in order to facilitate cloning into a desired vector. The homologous region may facilitate direct recombination into an expression vector, for example a lentiviral vector. Each cloning forward primer is designed to create a product that can be cloned directly into a vector. For an expression vector, the primers may be designed such that the product may be cloned within the correct reading frame, starting with the amino acid directly after the signal sequence. In other embodiments, the 5' end of each cloning forward primer instead comprises restriction sites that allow ligation into a desired vector, such as an expression vector. In some embodiments—for example embodiments in which TCR sequence is desired but functional TCR need not be expressed—the cloning forward primer does not necessarily produce an in-frame product, and the vector need not be an expression vector. Each cloning reverse primer is designed to anneal to sequence that overlaps the sequence of an inner reverse primer. In the preferred embodiments, the 5' end of each cloning reverse primer also comprises about 10 to about 50, more preferably about 15 bases of homology to facilitate insertion into a vector, for example direct recombination into an expression vector, for example a lentiviral vector. In other embodiments, the 5' end of each cloning reverse primer comprises restriction sites that allow ligation into a vector, such as an expression vector. By way of example, one possible set of beta chain cloning primers is disclosed in Tables 3-11 and 3-12.

Homologous primers. Homologous "clean-up" primers are designed to anneal to the vector region of the product of the cloning reaction. That is the homologous primers are designed to anneal to the 5' ends of the product of the cloning primers that are homologous to the vector of choice. The homologous forward primer anneals to the homologous region from the cloning forward (V) primer. The homologous reverse primer anneals to the homologous region from the cloning reverse (J) primer. See FIG. 1. In other embodiments—for example, embodiments wherein the primers contain 5' restriction sites for cloning into an expression vector— each homologous primer anneals the 5' added by the cloning primers. By way of example, one possible set of homologous primers is disclosed in Table 3-13.

Amplification of the TCR Gene:

In some embodiments, template genomic DNA undergoes two or more rounds of amplification. Two series of amplification reactions may be performed in parallel, one for the alpha chain and one for the beta chain. However, in some embodiments, it is possible to perform only the reactions for identifying the alpha chain or only the reactions for identifying the beta chain.

In some embodiments, two rounds of amplification reactions, such as PCR reactions, are performed, the first to enrich genomic template for sequence encompassing a TCR alpha or beta chain, and the second to isolate sequence encoding the TCR alpha or beta chain. In some embodiments, a third round of amplification, such as PCR, is also performed to add sequence homologous to a cloning vector to the ends of the DNA segments encoding the TCR alpha or beta chain. In some embodiments, a fourth round of amplification, such as PCR, is also performed to isolate DNA segments that contain end sequence homologous to a cloning vector.

First Round (Genomic TCR Enrichment Reaction):

In some embodiments, a first round of amplification is performed to enrich genomic template for all TCR loci. A first enrichment product is produced. All of the outer forward and outer reverse primers for a TCR chain (alpha or beta chain) are pooled, the product of WGA is added as template, and amplification is performed.

In some embodiments amplification is performed using a touchdown PCR protocol (for a description of touchdown PCR, see Don et al (1991). Nucleic Acids Res. 19: 4008, incorporated herein by reference in its entirety). The touchdown PCR protocol utilizes multiple iterations of a three-step cycle, each cycle comprising: first melting the template DNA at a melting temperature (TM)—for example 95° C.; second allowing primers to anneal at an annealing temperature; and third allowing polymerase to extend DNA at an extension temperature—for example, 70° C. The annealing temperature may be the same as the extension temperature, or annealing temperature may be the different from the extension temperature. In the first cycle, a top annealing temperature is used— for example 77° C. In each subsequent cycle of touchdown PCR, the annealing temperature is incrementally decreased in until a bottom annealing temperature at or slightly below the optimal annealing temperature is reached. In some embodiments, the annealing temperature is decreased by an increment of less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or more than 5.0° C. in each cycle until the bottom annealing temperature is reached—for example 60° C. Once the bottom annealing temperature is reached, one or more cycles are performed using the bottom annealing temperature. By way of example only, a sample touchdown PCR protocol for the first round is described in Table 3-14.

One skilled in the art will appreciate that a number of other amplification protocols can be used, and the protocol for each round may be optimized along different parameters including, but not limited to, annealing temperature(s), annealing time(s), extension temperature(s), extension time(s), number of cycles, type and amount of polymerase used, concentrations of deoxyribonucleic acid trisphosphates (dNTP's), buffer composition, magnesium concentration, and the addition or removal of additional reagents, for example betaine, bovine serum albumin (BSA), dimethyl sulfoxide (DMSO), or preCES (a cocktail of additives).

Second Round (TCR Isolation Reaction):

In some embodiments, a second round of amplification is performed to isolate specific alpha or beta chain sequence from the enriched genomic template. A second isolation product is produced. The inner forward and inner reverse primers for a TCR chain (alpha or beta) are pooled for the second round, and the enrichment product from the TCR enrichment reaction is added as a template. An amplification reaction, such as a touchdown PCR reaction, is then performed. By way of example only, a sample touchdown PCR protocol for the second round is described in Table 3-14. The skilled artisan will recognize that other amplification protocols can be used.

In some embodiments, products of the second TCR isolation round are used as template for DNA sequencing. In other embodiments, products of the second round are cloned directly into a vector. In other embodiments, products of the second round are used as template in a TCR cloning reaction, as described below.

Third Round (TCR Cloning Reaction):

In some embodiments, a third round of amplification is used to add sequence homologous to a cloning vector to the ends of DNA segments isolated in the second round (the isolation product). The cloning forward and reverse primers for a TCR chain (alpha or beta) are pooled for the third round, and isolation product from the second isolation round is added as a template. An amplification reaction, such as a touchdown PCR protocol, is then performed and a third cloning product is produced. By way of example only, a sample touchdown PCR protocol for the third round is described in Table 3-14. The skilled artisan will recognize that other amplification protocols can be used.

Products from the third round may be sequenced directly. They may also be cloned into a vector as desired, such as an expression vector. In some embodiments, products from the third round are purified via gel electrophoresis, for example on an agarose gel using techniques known in the art. In some embodiments, desired bands are about 300-400 bp in length.

Fourth Round (Homologous Reaction):

In the preferred embodiments, a fourth amplification reaction is performed to isolate and amplify DNA segments that contain end sequence homologous to a cloning vector. The homologous forward and reverse primers are pooled for the fourth round. Cloning product from the third amplification round is used as a template for a fourth amplification round to produce a fourth homologous product. In some embodiments a PCR protocol is performed. The PCR protocol comprises multiple iterations of a three-step cycles: first, melting the template DNA at a melting temperature (TM)—for example 95° C.; second, allowing primers to anneal at an annealing temperature—for example 65° C.; and third, allowing polymerase to extend DNA at an extension temperature—for example, 70° C. By way of example only, a sample PCR protocol for the fourth round is described in Table 3-14. In other embodiments, a touchdown PCR protocol may be performed.

Homologous products from the fourth amplification round may be sequenced directly. In some embodiments, products from the fourth round are purified via gel electrophoresis, for example on an agarose gel using techniques known in the art. In some embodiments, desired bands are about 300-400 bp in length. In some embodiments, the isolated gene for each T cell receptor is subsequently cloned into a vector. In some embodiments, the vector comprises an expression vector, for example a lentiviral expression vector.

Kits

In some embodiments, the present invention comprises kits that comprise one or more of the following materials: oligonucleotide primers—for example forward outer primers for the TCR alpha chain, reverse outer primers for the TCR alpha chain, forward outer primers for the TCR beta chain, reverse outer primers for the TCR beta chain, forward inner primers for the TCR alpha chain, reverse inner primers for the TCR alpha chain, forward inner primers for the TCR beta chain, reverse inner primers for the TCR beta chain, forward cloning primers for the TCR alpha chain, reverse cloning primers for the TCR alpha chain, forward cloning primers for the TCR beta chain, reverse cloning primers for the TCR beta chain, or homologous primers (see also Tables 1-15 for examples of oligonucleotide primers); working solutions of oligonucleotide primers; and pooled oligonucleotide primers—for example pooled outer primers for the alpha chain of the TCR.

In addition, the kits may comprise buffers; PCR enzymes—for example Taq polymerase; PCR additives—for example Magnesium, betaine, bovine serum albumin (BSA), dimethyl sulfoxide (DMSO), or preCES; dNTPs; PCR master mix; genomic DNA; positive control DNA—for example, a sequence encoding the TCR alpha or beta chain; antibodies—for example anti-CD3, anti-CD4, anti-VB 14 (in some embodiments, the antibodies may be conjugated to fluorophores or other detection molecules); tetramers—for example tetramers against MART or NY-ESO VB14 (in some embodiments, the tetramers may be conjugated to fluorophores or other detection molecules); WGA reagents; lysis reagents; cloning vector; instructions; and/or reference materials.

In some embodiments, the kits comprise one or more pools of multiple primers. In some embodiments a kit comprises a TCR alpha outer primer set, the outer primer set comprising forward and reverse primers, wherein the outer primer set comprises at least one primer complementary to substantially each common variant of the V and J regions of the TCR alpha chain. In other embodiments, a kit comprises a TCR beta outer primer set, the outer primer set comprising forward and reverse primers, wherein the outer primer set comprises at least one primer complementary to each common variant of the V and J regions of the TCR beta chain.

In other embodiments a kit comprises a TCR alpha inner primer set, the inner primer set comprising forward and reverse primers, wherein the inner primer set comprises at least one primer complementary to substantially each common variant of the V and J regions of the TCR alpha chain. In other embodiments a kit comprises a TCR beta inner primer set, the inner primer set comprising forward and reverse primers, wherein the inner primer set comprises at least one primer complementary to substantially each common variant of the V and J regions of the TCR beta chain.

In some embodiments, a kit comprises a TCR alpha outer primer set, a TCR beta outer primer set, a TCR alpha inner primer set and a TCR beta inner primer set.

In some embodiments, the pools of primers are as above, except that each primer set for the V region variants is in a separate pool from the corresponding primer set for the J region variants.

In some embodiments the kits also comprise a pool of cloning primers, each set of cloning primers comprising forward and reverse cloning primers with homology to a specific vector. A TCR alpha cloning primer set comprises at least one primer complementary to substantially each common variant of the V and J regions of the TCR alpha chain. In other embodiments, a TCR beta cloning primer set comprises forward and reverse cloning primers with homology to a specific vector, wherein the TCR beta cloning primer set comprises at least one primer complementary to substantially each common variant of the V and J regions of the TCR beta chain. The kit may additionally comprise the vector to which the cloning primers have homology. In some embodiments, the pools of primers are as above, except that each primer set for the V region variants is in a separate pool from the corresponding primer set for the J region variants.

In other embodiments a kit comprises a pool of homologous primers, including forward and reverse homologous primers that are homologous to the portion of the cloning primers that in turn is homologous to a specific vector.

In some embodiments a kit comprises a TCR alpha outer primer set, a TCR beta outer primer set, a TCR alpha inner primer set, a TCR beta inner primer set, a TCR alpha cloning primer set, and a TCR beta cloning primer set. The kit may additionally comprise a homologous primer set.

Example 1

Figure 2:
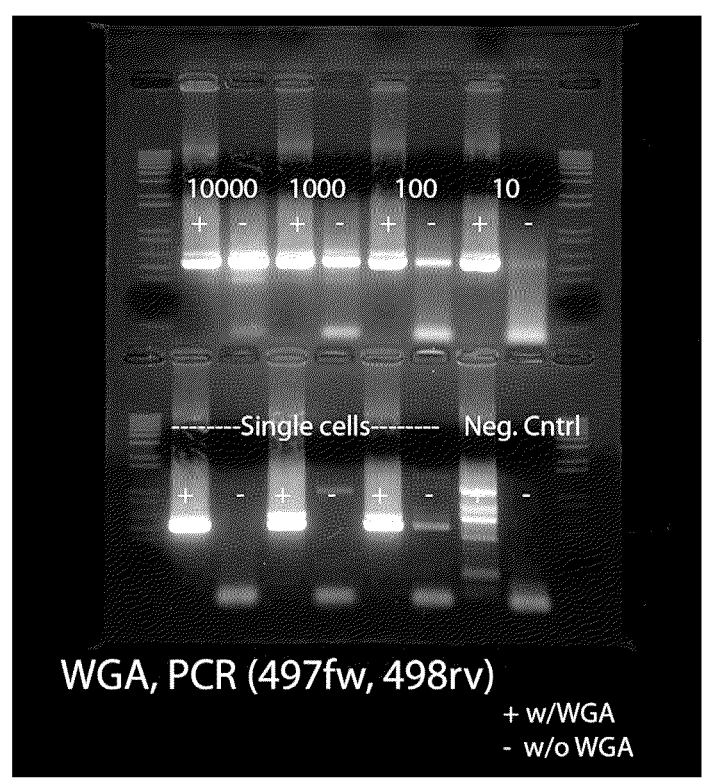
FIG. 2 shows the results of Jurkat cell TCR-specific PCR with or without WGA. Genomic DNA was isolated from Jurkat cells diluted from 10,000 to single cells. A Jurkat TCR alpha chain-specific PCR was run on samples with and without WGA. Alpha chains were isolated from single genomes only when these genomes were WGA-amplified.

Cells from the well-characterized Jurkat T cell liner were used to validate the primer set and PCR protocol for isolating TCR alpha and beta chain sequences. Cells were serially diluted into two sets of wells of PBS containing 10000, 1000, 100, 10, and single cells. Both sets of cells were lysed but only one was amplified using WGA. PCR using oligonucleotides designed against Jurkat-specific alpha chains was run on both sets. In the absence of WGA, PCR amplification the TCR alpha chain (target size ~350 bp) produced very low yields for templates with fewer than 100 cells. PCR amplification of samples processed using WGA produced high yields (FIG. 2).

Figure 3A:
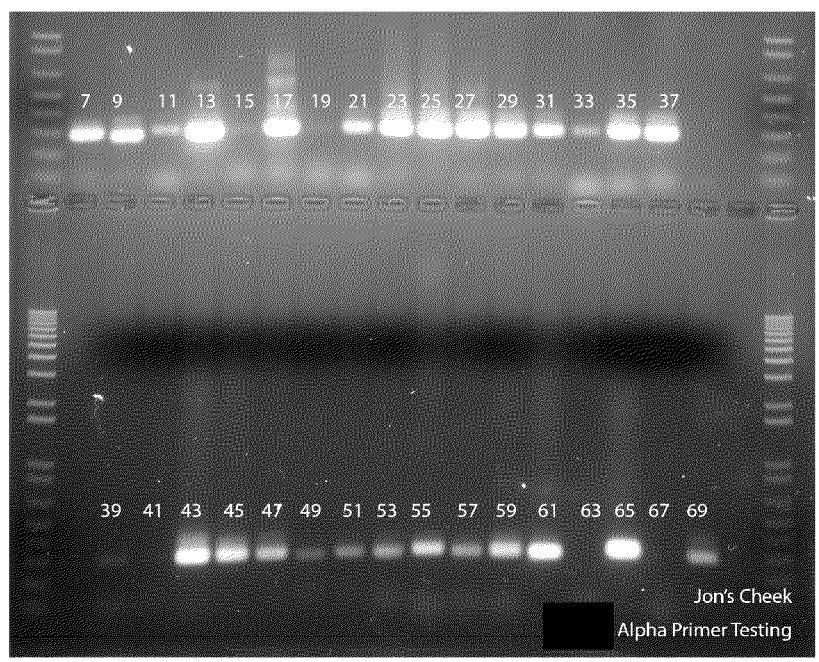
FIG. 3a is the relative positions of inner and outer primers.
Figure 3B:
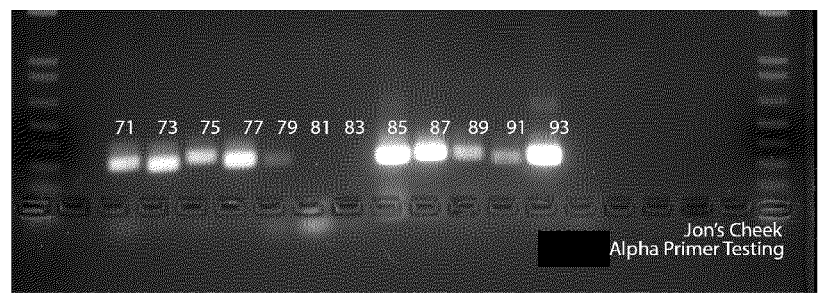
FIG. 3b is a test of the ability of each of the oligonucleotides from 3a to function under identical PCR conditions.

In order to isolate all possible rearrangements of the alpha and beta chains by nested PCR, two sets of oligonucleotides (inner and outer) were designed against all 188 V and J regions of both chains. Forward inner oligonucleotides in the V region were designed downstream of the V region signal sequence and intron. Care was taken to ensure that the primer would create a template capable of cloning into an expression vector while maintaining the correct reading frame starting with the amino acid directly after the signal sequence. Reverse inner oligonucleotides in the J region were designed at the ends of the J regions while also maintaining reading frame (FIG. 3a). Outer oligonucleotides were designed 20-30 base pairs upstream of their corresponding inner oligonucleotides. Alpha and beta forward primers were designed with BbvCI and SbfI restriction sites respectively at the ends to facilitate cloning. To confirm the ability of each of these oligonucleotides to function under identical PCR conditions, corresponding reverse primers were designed for each V and J region. PCR was performed using unrearranged genomic DNA as template using each pair of oligonucleotides. All oligonucleotides were functional under the same PCR conditions (FIG. 3b).

Figure 4A:
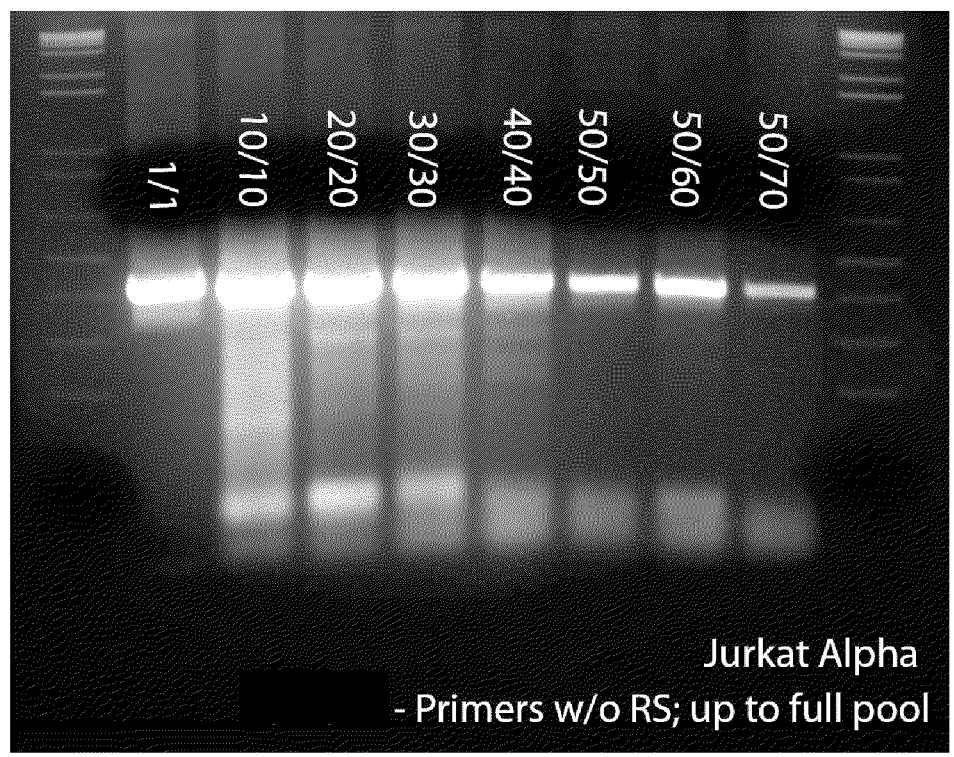
FIG. 4a shows the number of Forward/Reverse primers in each pool for TCR alpha chain-specific PCR.
Figure 4B:
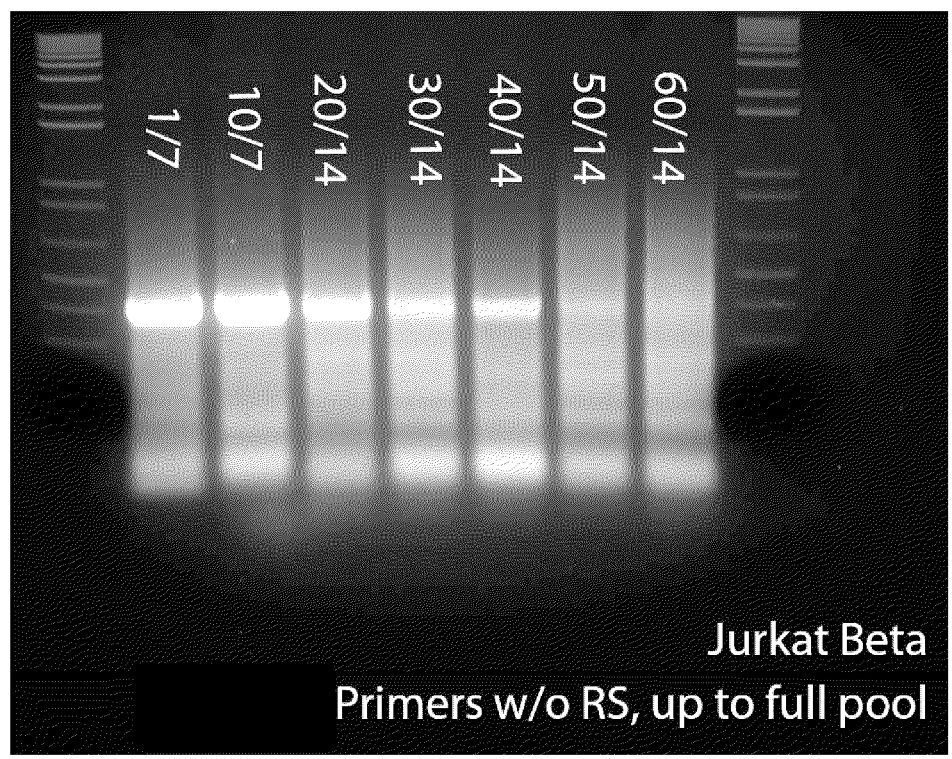
FIG. 4b shows the number of Forward/Reverse primers in each pool for TCR beta chain-specific PCR.

To minimize the number of reactions necessary for TCR amplification, the amplification protocol was multiplexed by pooling oligonucleotides into groups of V and J inner primers. Tests were run to determine the minimum number of forward and reverse pools of inner oligonucleotides (maximum number of oligonucleotides in each reaction) that could still isolate a single TCR. Multiplexed PCRs with increasing number of inner primers were performed on template genomic DNA isolated from cultured Jurkat cells to determine the maximum number of primers that still permitted successful TCR amplification. (FIGS. 4a, 4b). Pools of 10 forward and reverse alpha primers (fw/rv) were added to PCR reactions until all primers against alpha loci were present in a single reaction. For example, a pool of 50 forward and 70 reverse primers allowed isolation of a single alpha chain. The Jurkat alpha chain could be isolated with all primers against alpha loci present in a single reaction (FIG. 4a). Pools of 10 forward and reverse beta primers (forward/reverse) were added to PCR reactions until all primers against beta loci were present in a single reaction. The Jurkat beta chain was isolated with all primers in a single reaction (FIG. 4b). For example a pool of 60 forward and 14 reverse primers allowed isolation of a single beta chain.

Example 2

In this example, TCR sequences were isolated from a specific population of T cells, CD25+ regulatory T-cells (T-regs). T-regs were obtained from a patient blood sample from the University of California, Los Angeles and are diluted to single cells. These cells were lysed, amplified by WGA, and confirmed to contain human genetic material by a PCR for a known unrearranged human gene, ataxia telangiectasia mutated (ATM). The TCR isolation protocol was run on these samples. Four different alpha chains and eight different beta chains were identified. Amplified chains were cloned into a TOPO shuttle cloning vector, and sequenced using techniques known in the art. They were found to be aV9-2J33, aV17J33, aV2J3, aV26-2J33, bV18J2-2, bV6-1J1-1, bV4-1J2-5, bV11-2J2-2, bV6-2J2-7, bV9J2-7, bV6-1J2-2, bV6-8J1-1. These sequences were aligned against the specific V and J regions of the genome and were 100% homologous except for the N region at the junction of the V and J regions.

Example 3

NY-ESO TCR Isolation

Figure 5:
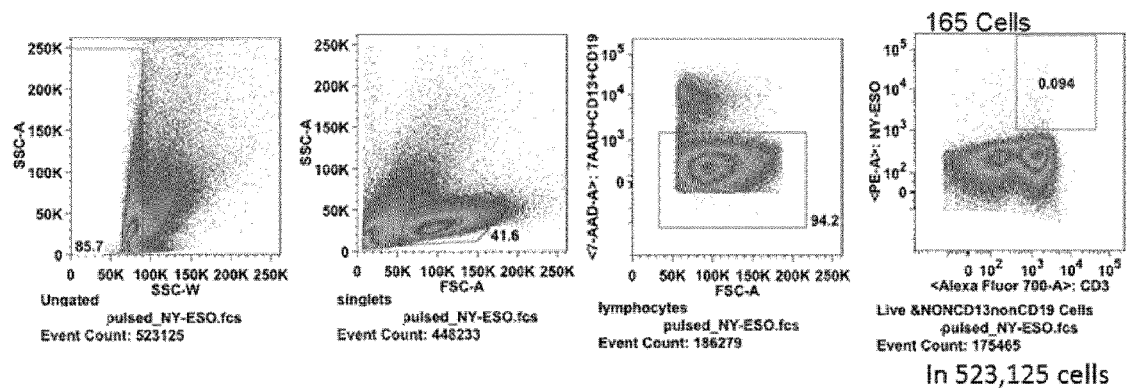
FIG. 5 shows the isolation of melanoma-specific T cells. Three alpha-beta pairs were isolated from a strip of eight NY-ESO+ T-cells. Cells were obtained from a patient sample and stained with an NY-ESO specific tetramer.
Figure 6:
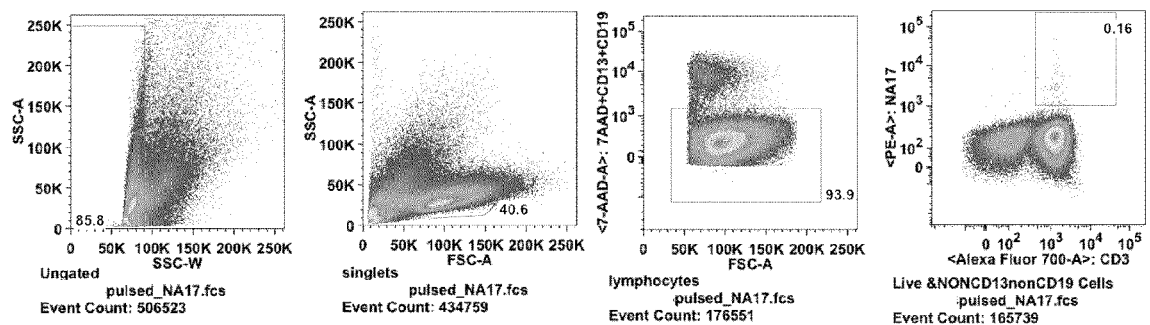
FIG. 6 shows the isolation of NA-17 specific T cells. Four alpha chains and five beta chains were isolated from a strip of eight NA-17+ T-cells. Cells were obtained from a patient sample and stained with an NA-17 specific tetramer.

In this example, TCR sequences were isolated from a population of T cells with anti-melanoma activity. CD25+ regulatory T-cells (T-regs) were isolated Patient samples demonstrating clinical anti-melanoma activity were stained with antibodies against CD3, CD13, CD19, CD4, CD8. CD3+ patient T-cells were stained with melanoma antigen-specific tetramers, including NYSEO, MART 1, NA-17, Tyrosinase and GP100. 7-AAD negative live cells were further gated to be CD13− CD19− CD3+ and tetramer positive (FIGS. 5, 6). Cells meeting the gating criteria were individually sorted into 1.5 ul of alkaline lysis buffer (ALB), each cell added to a single well of a 96-well plate, and frozen at −20° C. for transport.

WGA kits were obtained from Qiagen (Repli-G) and GE Healthcare Life Sciences (Illustra GenomiPhi V2 DNA Amplification Kit) and amplification was done according to Spits, C. et al (2006). Nature Protocols 1: 1965-70. Briefly, cells were sorted into 1.5 ul of alkaline lysis buffer (ALB) and incubated at −20° C. for 30 minutes. Reactions were incubated at 65° C. for 10 minutes to lyse cells prior to addition of 9 ul of GenomiPhi sample buffer, 9 ul of GenomiPhi reaction buffer and 1 µl of Phi29 enzyme. Reactions were run isothermally at 30° C. for 2 hours and inactivated at 65° C. for 10 minutes. The products were stored at 4° C.

To minimize the number of reactions necessary for TCR amplification, the PCR amplification was multiplexed by pooling oligonucleotides into groups of V and J primers. The first round PCR reactions was performed in 20 µl reactions comprising: 1 µl of WGA product; 10 µl of Novagen KOD Hot Start Master Mix; 4 µl of DEP-C treated H$_2$O; 4 µl of a 5× solution of preCES additive; 0.5 µl of pooled forward primers; 0.5 µl of pooled reverse primers (pools of primers are created by combining 5 µl of 100 µM solution of each primer and creating 20 µl aliquots). The primers pairs used for amplifying the alpha chain were the alpha V outer primers (Table 3-1) and the alpha J outer primers (Table 3-2). The primer pairs used for amplifying the beta chain were the beta V outer primers (Table 3-3) and the beta J outer primers (Table 3-4). The PCR amplification protocol for the first round is summarized in Table 3-14. One skilled in the art will appreciate that parameters of the PCR protocol, for example annealing temperatures and incubation times, can readily be altered to optimize the protocol for a certain set of primers and/or template.

In the second round of PCR, 1 µl of product from the first round was added to a PCR cocktail comprising all of the inner primers for either the alpha or the beta chain. The primer pairs used for amplifying the alpha chain are the alpha V inner primers (Table 3-5) and the alpha J inner primers (Table 3-6). The primer pairs used for amplifying the beta chain are the beta V inner primers (Table 3-7) and the beta J inner primers (Table 3-8). The PCR cocktail is otherwise as described in the first round. The PCR amplification protocol for the second round is summarized in Table 3-14.

In the third round of PCR, 1 µl of product from the second round is added to a PCR cocktail comprising all of the cloning primers for either the alpha or the beta chain. The primer pairs used for amplifying the alpha chain are the alpha V cloning primers (Table 3-9) and the alpha J cloning primers (Table 3-10). The primer pairs used for amplifying the beta chain are the beta V cloning primers (Table 3-11) and the beta J cloning primers (Table 3-12). The PCR cocktail is otherwise as described in the first round. The PCR amplification protocol for the third round is summarized in Table 3-14.

Product from the third round was added to a cocktail comprising the homologous primers (Table 3-13), and amplified using the protocol disclosed in Table 3-14. Three cells yielded both alpha and beta chains, and one cell yielded an alpha chain. The pairs were TRAV12-1J1, TRBV5-6J1-1; TRAV38-2DV8J53, TRBV5-6J1-2; and TRAV8-3J44, TRBV5-6J1-1. The unpaired alpha chain was TRAV21J47. Upon sequence analysis, it was found that all chains aligned perfectly with their corresponding genomic regions and regions of junction diversity could be readily identified. The receptor TRAV38-2DV8J53, TRBV5-6J1-2 was found to be a non-functional rearrangement with no open reading frames. It was found that two of the isolated TCRs have a common identical beta chain (TRBV5-6J1-1). Without limiting the invention to any one theory, this result could be explained by positive selection, where the beta chain first rearranges and is expressed on the surface with the pre-T-cell receptor alpha chain (pTalpha). If the beta chain is positively selected for, a subsequent alpha chain will undergo rearrangement.

TABLE 3-1

Alpha V Outer Primers

| SEQ ID NO: | | |
|---|---|---|
| 5 | 5' | TCRaV1-2us;CCAATGGCTCAGGAACTGGGAATGC; |
| 6 | 5' | TCRaV2us;GGAAAAAATGCAAAACAGGTAGTCTTAAATAAGCATTC; |
| 7 | 5' | TCRaV3us;GACCCCCCCAATCCCGCCC; |
| 8 | 5' | TCRaV4us;CAGACACAGCAAAAGAGCCTAGAACCTGG; |
| 9 | 5' | TCRaV5us;GATAATATAGCTCTCTTGGCTGGAGATTGCAGGT; |
| 10 | 5' | TCRaV6us;TAACACCTATCAAACTAAACAGAATGGCTTTTTGG; |
| 11 | 5' | TCRaV7us;AAGAAACAAACAATAAAAGCTTTGTTTGGCTACATAATT; |
| 12 | 5' | TCRaV8-1us;AAGACCTGGGTTCCAGCCACTTTCCTACT; |
| 13 | 5' | TCRaV8-2us;CTCCTAGCTCCTGAGGCTCAGGACCCCTGGCTTC; |
| 14 | 5' | TCRaV8-3us;ACACCTCTTGGTCTTGGTCTCTTCAGACACTT; |
| 15 | 5' | TCRaV8-4us;TGTCCGCTCTGCTCAGGGCCCT; |
| 16 | 5' | TCRaV9-1us;TTTTCCTCACACTAAGAAGACAAGACCCAAGG; |
| 17 | 5' | TCRaV10us;TAGTGTTAAAAAAAAAGAGAAGATGTTGAATACACAAGTCAACT; |
| 18 | 5' | TCRaV12-1us;ATTTCTTTTTGGATTGAAAATTTTAATCCTCAGTGAAC; |
| 19 | 5' | TCRaV12-2us;AAATATCCATTCTAGGTGCATTTTTTAAGGGTTTAAAATTT; |
| 20 | 5' | TCRaV13-1us;ACAACCTGATGATAGAAGTAACTCTTATAACTGGAGGTTG; |
| 21 | 5' | TCRaV13-2us;CGATGATGGAAGTAGCTCTTATGGCTGGAGAT; |

TABLE 3-1-continued

Alpha V Outer Primers

| SEQ ID NO: | | |
|---|---|---|
| 22 | 5' | TCRaV14D4us;CACCTCACAGTACAGAGTCCTGAAAATAAAGAAGAAGA; |
| 23 | 5' | TCRaV9-2us;TTCTTCATGTTAAGGATCAAGACCATTATTTGGGTAA; |
| 24 | 5' | TCRaV12-3us;AAATGAGAAACGTTTGTTATTATTTTTTTTCGTGTTTAA; |
| 25 | 5' | TCRaV8-6us;TGAGGCTCAGCGCCCTTGGCTTCTGTCCGCC; |
| 26 | 5' | TCRaV16us;CAGAGTGTCTATGTGGCTGAATCGTTTCCAG; |
| 27 | 5' | TCRaV17us;TCATCTGTGACTGAGGAGCCTTGCTCC; |
| 28 | 5' | TCRaV18us;ACCTTTCGGTTTGGATATCTCTCAACAAAACC; |
| 29 | 5' | TCRaV19us;AGACGGAGCACGGAACATTTCACTCAG; |
| 30 | 5' | TCRaV20us;AAGAAGGTTGGAATTATCGTAATTTGTTTCTAGGCTG; |
| 31 | 5' | TCRaV21us;CTTGTGAGCCATTCTCCATATTTCAGATATAAGATTTCAG; |
| 32 | 5' | TCRaV22us;CCAAGGTTTAGTTAAATATATCTTATGGTGAAAATGCCC; |
| 33 | 5' | TCRaV23D6us;GTTGGGAAGACTGGAAGACCACCTGG; |
| 34 | 5' | TCRaV24us;TTCCACAGATTTTGGCTGAAAAACGTTTTTCT; |
| 35 | 5' | TCRaV25us;GTACCAGGCAACCCATTTAGGAGAAGTTGG; |
| 36 | 5' | TCRaV26-1us;AACCTAGAATCAGACACAAAAACTGAACTCTGGG; |
| 37 | 5' | TCRaV8-7us;CCCACTCAGGAGATCTTCTAGAATAGAGCTCTCA; |
| 38 | 5' | TCRaV27us;AGGAGCAGCTAAAGTCAGGGGCCATGT; |
| 39 | 5' | TCRaV29DV5us;TGCAGCTTTCTAGGCAGGAGACAAGACAAT; |
| 40 | 5' | TCRaV30us;GTTAAGGAAGCCCATTCAGAAGCTGACTGG; |
| 41 | 5' | TCRaV26-2us;GACACAGAGTCTGAGTTCTGGGGCCTG; |
| 42 | 5' | TCRaV34us;GCAAAGTAACTTCTGCTGGGGAAGCTCAT; |
| 43 | 5' | TCRaV35us;GTGTCACTCTAAGCCCAAGAGAGTTTCTTGAAGC; |
| 44 | 5' | TCRaV36DV7us;TTAAAGGTAGTGAATCACGTTTTGCCCAGG; |
| 45 | 5' | TCRaV38-1us;AACCCATCAGAGCAGGAGACTTTTCACTCT; |
| 46 | 5' | TCRaV38-2DV8us;ATACTCAAGGTTCAGATCAGAAGAGGAGGCTTCTC; |
| 47 | 5' | TCRaV39us;CAACTTTCAAGGCTCCTAAATCTGAGTTTTCAGTG; |
| 48 | 5' | TCRaV40us;AACTGTGAATCCTCACTTCAACAGTGATGCC; |
| 49 | 5' | TCRaV41us;ATATATTCCGAAATCCTCCAACAGAGACCTGTG; |

TABLE 3-2

Alpha J Outer Primers

| SEQ ID NO: | | |
|---|---|---|
| 50 | 3' | TCRaJ1 Intron;GGTCCCACCGAGGCTTTAGTGAGCA; |
| 51 | 3' | TCRaJ2 Intron;AGAGAAAGGATTAGTGACACTGGCCCATGG; |
| 52 | 3' | TCRaJ3 Intron;GCATTTTGGACAAAGAAGAAATAGTTGTCCGTC; |
| 53 | 3' | TCRaJ4 Intron;CTGTTTTCTCATAGACAAGTGGTCAGTTCTTTTTGC; |

TABLE 3-2-continued

Alpha J Outer Primers

| SEQ ID NO: | | |
|---|---|---|
| 54 | 3' TCRaJ5 Intron; | TTCATCATCTAAGAAAGCAGAGTAGGGCCTTTCT; |
| 55 | 3' TCRaJ6 Intron; | TCTCACTACTACAGTATCCTTCCATAATATAATCTGTCTGCAA; |
| 56 | 3' TCRaJ7 Intron; | TCTCCAGCACAGGGTAGCGATGGG; |
| 57 | 3' TCRaJ8 Intron; | ACCAGAATAATTATATCCATATATGCCCAATATTGAGGATA; |
| 58 | 3' TCRaJ9 Intron; | CCCCTAAAAAGAAAAAAATCAATGAAAACAGATGTTC; |
| 59 | 3' TCRaJ10 Intron; | CACCTTTTCTTCCACTTATTGTCACCAGAATACATT; |
| 60 | 3' TCRaJ11 Intron; | CAATACATATGGAAGCCTTAAACCAGATAAGGGG; |
| 61 | 3' TCRaJ12 Intron; | TTTCCTGAGACATGAAGACATTTTACCCTCAATC; |
| 62 | 3' TCRaJ13 Intron; | CAAATGTTACGGTCTGAGAGAAGACAACACAAG; |
| 63 | 3' TCRaJ14 Intron; | AGTAAGTTTAGTGGGTCTCAGTAGCCACATTAAGCC; |
| 64 | 3' TCRaJ15 Intron; | TCACCTGTGCAATATATGACTACAGGATAAGTACAAGC; |
| 65 | 3' TCRaJ16 Intron; | CTTAGATTTCCAAAAAAGCTTATTACTTGTCTCAAAAACTAATC; |
| 66 | 3' TCRaJ17 Intron; | GCACATTGAATTGCAAATTGATGACAAGG; |
| 67 | 3' TCRaJ18 Intron; | GAGTTAATTCATCTCCCCTTTTAATTTCTCCACAGTAATA; |
| 68 | 3' TCRaJ19 Intron; | GAAGAAACTTTGCTCCCCTGGCCCT; |
| 69 | 3' TCRaJ20 Intron; | TGCTGAAAAACCTACCCACCATTTTGCTTAA; |
| 70 | 3' TCRaJ21 Intron; | AATACAGACTGAAAAGAAGAATTTAGCATAATGTGTTGGT; |
| 71 | 3' TCRaJ22 Intron; | CCCATTAAGTTACATGTACAGAATACATTTGTAGATTAGTAAATCAG; |
| 72 | 3' TCRaJ23 Intron; | GGTCTAAATCAGCCCTTAATCCACAGACATTG; |
| 73 | 3' TCRaJ24 Intron; | GCATGCAGGGCATGCCAAATACTAAGG; |
| 74 | 3' TCRaJ25 Intron; | AAAGAGGGCAAGTTTTCCTCTTGGAGATAATCATA; |
| 75 | 3' TCRaJ26 Intron; | AGCTTCTCCCCACATCAAGCACTGGACT; |
| 76 | 3' TCRaJ27 Intron; | TTCAAACTAATGATTTGATTGATTGCCCCTG; |
| 77 | 3' TCRaJ28 Intron; | AGCTTCTGCATGATGGAAGACAGGCTTCT; |
| 78 | 3' TCRaJ29 Intron; | AAATAATTCAAGGGAAGAAGCCATTGCTGAG; |
| 79 | 3' TCRaJ30 Intron; | CACTCTCAGCAGTTTGAACTCAGTGGGAGTTA; |
| 80 | 3' TCRaJ31 Intron; | AAATCTCCACTAACTTCACGGGATTTATTTGTTTG; |
| 81 | 3' TCRaJ32 Intron; | CGCTTCCTACTTGCCATGGACACAGAA; |
| 82 | 3' TCRaJ33 Intron; | TGCTACACTTTGTGCATTATTCAACTAGTGTCTCCT; |
| 83 | 3' TCRaJ34 Intron; | TTCATTTAAAAAAAAAAGAAAAAGAAAAAGAAAACACCTTTT; |
| 84 | 3' TCRaJ35 Intron; | CATAAGAAGAACTGTTCTATATGATTTACGGACATAACAGC; |
| 85 | 3' TCRaJ36 Intron; | GTGTCTGGGATGTGAGAACTTGTCATTACAGACTAA; |
| 86 | 3' TCRaJ37 Intron; | GACAGAGAAGATTAAACAAAAAATGAACAGAGTGGATAAC; |
| 87 | 3' TCRaJ38 Intron; | GGCAGTTTCTGAGATATTTCAAACTGCACAGAC; |
| 88 | 3' TCRaJ39 Intron; | TCAGTGCTACGGCTTCCTTTTGAAATTAGAGC; |
| 89 | 3' TCRaJ40 Intron; | GTCCCTCAAACATGAACACCAACAACCTTTAA; |
| 90 | 3' TCRaJ41 Intron; | CAACAGGTCCCATTGGATTTCTTTCCAGA; |

TABLE 3-2-continued

Alpha J Outer Primers

| SEQ ID NO: | | |
|---|---|---|
| 91 | 3' TCRaJ42 Intron; | ATTCTGTTGCCCAGAGTGACAAAGTACTGATGAT; |
| 92 | 3' TCRaJ43 Intron; | CAGCACCATTGCTCACTCAGGTCAGC; |
| 93 | 3' TCRaJ44 Intron; | TGCAGTATCCCTGTTTTAAAGGAACACACAG; |
| 94 | 3' TCRaJ45 Intron; | GGTTTAGAAATGTCCCCATGAGGACTGCA; |
| 95 | 3' TCRaJ46 Intron; | CTCAAATGTCAGGCTAGAACAAATAATAGGAAAAGGC; |
| 96 | 3' TCRaJ47 Intron; | AGCCAGAAAAAGTTTATTTAATATGCAATGAAACCCA; |
| 97 | 3' TCRaJ48 Intron; | ATGTCTACTATGATCCCCAGAATCTTATGCAGGC; |
| 98 | 3' TCRaJ49 Intron; | CTCTTTCTGCAGTTTAAAGGGTTTGCTCAACAC; |
| 99 | 3' TCRaJ50 Intron; | CTAATGTATGAGACTGTTAGCCCCAGCGCA; |
| 100 | 3' TCRaJ51 Intron; | CGGGGAAGGGAGCAAAAGTACATAAGGA; |
| 101 | 3' TCRaJ52 Intron; | CTGACACTGGGGTGACATTCCAGAATTTC; |
| 102 | 3' TCRaJ53 Intron; | GGAGGGGCAAGTAATTAAATCAGAAGTGTTTGAAT; |

TABLE 3-3

Beta V Outer Primers

| SEQ ID NO: | | |
|---|---|---|
| 103 | 5' TCRbV2us; | CCACAGGACCAGATGCCTGAGCTAGG; |
| 104 | 5' TCRbV3-1us; | CACTGCAGACCAGAATCCTGCCCTG; |
| 105 | 5' TCRbV4-1us; | CAGCACCTCGCCCAAAGGACCC; |
| 106 | 5' TCRbV5-1us; | GGAGGACCAAGCCCTGAGCACAGA; |
| 107 | 5' TCRbV6-1us; | TATCACCGATGCACAGACCCAGAAGACC; |
| 108 | 5' TCRbV7-1us; | TCCTACTCACAGTGACTCTGATCTGGTAAAGCTC; |
| 109 | 5' TCRbV4-2us; | TCACCCAGAGGACCCCAGTCAGAGG; |
| 110 | 5' TCRbV6-2us; | TCCCTTTTCACCAATGCACAGACCCA; |
| 111 | 5' TCRbV4-3us; | ACCTCACCCAGAGGACCCCAGTCAGA; |
| 112 | 5' TCRbV6-3us; | CCTTTTCACCAATGCACAGACCCAGAG; |
| 113 | 5' TCRbV7-2us; | CTCACAGTGATCCTGATCTGGTAAAGCTCCC; |
| 114 | 5' TCRbV6-4us; | GCCTTTCATCAACACACAGACCCAGAAGA; |
| 115 | 5' TCRbV7-3us; | TCCTGCTCACAGTGACCCTGATCTGGTA; |
| 116 | 5' TCRbV5-3us; | CCCAGGAGGACCAAGCCCTGAATC; |
| 117 | 5' TCRbV9us; | GGAGCTTAGGAACTTCAGAATGCTTACTACAGAGA; |
| 118 | 5' TCRbV10-1us; | CTTCAGTCTGCCCACAGCAGGGCT; |
| 119 | 5' TCRbV11-1us; | CTCCTCTGCTCCTGTTCACAAGGACCCT; |
| 120 | 5' TCRbV10-2us; | AATTTGCCCACAGCAGGGCTGG; |
| 121 | 5' TCRbV11-2us; | TTTTGCTCACAGTGACCCTGATTGGG; |
| 122 | 5' TCRbV6-5us; | CTGCTCCCCTTTCATCAATGCACAGATA; |
| 123 | 5' TCRbV7-4us; | GCTCCTGCTCATAGTGACACTGACCTGGTA; |
| 124 | 5' TCRbv5-4us; | CCCCAGGAGGACCAAGCCCTGAAT; |
| 125 | 5' TCRbV6-6us; | CCTTTCATCAATGCACAGATACAGAAGACCC; |
| 126 | 5' TCRbV7-5us; | GCTCCTGCTCACAGTGACACTGATCTGGTA; |
| 127 | 5' TCRbV5-5us; | CCCAGGAGGACCAAGCCCTGAATC; |
| 128 | 5' TCRbV6-7us; | CCCCTTTCATCAATGCACAGACCCAG; |
| 129 | 5' TCRbV7-6us; | TGCTGCTGCTCACAGTGACACTGATCTG; |
| 130 | 5' TCRbV5-6us; | TTCCCCAGGAGAACCAAGCCCTGA; |
| 131 | 5' TCRbV6-8us; | CCCTTTTATCAATGCACAGACCCAGAAGAC; |
| 132 | 5' TCRbV7-7us; | TCCGCTCCTGCTCACAGTGACACTGAT; |
| 133 | 5' TCRbV5-7us; | TTTCCCAGGAGGACCAAGCCCTG; |
| 134 | 5' TCRbV6-9us; | CCTTTCATCAATGCACAGACCCAGAAGAC; |
| 135 | 5' TCRbV7-8us; | TTCTGTTCACAGTGACACTGATCTGGTAAAGCC; |
| 136 | 5' TCRbV5-8us; | CCAGGAAGACCAAGCCCTGAATCAGG; |
| 137 | 5' TCRbV7-9us; | CTGCTCACAGTGACCCTGATCTGGTAAAGC; |
| 138 | 5' TCRbV13us; | CAAAAGCCCTGCTTTCTCACCCCAG; |
| 139 | 5' TCRbV10-3us; | CTATTTCCCCAGGCAGGGCTGGG; |
| 140 | 5' TCRbV11-3us; | CTGCTCCTGCTCACAGTGACCCTGATC; |

TABLE 3-3-continued

Beta V Outer Primers

| SEQ ID NO: | | |
|---|---|---|
| 141 | 5' TCRbV12-3us; | CTCACAGAGGGCCTGGTCTAGAATATTCCA; |
| 142 | 5' TCRbV12-4us; | TTCTTTGCTCATGTTCACAGAGGGCCTG; |
| 143 | 5' TCRbV12-5us; | TTCGTGCCCACAAGGGCCTCAT; |
| 144 | 5' TCRbv14us; | CTCATACTTGTAAGCTCCTTCATCTGGAAATGTG; |
| 145 | 5' TCRbV15us; | CAGAGCCTGAGACAGACAGATGCTTCATTC; |
| 146 | 5' TCRbV17us; | TACTGCACATCAGAACCCATCGCTGG; |
| 147 | 5' TCRbV18us; | TGCAGCAAGTGCCTTTGCCCTG; |
| 148 | 5' TCRbV19us; | CATTCTCTTCCAACAAGTGCTTGGAGCTC; |
| 149 | 5' TCRbV20-1us; | GAGGCAGTGGTCACAACTCTCCCCA; |
| 150 | 5' TCRbV22us; | TCTCTCTCTCTTAGAGCCTGTGTCTGTAACTTCAG; |
| 151 | 5' TCRbV23-1us; | CAGAAAGGGGATGAAAAAGCCTCATCC; |
| 152 | 5' TCRbV24-1us; | ATGCCCTGCTTCCCTCAACATCCAG; |
| 153 | 5' TCRbV25-1us; | CCCATCCTGCTTCCCCACTACTGG; |
| 154 | 5' TCRbV26us; | ATCAGGGACTAAATTCATCACAGCACCAAGC; |
| 155 | 5' TCRbV27us; | ACAGAAACCACCTGGAGCCCCCAG; |

TABLE 3-4

Beta J Outer Primers

| SEQ ID NO: | | |
|---|---|---|
| 156 | 3' TCRbJ1-1 Intron; | TGGACCCACTTTTTCCCTGTGACGG; |
| 157 | 3' TCRbJ1-2 Intron; | CATTTCCCAGGACAGAGTCCTCCCTCAT; |
| 158 | 3' TCRbJ1-3 Intron; | CTGGATTCCAGCCCCTTTTTGCAAG; |
| 159 | 3' TCRbJ1-4 Intron; | GGTCCTCCTGGAACTCCGACCTTATGAT; |
| 160 | 3' TCRbJ1-5 Intron; | AAGCAGAGAACTCTGCCTTCAAGGACAA; |
| 161 | 3' TCRbJ1-6 Intron; | AACTGATCATTGCAGTCAAACCCAGGC; |
| 162 | 3' TCRbJ2-1 Intron; | CGTGCAGGCTGGGCTGCTCAC; |
| 163 | 3' TCRbJ2-2 Intron; | GCCCATCCCGCCCTCTCGG; |
| 164 | 3' TCRbJ2-2P Intron; | CAGACTCAGCTCGGGTCCTTCCCA; |
| 165 | 3' TCRbJ2-3 Intron; | GGGCGCCCCCTCCCCAGT; |
| 166 | 3' TCRbJ2-4 Intron; | GCACAAAACCCGAGCGCAGTCTC; |
| 167 | 3' TCRbJ2-5 Intron; | CAAAAACCAGACCCAAGCCGCC; |
| 168 | 3' TCRbJ2-6 Intron; | CGCCGCCTTCCACCTGAATCC; |
| 169 | 3' TCRbJ2-7 Intron; | CGACTCCGGGGACCGAGGG; |

TABLE 3-5

Alpha V Inner Primers

| SEQ ID NO: | | |
|---|---|---|
| 170 | 5' TCRaV1-2; | GGACAAAACATTGACCAGCCCACTGAGAT; |
| 171 | 5' TCRaV2; | AAGGACCAAGTGTTTCAGCCTTCCACAGTG; |
| 172 | 5' TCRaV3; | CAGTCAGTGGCTCAGCCGGAAGATC; |
| 173 | 5' TCRaV4; | AAGACCACCCAGCCCATCTCCATG; |
| 174 | 5' TCRaV5; | GAGGATGTGGAGCAGAGTCTTTTCCTGAGTG; |
| 175 | 5' TCRaV6; | CAAAAGATAGAACAGAATTCCGAGGCCCTG; |
| 176 | 5' TCRaV7; | GAAAACCAGGTGGAGCACAGCCCTC; |
| 177 | 5' TCRaV8-1; | CAGTCTGTGAGCCAGCATAACCACCAC; |
| 178 | 5' TCRaV8-2; | CAGTCGGTGACCCAGCTTGACAGC; |
| 179 | 5' TCRaV8-3; | CAGTCAGTGACCCAGCCTGACATCCAC; |
| 180 | 5' TCRaV8-4; | CAGTCGGTGACCCAGCTTGGCAG; |
| 181 | 5' TCRaV9-1; | GATTCAGTGGTCCAGACAGAAGGCCAAGT; |
| 182 | 5' TCRaV10; | AAAAACCAAGTGGAGCAGAGTCCTCAGTCC ; |
| 183 | 5' TCRaV12-1; | CAACGGAAGGAGGTGGAGCAGGATC; |
| 184 | 5' TCRaV12-2; | CAACGAAGGAGGTGGAGCAGAATTCTGG; |
| 185 | 5' TCRaV13-1; | GAGAATGTGGAGCAGCATCCTTCAACC; |
| 186 | 5' TCRaV13-2; | GAGAGTGTGGGGCTGCATCTTCCTACC; |
| 187 | 5' TCRaV14D4; | CAGAAGATAACTCAAACCCAACCAGGAATGTTC; |
| 188 | 5' TCRaV9-2; | AATTCAGTGACCCAGATGGAAGGGCC; |
| 189 | 5' TCRaV12-3; | CAACAGAAGGAGGTGGAGCAGGATCCT; |
| 190 | 5' TCRaV8-6; | CAGTCTGTGACCCAGCTTGACAGCCA; |
| 191 | 5' TCRav16; | CAGAGAGTGACTCAGCCCGAGAAGCTC; |
| 192 | 5' T CRaV17; | CAACAGGGAGAAGAGGATCCTCAGGCC; |
| 193 | 5' TCRaV18; | GACTCGGTTACCCAGACAGAAGGCCC; |
| 194 | 5' TCRaV19; | CAGAAGGTAACTCAAGCGCAGACTGAAATTCT; |
| 195 | 5' TCRaV20; | GAAGACCAGGTGACGCAGAGTCCCG; |
| 196 | 5' TCRaV21; | AAACAGGAGGTGACGCAGATTCCTGC; |
| 197 | 5' TCRaV22; | ATACAAGTGGAGCAGAGTCCTCCAGACCTGA; |
| 198 | 5' TCRaV23DV6; | CAACAGAAGGAGAAAAGTGACCAGCAGCA; |
| 199 | 5' TCRaV24; | ATACTGAACGTGGAACAAAGTCCTCAGTCACTG; |
| 200 | 5' TCRaV25; | CAACAGGTAATGCAAATTCCTCAGTACCAGC; |
| 201 | 5' TCRaV26-1; | AAGACCACCCAGCCCCCCTCC; |
| 202 | 5' TCRaV8-7; | CAGTCGGTGACCCAGCTTGATGGC; |
| 203 | 5' TCRaV27; | CAGCTGCTGGAGCAGAGCCCTCAGT; |
| 204 | 5' TCRaV29DV5; | CAACAGAAGAATGATGACCAGCAAGTTAAGCAA; |
| 205 | 5' TCRaV30; | CAACAACCAGTGCAGAGTCCTCAAGCC; |

TABLE 3-5-continued

Alpha V Inner Primers

| SEQ ID NO: | |
|---|---|
| 206 | 5' TCRaV26-2;AAGACCACACAGCCAAATTCAATGGAGAGTAAC; |
| 207 | 5' TCRaV34;CAAGAACTGGAGCAGAGTCCTCAGTCCTTG; |
| 208 | 5' TCRaV35;CAACAGCTGAATCAGAGTCCTCAATCTATGTTTATC; |
| 209 | 5' TCRaV36DV7;GAAGACAAGGTGGTACAAAGCCCTCTATCTCTG; |
| 210 | 5' TCRaV38-2DV8;CAGACAGTCACTCAGTCTCAACCAGAGATGTCT; |
| 211 | 5' TCRaV39;GAGCTGAAAGTGGAACAAAACCCTCTGTTC; |
| 212 | 5' TCRaV40;AATTCAGTCAAGCAGACGGGCCAAATAAC; |
| 213 | 5' TCRaV41;GCCAAAAATGAAGTGGAGCAGAGTCCTC; |

TABLE 3-6

Alpha J Inner Primers

| SEQ ID NO: | |
|---|---|
| 214 | 5' TRAJ1;/5PHOS/AT GGGGAGAAGTGGAAACTCTGGTTCC; |
| 215 | 5' TRAJ2;/5PHOS/AT CAGATATAATGAATACATGGGTCCCTTTCCCA; |
| 216 | 5' TRAJ3;/5PHOS/AT TTGGCCGGATGCTGAGTCTGGTC; |
| 217 | 5' TRAJ4;/5PHOS/AT ATGGGTGTACAGCCAGCCTGGTCCC; |
| 218 | 5' TRAJ5;/5PHOS/AT TTGGTTGCACTTGGAGTCTTGTTCCACTC; |
| 219 | 5' TRAJ6;/5PHOS/AT ACGGATGAACAATAAGGCTGGTTCCTCTTC; |
| 220 | 5' TRAJ7;/5PHOS/AT TTGGTATGACCACCACTTGGTTCCCCTT; |
| 221 | 5' TRAJ8;/5PHOS/AT TTGGACTGACCAGAAGTCGGGTGCC; |
| 222 | 5' TRAJ9;/5PHOS/AT TTGCTTTAACAAATAGTCTTGTTCCTGCTCCAAAG; |
| 223 | 5' TRAJ10;/5PHOS/AT TGAGTTCCACTTTTAGCTGAGTGCCTGTCC; |
| 224 | 5' TRAJ11;/5PHOS/AT CTGGAGAGACTAGAAGCATAGTCCCCTTCCC; |
| 225 | 5' TRAJ12;/5PHOS/AT CAGGCCTGACCAGCAGTCTGGTCC; |
| 226 | 5' TRAJ13;/5PHOS/AT TTGGGATGACTTGGAGCTTTGTTCCAAT; |
| 227 | 5' TRAJ14;/5PHOS/AT CAGGTTTTACTGATAATCTTGTCCCACTCCCA; |
| 228 | 5' TRAJ15;/5PHOS/AT TGGAACTCACTGATAAGGTGGGTTCCCTTC; |
| 229 | 5' TRAJ16;/5PHOS/AT TAAGATCCACCTTTAACATGGTTCCCCTTG; |
| 230 | 5' TRAJ17;/5PHOS/AT TTGGTTTAACTAGCACCCTGGTTCCTCCTC; |
| 231 | 5' TRAJ18;/5PHOS/AT CAGGCCAGACAGTCAACTGAGTTCCTCTTC; |
| 232 | 5' TRAJ19;/5PHOS/AT TTGGAGTGACATTATGTTTGGATCCCTTTCC; |
| 233 | 5' TRAJ20;/5PHOS/AT TTGCTCTTACAGTTACTGTGGTTCCGGCTC; |
| 234 | 5' TRAJ21;/5PHOS/AT TTGGTTTTACATTGAGTTGGTCCCAGATCC; |
| 235 | 5' TRAJ22;/5PHOS/AT CAGGTAAAACAGTCAATTGTGTCCCAGATCC; |
| 236 | 5' TRAJ23;/5PHOS/AT TGGGTTTCACAGATAACTCCGTTCCCTGT; |
| 237 | 5' TRAJ24;/5PHOS/AT CTGGGGTGACCACAACCTGGGTC; |
| 238 | 5' TRAJ25;/5PHOS/AT CTGGGGTGACCACAACCTGGGTC; |
| 239 | 5' TRAJ26;/5PHOS/AT AGGGCAGCACGGACAATCTGGTTC; |
| 240 | 5' TRAJ27;/5PHOS/AT TTGGCTTCACAGTGAGCGTAGTCCCATC; |
| 241 | 5' TRAJ28;/5PHOS/AT TTGGTATGACCGAGAGTTTGGTCCCCTT; |

TABLE 3-6-continued

Alpha J Inner Primers

| SEQ ID NO: | | |
|---|---|---|
| 242 | 5' | TRAJ29;/5PHOS/AT TTGCAATCACAGAAAGTCTTGTGCCCTTTC; |
| 243 | 5' | TRAJ30;/5PHOS/AT TGGGGAGAATATGAAGTCGTGTCCCTTTTC; |
| 244 | 5' | TRAJ31;/5PHOS/AT TGGGCTTCACCACCAGCTGAGTTC; |
| 245 | 5' | TRAJ32;/5PHOS/AT TTGGCTGGACAGCAAGCAGAGTGC; |
| 246 | 5' | TRAJ33;/5PHOS/AT CTGGCTTTATAATTAGCTTGGTCCCAGCG; |
| 247 | 5' | TRAJ34;/5PHOS/AT TTGGAAAGACTTGTAATCTGGTCCCAGTCC; |
| 248 | 5' | TRAJ35;/5PHOS/AT GTGGTAAAACAATCACTTGAGTGCCGGAC; |
| 249 | 5' | TRAJ36;/5PHOS/AT AGGGGAATAACGGTGAGTCTCGTTCCAGT; |
| 250 | 5' | TRAJ37;/5PHOS/AT CTGGTTTTACTTGGTAAAGTTGTCCCTTGCC; |
| 251 | 5' | TRAJ38;/5PHOS/AT TCGGATTTACTGCCAGGCTTGTTCCC; |
| 252 | 5' | TRAJ39;/5PHOS/AT GGGGTTTGACCATTAACCTTGTTCCCC; |
| 253 | 5' | TRAJ40;/5PHOS/AT TTGCTAAAACCTTCAGCCTGGTGCCTG; |
| 254 | 5' | TRAJ41;/5PHOS/AT GGGGTGTGACCAACAGCGAGGTG; |
| 255 | 5' | TRAJ42;/5PHOS/AT TTGGTTTAACAGAGAGTTTAGTGCCTTTTCCAAAGA; |
| 256 | 5' | TRAJ43;/5PHOS/AT TTGGTTTTACTGTCAGTCTGGTCCCTGCTC; |
| 257 | 5' | TRAJ44;/5PHOS/AT CGAGCGTGACCTGAAGTCTTGTTCCAGT; |
| 258 | 5' | TRAJ45;/5PHOS/AT AGGGCTGGATGATTAGATGAGTCCCTTTG; |
| 259 | 5' | TRAJ46;/5PHOS/AT TGGGCCTAACTGCTAAACGAGTCCCG; |
| 260 | 5' | TRAJ47;/5PHOS/AT AGGACTTGACTCTCAGAATGGTTCCTGCG; |
| 261 | 5' | TRAJ48;/5PHOS/AT TGGGTATGATGGTGAGTCTTGTTCCAGTCC; |
| 262 | 5' | TRAJ49;/5PHOS/AT TTGGAATGACCGTCAAACTTGTCCCTGT; |
| 263 | 5' | TRAJ50;/5PHOS/AT TTGGAATGACTGATAAGCTTGTCCCTGGC; |
| 264 | 5' | TRAJ51;/5PHOS/AT TTGGCTTCACAGTTAGTCATGTCTCCTTTCC; |
| 265 | 5' | TRAJ52;/5PHOS/AT TTGGATGGACAGTCAAGATGGTCCCTTG; |
| 266 | 5' | TRAJ53;/5PHOS/AT TTGGATTCACGGTTAAGAGAGTTCCTTTTCC; |

TABLE 3-7

Beta V Inner Primers

| SEQ ID NO: | | |
|---|---|---|
| 267 | 5' | TCRbV2;GAACCTGAAGTCACCCAGACTCCCAGC; |
| 268 | 5' | TCRbV3-1;GCTGTTTCCCAGACTCCAAAATACCTGGTC; |
| 269 | 5' | TCRbV4-1;GAAGTTACCCAGACACCAAAACACCTGGTC; |
| 270 | 5' | TCRbV5-1;GGAGTCACTCAAACTCCAAGATATCTGATCAAAAC; |
| 271 | 5' | TCRbV6-1;GGTGTCACTCAGACCCCAAAATTCCAG; |
| 272 | 5' | TCRbV7-1;GGAGTCTCCCAGTCCCTGAGACACAAGG; |
| 273 | 5' | TCRbV4-2;GGAGTTACGCAGACACCAAGACACCTGG; |
| 274 | 5' | TCRbV6-2;GGTGTCACTCAGACCCCAAAATTCCG; |
| 275 | 5' | TCRbV4-3;GGAGTTACGCAGACACCAAGACACCTGG; |

TABLE 3-7-continued

Beta V Inner Primers

| SEQ ID NO: | | |
|---|---|---|
| 276 | 5' | TCRbV6-3;GGTGTCACTCAGACCCCAAAATTCCG; |
| 277 | 5' | TCRbV7-2;GGAGTCTCCCAGTCCCCCAGTAACAAG; |
| 278 | 5' | TCRbV6-4;GGGATCACCCAGGCACCAACATCTC; |
| 279 | 5' | TCRbV7-3;GGAGTCTCCCAGACCCCCAGTAACAAG; |
| 280 | 5' | TCRbV5-3;GGAGTCACCCAAAGTCCCACACACCT; |
| 281 | 5' | TCRbV9;GGAGTCACACAAACCCCAAAGCACCT; |
| 282 | 5' | TCRbV10-1;GAAATCACCCAGAGCCCAAGACACAAGA; |
| 283 | 5' | TCRbV11-1;GAAGTTGCCCAGTCCCCCAGATATAAGATTA; |
| 284 | 5' | TCRbV10-2;GGAATCACCCAGAGCCCAAGATACAAGAT; |
| 285 | 5' | TCRbV11-2;GGAGTTGCCCAGTCTCCCAGATATAAGATTATAGAG; |
| 286 | 5' | TCRbV6-5;GGTGTCACTCAGACCCCAAAATTCCAG; |
| 287 | 5' | TCRbV7-4;GGAGTCTCCCAGTCCCCAAGGTACAAAG; |
| 288 | 5' | TCRbV5-4;GGAGTCACCCAAAGTCCCACACACCT; |
| 289 | 5' | TCRbV6-6;GGTGTCACTCAGACCCCAAAATTCCG; |
| 290 | 5' | TCRbV7-5;GGAGTCTCCCAGTCCCCAAGGTACGA; |
| 291 | 5' | TCRbV5-5;GGAGTCACCCAAAGTCCCACACACCT; |
| 292 | 5' | TCRbV6-7;GGTGTCACTCAGACCCCAAAATTCCAC; |
| 293 | 5' | TCRbV7-6;GGAGTCTCCCAGTCTCCCAGGTACAAAGTC; |
| 294 | 5' | TCRbV5-6;GGAGTCACCCAAAGTCCCACACACCT; |
| 295 | 5' | TCRbV6-8;GGTGTCACTCAGACCCCAAAATTCCACAT; |
| 296 | 5' | TCRbV7-7;GGAGTCTCCCAGTCTCCCAGGTACAAAGTC; |
| 297 | 5' | TCRbV5-7;GGAGTCACCCAAAGTCCCACACACCT; |
| 298 | 5' | TCRbV6-9;GGTGTCACTCAGACCCCAAAATTCCACAT; |
| 299 | 5' | TCRbV7-8;GGAGTCTCCCAGTCCCTAGGTACAAAGTC; |
| 300 | 5' | TCRbV5-8;GGAGTCACACAAAGTCCCACACACCTGA; |
| 301 | 5' | TCRbV7-9;GGAGTCTCCCAGAACCCCAGACACAAG; |
| 302 | 5' | TCRbV13;GGAGTCATCCAGTCCCCAAGACATCTGAT; |
| 303 | 5' | TCRbV10-3;GGAATCACCCAGAGCCCAAGACACAAG; |
| 304 | 5' | TCRbV11-3;GGAGTGGTTCAGTCTCCCAGATATAAGATTATAGAGAA; |
| 305 | 5' | TCRbV12-3;GGAGTTATCCAGTCACCCCGCCATG; |
| 306 | 5' | TCRbV12-4;GGAGTTATCCAGTCACCCCGGCAC; |
| 307 | 5' | TCRbV12-5;AGAGTCACCCAGACACCAAGGCACAAG; |
| 308 | 5' | TCRbV14;GGAGTTACTCAGTTCCCCAGCCACAGC; |
| 309 | 5' | TCRbV15;ATGGTCATCCAGAACCCAAGATACCAGGTT; |
| 310 | 5' | TCRbV17;GAGCCTGGAGTCAGCCAGACCCC; |
| 311 | 5' | TCRbV18;GGCGTCATGCAGAACCCAAGACAC; |
| 312 | 5' | TCRbV19;GGAATCACTCAGTCCCCAAAGTACCTGTTCA; |
| 313 | 5' | TCRbV20-1;GCTGTCGTCTCTCAACATCCGAGCTG; |

TABLE 3-7-continued

Beta V Inner Primers

| SEQ ID NO: | | |
|---|---|---|
| 314 | 5' | TCRbV22;ATTCCAGCTCACTGGGGCTGGATG; |
| 315 | 5' | TCRbV23-1;AAAGTCACACAGACTCCAGGACATTTGGTCA; |
| 316 | 5' | TCRbV24-1;GATGTTACCCAGACCCCAAGGAATAGGATC; |
| 317 | 5' | TCRbV25-1;GACATCTACCAGACCCCAAGATACCTTGTTATAGG; |
| 318 | 5' | TCRbV26;GTAGTTACACAATTCCCAAGACACAGAATCATTGG; |
| 319 | 5' | TCRbV27;CAAGTGACCCAGAACCCAAGATACCTCATC |

TABLE 3-8

Beta J Inner Primers

| SEQ ID NO: | | |
|---|---|---|
| 320 | 3' | TRBJ1-1;/5PHOS/TCCT CTACAACTGTGAGTCTGGTGCCTTGTCCAAA; |
| 321 | 3' | TRBJ1-2;/5PHOS/TCCT CTACAACGGTTAACCTGGTCCCCGAAC; |
| 322 | 3' | TRBJ1-3;/5PHOS/TCCT CTACAACAGTGAGCCAACTTCCCTCTCCAA; |
| 323 | 3' | TRBJ1-4;/5PHOS/TCCT CCAAGACAGAGAGCTGGGTTCCACTGC; |
| 324 | 3' | TRBJ1-5;/5PHOS/TCCT CTAGGATGGAGAGTCGAGTCCCATCACCA; |
| 325 | 3' | TRBJ1-6;/5PHOS/TCCT CTGTCACAGTGAGCCTGGTCCCGTTC; |
| 326 | 3' | TRBJ2-1;/5PHOS/TCCT CTAGCACGGTGAGCCGTGTCCCTG; |
| 327 | 3' | TRBJ2-2;/5PHOS/TCCT CCAGTACGGTCAGCCTAGAGCCTTCTCC; |
| 328 | 3' | TRBJ2-2P;/5PHOS/TCCT CCAGAACCAGGAGTCCTCCGCCC; |
| 329 | 3' | TRBJ2-3;/5PHOS/TCCT CGAGCACTGTCAGCCGGGTGC; |
| 330 | 3' | TRBJ2-4;/5PHOS/TCCT CCAGCACTGAGAGCCGGGTCCC; |
| 331 | 3' | TRBJ2-5;/5PHOS/TCCT CGAGCACCAGGAGCCGCGTG; |
| 332 | 3' | TRBJ2-6;/5PHOS/TCCT CCAGCACGGTCAGCCTGCTGC; |
| 333 | 3' | TRBJ2-7;/5PHOS/TCCT CTGTGACCGTGAGCCTGGTGCC; |

TABLE 3-9

Alpha V Cloning Primers

| SEQ ID NO: | Primer | Sequence (5'-3') |
|---|---|---|
| 334 | 5' TCRaV1-2 In-Fusion | TACAGGAGGGCTCGG CA GGACAAAACATTGACCAGCCCACTGAGAT |
| 335 | 5' TCRaV2 In-Fusion | TACAGGAGGGCTCGG CA AAGGACCAAGTGTTTCAGCCTTCCACAGTG |
| 336 | 5' TCRaV3 In-Fusion | TACAGGAGGGCTCGG CA CAGTCAGTGGCTCAGCCGGAAGATC |
| 337 | 5' TCRaV4 In-Fusion | TACAGGAGGGCTCGG CA AAGACCACCCAGCCCATCTCCATG |
| 338 | 5' TCRaV5 In-Fusion | TACAGGAGGGCTCGG CA AGGATGTGGAGCAGAGTCTTTTCCTGAGTG |
| 339 | 5' TCRaV6 In-Fusion | TACAGGAGGGCTCGG CA CAAAGATAGAACAGAATTCCGAGGCCCTG |
| 340 | 5' TCRaV7 In-Fusion | TACAGGAGGGCTCGG CA GAAAACCAGGTGGAGCACAGCCCTC |
| 341 | 5' TCRaV8-1 In-Fusion | TACAGGAGGGCTCGG CA CAGTCTGTGAGCCAGCATAACCACCAC |
| 342 | 5' TCRaV8-2 In-Fusion | TACAGGAGGGCTCGG CA CAGTCGGTGACCCAGCTTGACAGC |

TABLE 3-9-continued

Alpha V Cloning Primers

| SEQ ID NO: | Primer | Sequence (5'-3') |
|---|---|---|
| 343 | 5' TCRaV8-3 In-Fusion | TACAGGAGGGCTCGG CA CAGTCAGTGACCCAGCCTGACATCCAC |
| 344 | 5' TCRaV8-4 In-Fusion | TACAGGAGGGCTCGG CA CAGTCGGTGACCCAGCTTGGCAG |
| 345 | 5' TCRaV9-1 In-Fusion | TACAGGAGGGCTCGG CA GATTCAGTGGTCCAGACAGAAGGCCAAGT |
| 346 | 5' TCRaV10 In-Fusion | TACAGGAGGGCTCGG CA AAAAACCAAGTGGAGCAGAGTCCTCAGTCC |
| 347 | 5' TCRaV12-1 In-Fusion | TACAGGAGGGCTCGG CA CAACGGAAGGAGGTGGAGCAGGATC |
| 348 | 5' TCRaV12-2 In-Fusion | TACAGGAGGGCTCGG CA CAACAGAAGGAGGTGGAGCAGAATTCTGG |
| 349 | 5' TCRaV13-1 In-Fusion | TACAGGAGGGCTCGG CA GAGAATGTGGAGCAGCATCCTTCAACC |
| 350 | 5' TCRaV13-2 In-Fusion | TACAGGAGGGCTCGG CA GAGAGTGTGGGGCTGCATCTTCCTACC |
| 351 | 5' TCRaV14D4In-Fusion | TACAGGAGGGCTCGGCACAGAAGATAACTCAAACCCAACCAGGAATGTTC |
| 352 | 5' TCRaV9-2 In-FusionT | ACAGGAGGGCTCGG CA AATTCAGTGACCCAGATGGAAGGGCC |
| 353 | 5' TCRaV12-3 In-Fusion | TACAGGAGGGCTCGG CA CAACAGAAGGAGGTGGAGCAGGATCCT |
| 354 | 5' TCRaV8-6 In-Fusion | TACAGGAGGGCTCGG CA CAGTCTGTGACCCAGCTTGACAGCCA |
| 355 | 5' TCRav16 In-Fusion | TACAGGAGGGCTCGG CA CAGAGAGTGACTCAGCCCGAGAAGCTC |
| 356 | 5' TCRaV17 In-Fusion | TACAGGAGGGCTCGG CA CAACAGGGAGAAGAGGATCCTCAGGCC |
| 357 | 5' TCRaV18 In-Fusion | TACAGGAGGGCTCGG CA GACTCGGTTACCCAGACAGAAGGCCC |
| 358 | 5' TCRaV19 In-Fusion | TACAGGAGGGCTCGGCACAGAAGGTAACTCAAGCGCAGACTGAAATTTCT |
| 359 | 5' TCRaV20 In-Fusion | TACAGGAGGGCTCGG CA GAAGACCAGGTGACGCAGAGTCCCG |
| 360 | 5' TCRaV21 In-Fusion | TACAGGAGGGCTCGG CA AAACAGGAGGTGACGCAGATTCCTGC |
| 361 | 5' TCRaV22 In-Fusion | TACAGGAGGGCTCGG CA ATACAAGTGGAGCAGAGTCCTCCAGACCTGA |
| 362 | 5' TCRaV23DV6In-Fusion | TACAGGAGGGCTCGG CA CAACAGAAGGAGAAAAGTGACCAGCAGCA |
| 363 | 5' TCRaV24 In-Fusion | TACAGGAGGGCTCGGCATACTGAACGTGGAACAAAGTCCTCAGTCACTG |
| 364 | 5' TCRaV25 In-Fusion | TACAGGAGGGCTCGG CA CAACAGGTAATGCAAATTCCTCAGTACCAGC |
| 365 | 5' TCRaV26-1 In-Fusion | TACAGGAGGGCTCGG CA AAGACCACCCAGCCCCCCTCC |
| 366 | 5' TCRaV8-7 In-Fusion | TACAGGAGGGCTCGG CA CAGTCGGTGACCCAGCTTGATGGC |
| 367 | 5' TCRaV27 In-Fusion | TACAGGAGGGCTCGG CA CAGCTGCTGGAGCAGAGCCCTCAGT |
| 368 | 5' TCRaV29DV5In-Fusion | TACAGGAGGGCTCGG CA CAACAGAAGAATGATGACCAGCAAGTTAAGCAA |
| 369 | 5' TCRaV30 In-Fusion | TACAGGAGGGCTCGG CA CAACAACCAGTGCAGAGTCCTCAAGCC |
| 370 | 5' TCRaV26-2 In-Fusion | TACAGGAGGGCTCGGCA AGACCACACAGCCAAATTCAATGGAGAGTAAC |
| 371 | 5' TCRaV34 In-Fusion | TACAGGAGGGCTCGG CA CAAGAACTGGAGCAGAGTCCTCAGTCCTTG |
| 372 | 5' TCRaV35 In-Fusion | TACAGGAGGGCTCGGCACAACAGCTGAATCAGAGTCCTCAATCTATGTTTATC |
| 373 | 5' TCRaV36DV7 In-Fusion | TACAGGAGGGCTCGGCA AAGACAAGGTGGTACAAAGCCCTCTATCTCTG |
| 374 | 5' TCRaV382DV8InFusion | TACAGGAGGGCTCGGCA AGACAGTCACTCAGTCTCAACCAGAGATGTCT |
| 375 | 5' TCRaV39 In-Fusion | TACAGGAGGGCTCGG CA GAGCTGAAAGTGGAACAAAACCCTCTGTTC |
| 376 | 5' TCRaV40 In-Fusion | TACAGGAGGGCTCGG CA AATTCAGTCAAGCAGACGGGCCAAATAAC |
| 377 | 5' TCRaV41 In-Fusion | TACAGGAGGGCTCGG CA GCCAAAAATGAAGTGGAGCAGAGTCCTC |

TABLE 3-10

Alpha J Cloning Primers

| SEQ ID NO: | Primer | Sequence (5'-3') |
|---|---|---|
| 378 | 5' TRAJ1 In-Fusion | GTCAGGGTTCTGGATAT GGGGAGAAGTGGAAACTCTGGTTCC |
| 379 | 5' TRAJ2 In-Fusion | GTCAGGGTTCTGGATAT CAGATATAATGAATACATGGGTCCCTTTCCCA |
| 380 | 5' TRAJ3 In-Fusion | GTCAGGGTTCTGGATAT TTGGCCGGATGCTGAGTCTGGTC |
| 381 | 5' TRAJ4 In-Fusion | GTCAGGGTTCTGGATAT ATGGGTGTACAGCCAGCCTGGTCCC |
| 382 | 5' TRAJ5 In-Fusion | GTCAGGGTTCTGGATAT TTGGTTGCACTTGGAGTCTTGTTCCACTC |
| 383 | 5' TRAJ6 In-Fusion | GTCAGGGTTCTGGATAT ACGGATGAACAATAAGGCTGGTTCCTCTTC |
| 384 | 5' TRAJ7 In-Fusion | GTCAGGGTTCTGGATAT TTGGTATGACCACCACTTGGTTCCCCTT |
| 385 | 5' TRAJ8 In-Fusion | GTCAGGGTTCTGGATAT TTGGACTGACCAGAAGTCGGGTGCC |
| 386 | 5' TRAJ9 In-Fusion | GTCAGGGTTCTGGATAT TTGCTTTAACAAATAGTCTTGTTCCTGCTCCAAAG |
| 387 | 5' TRAJ10 In-Fusion | GTCAGGGTTCTGGATAT TGAGTTCCACTTTTAGCTGAGTGCCTGTCC |
| 388 | 5' TRAJ11 In-Fusion | GTCAGGGTTCTGGATAT CTGGAGAGACTAGAAGCATAGTCCCCTTCCC |
| 389 | 5' TRAJ12 In-Fusion | GTCAGGGTTCTGGATAT CAGGCCTGACCAGCAGTCTGGTCC |
| 390 | 5' TRAJ13 In-Fusion | GTCAGGGTTCTGGATAT TTGGGATGACTTGGAGCTTTGTTCCAAT |
| 391 | 5' TRAJ14 In-Fusion | GTCAGGGTTCTGGATAT CAGGTTTTACTGATAATCTTGTCCCACTCCCA |
| 392 | 5' TRAJ15 In-Fusion | GTCAGGGTTCTGGATAT TGGAACTCACTGATAAGGTGGGTTCCCTTC |
| 393 | 5' TRAJ16 In-Fusion | GTCAGGGTTCTGGATAT TAAGATCCACCTTTAACATGGTTCCCCTTG |
| 394 | 5' TRAJ17 In-Fusion | GTCAGGGTTCTGGATAT TTGGTTTAACTAGCACCCTGGTTCCTCCTC |
| 395 | 5' TRAJ18 In-Fusion | GTCAGGGTTCTGGATAT CAGGCCAGACAGTCAACTGAGTTCCTCTTC |
| 396 | 5' TRAJ19 In-Fusion | GTCAGGGTTCTGGATAT TTGGAGTGACATTATGTTTGGATCCCTTTCC |
| 397 | 5' TRAJ20 In-Fusion | GTCAGGGTTCTGGATAT TTGCTCTTACAGTTACTGTGGTTCCGGCTC |
| 398 | 5' TRAJ21 In-Fusion | GTCAGGGTTCTGGATAT TTGGTTTTACATTGAGTTTGGTCCCAGATCC |
| 399 | 5' TRAJ22 In-Fusion | GTCAGGGTTCTGGATAT CAGGTAAAACAGTCAATTGTGTCCCAGATCC |
| 400 | 5' TRAJ23 In-Fusion | GTCAGGGTTCTGGATAT TGGGTTTCACAGATAACTCCGTTCCCTGT |
| 401 | 5' TRAJ24 In-Fusion | GTCAGGGTTCTGGATAT CTGGGGTGACCACAACCTGGGTC |
| 402 | 5' TRAJ25 In-Fusion | GTCAGGGTTCTGGATAT CTGGGGTGACCACAACCTGGGTC |
| 403 | 5' TRAJ26 In-Fusion | GTCAGGGTTCTGGATAT AGGGCAGCACGGACAATCTGGTTC |
| 404 | 5' TRAJ27 In-Fusion | GTCAGGGTTCTGGATAT TTGGCTTCACAGTGAGCGTAGTCCCATC |
| 405 | 5' TRAJ28 In-Fusion | GTCAGGGTTCTGGATAT TTGGTATGACCGAGAGTTTGGTCCCCTT |
| 406 | 5' TRAJ29 In-Fusion | GTCAGGGTTCTGGATAT TTGCAATCACAGAAAGTCTTGTGCCCTTTC |
| 407 | 5' TRAJ30 In-Fusion | GTCAGGGTTCTGGATAT TGGGGAGAATATGAAGTCGTGTCCCTTTTC |
| 408 | 5' TRAJ31 In-Fusion | GTCAGGGTTCTGGATAT TGGGCTTCACCACCAGCTGAGTTC |
| 409 | 5' TRAJ32 In-Fusion | GTCAGGGTTCTGGATAT TTGGCTGGACAGCAAGCAGAGTGC |
| 410 | 5' TRAJ33 In-Fusion | GTCAGGGTTCTGGATAT CTGGCTTTATAATTAGCTTGGTCCCAGCG |
| 411 | 5' TRAJ34 In-Fusion | GTCAGGGTTCTGGATAT TTGGAAAGACTTGTAATCTGGTCCCAGTCC |
| 412 | 5' TRAJ35 In-Fusion | GTCAGGGTTCTGGATAT GTGGTAAAACAATCACTTGAGTGCCGGAC |
| 413 | 5' TRAJ36 In-Fusion | GTCAGGGTTCTGGATAT AGGGGAATAACGGTGAGTCTCGTTCCAGT |
| 414 | 5' TRAJ37 In-Fusion | GTCAGGGTTCTGGATAT CTGGTTTTACTTGGTAAAGTTGTCCCTTGCC |
| 415 | 5' TRAJ38 In-Fusion | GTCAGGGTTCTGGATAT TCGGATTTACTGCCAGGCTTGTTCCC |

TABLE 3-10-continued

Alpha J Cloning Primers

| SEQ ID NO: | Primer | Sequence (5'-3') |
|---|---|---|
| 416 | 5' TRAJ39 In-Fusion | GTCAGGGTTCTGGATAT GGGGTTTGACCATTAACCTTGTTCCCC |
| 417 | 5' TRAJ40 In-Fusion | GTCAGGGTTCTGGATAT TTGCTAAAACCTTCAGCCTGGTGCCTG |
| 418 | 5' TRAJ41 In-Fusion | GTCAGGGTTCTGGATAT GGGGTGTGACCAACAGCGAGGTG |
| 419 | 5' TRAJ42 In-Fusion | GTCAGGGTTCTGGATATTTGGTTTAACAGAGAGTTTAGTGCCTTTTCCAAAGA |
| 420 | 5' TRAJ43 In-Fusion | GTCAGGGTTCTGGATAT TTGGTTTTACTGTCAGTCTGGTCCCTGCTC |
| 421 | 5' TRAJ44 In-Fusion | GTCAGGGTTCTGGATAT CGAGCGTGACCTGAAGTCTTGTTCCAGT |
| 422 | 5' TRAJ45 In-Fusion | GTCAGGGTTCTGGATAT AGGGCTGGATGATTAGATGAGTCCCTTTG |
| 423 | 5' TRAJ46 In-Fusion | GTCAGGGTTCTGGATAT TGGGCCTAACTGCTAAACGAGTCCCG |
| 424 | 5' TRAJ47 In-Fusion | GTCAGGGTTCTGGATAT AGGACTTGACTCTCAGAATGGTTCCTGCG |
| 425 | 5' TRAJ48 In-Fusion | GTCAGGGTTCTGGATAT TGGGTATGATGGTGAGTCTTGTTCCAGTCC |
| 426 | 5' TRAJ49 In-Fusion | GTCAGGGTTCTGGATAT TTGGAATGACCGTCAAACTTGTCCCTGT |
| 427 | 5' TRAJ50 In-Fusion | GTCAGGGTTCTGGATAT TTGGAATGACTGATAAGCTTGTCCCTGGC |
| 428 | 5' TRAJ51 In-Fusion | GTCAGGGTTCTGGATAT TTGGCTTCACAGTTAGTCATGTCTCCTTTCC |
| 429 | 5' TRAJ52 In-Fusion | GTCAGGGTTCTGGATAT TTGGATGGACAGTCAAGATGGTCCCTTG |
| 430 | 5' TRAJ53 In-Fusion | GTCAGGGTTCTGGATAT TTGGATTCACGGTTAAGAGAGTTCCTTTTCC |
| 431 | 5' TRAJ54 In-Fusion | GTCAGGGTTCTGGATAT TTGGGTTGATAGTCAGCCTGGTTCCTTG |
| 432 | 5' TRAJ55 In-Fusion | GTCAGGGTTCTGGATAT TTGGATTTATTTTTGTACTCATCCCCTTTCCC |
| 433 | 5' TRAJ56 In-Fusion | GTCAGGGTTCTGGATATCTGGTCTAACACTCAGAGTTATTCCTTTTCCAAATGTC |
| 434 | 5' TRAJ57 In-Fusion | GTCAGGGTTCTGGATAT ATGGGTTTACTGTCAGTTTCGTTCCCTTTCC |
| 435 | 5' TRAJ58 In-Fusion | GTCAGGGTTCTGGATAT CAGGATTCACTGTGAGCTGTGTTCCTTCC |
| 436 | 5' TRAJ59 In-Fusion | GTCAGGGTTCTGGATAT TCACTCTCACTTGCGTCCCCATTCC |
| 437 | 5' TRAJ60 In-Fusion | GTCAGGGTTCTGGATAT CCAGGCTCACAATTAACTCAGTCCCCTTC |
| 438 | 5' TRAJ61 In-Fusion | GTCAGGGTTCTGGATAT TGAGTTTCATGATTCCTCTAGTGTTGGCTCC |

TABLE 3-11

Beta V Cloning Primers

| SEQ ID NO: | Primer | Sequence (5'-3') |
|---|---|---|
| 439 | 5' TCRbV2 In-Fusion | CAAGAGGGCTCGGCA GAACCTGAAGTCACCCAGACTCCCAGC |
| 440 | 5' TCRbV3-1 In-Fusion | CAAGAGGGCTCGGCA GCTGTTTCCCAGACTCCAAAATACCTGGTC |
| 441 | 5' TCRbV4-1 In-Fusion | CAAGAGGGCTCGGCA GAAGTTACCCAGACACCAAAACACCTGGTC |
| 442 | 5' TCRbV5-1 In-Fusion | CAAGAGGGCTCGGCA GGAGTCACTCAAACTCCAAGATATCTGATCAAAAC |
| 443 | 5' TCRbV6-1 In-Fusion | CAAGAGGGCTCGGCA GGTGTCACTCAGACCCCAAAATTCCAG |
| 444 | 5' TCRbV7-1 In-Fusion | CAAGAGGGCTCGGCA GGAGTCTCCCAGTCCCTGAGACACAAGG |
| 445 | 5' TCRbV4-2 In-Fusion | CAAGAGGGCTCGGCA GGAGTTACGCAGACACCAAGACACTGG |
| 446 | 5' TCRbV6-2 In-Fusion | CAAGAGGGCTCGGCA GGTGTCACTCAGACCCCAAAATTCCG |
| 447 | 5' TCRbV4-3 In-Fusion | CAAGAGGGCTCGGCA GGAGTTACGCAGACACCAAGACACTGG |
| 448 | 5' TCRbV6-3 In-Fusion | CAAGAGGGCTCGGCA GGTGTCACTCAGACCCCAAAATTCCG |

TABLE 3-11-continued

Beta V Cloning Primers

| SEQ ID NO: | Primer | Sequence (5'-3') |
|---|---|---|
| 449 | 5' TCRbV7-2 In-Fusion | CAAGAGGGCTCGGCA GGAGTCTCCCAGTCCCCCAGTAACAAG |
| 450 | 5' TCRbV6-4 In-Fusion | CAAGAGGGCTCGGCA GGGATCACCCAGGCACCAACATCTC |
| 451 | 5' TCRbV7-3 In-Fusion | CAAGAGGGCTCGGCA GGAGTCTCCCAGACCCCCAGTAACAAG |
| 452 | 5' TCRbV5-3 In-Fusion | CAAGAGGGCTCGGCA GGAGTCACCCAAAGTCCCACACACCT |
| 453 | 5' TCRbV9 In-Fusion | CAAGAGGGCTCGGCA GGAGTCACACAAACCCCAAAGCACCT |
| 454 | 5' TCRbV10-1In-Fusion | CAAGAGGGCTCGGCA GAAATCACCCAGAGCCCAAGACACAAGA |
| 455 | 5' TCRbV11-1In-Fusion | CAAGAGGGCTCGGCA GAAGTTGCCCAGTCCCCCAGATATAAGATTA |
| 456 | 5' TCRbV10-2In-Fusion | CAAGAGGGCTCGGCA GGAATCACCCAGAGCCCAAGATACAAGAT |
| 457 | 5' TCRbV11-2In-Fusion | CAAGAGGGCTCGGCA GGAGTTGCCCAGTCTCCCAGATATAAGATTATAGAG |
| 458 | 5' TCRbV6-5 In-Fusion | CAAGAGGGCTCGGCA GGTGTCACTCAGACCCCAAAATTCCAG |
| 459 | 5' TCRbV7-4 In-Fusion | CAAGAGGGCTCGGCA GGAGTCTCCCAGTCCCCAAGGTACAAAG |
| 460 | 5' TCRbV5-4 In-Fusion | CAAGAGGGCTCGGCA GGAGTCACCCAAAGTCCCACACACCT |
| 461 | 5' TCRbV6-6 In-Fusion | CAAGAGGGCTCGGCA GGTGTCACTCAGACCCCAAAATTCCG |
| 462 | 5' TCRbV7-5 In-Fusion | CAAGAGGGCTCGGCA GGAGTCTCCCAGTCCCCAAGGTACGA |
| 463 | 5' TCRbV5-5 In-Fusion | CAAGAGGGCTCGGCA GGAGTCACCCAAAGTCCCACACACCT |
| 464 | 5' TCRbV6-7 In-Fusion | CAAGAGGGCTCGGCA GGTGTCACTCAGACCCCAAAATTCCAC |
| 465 | 5' TCRbV7-6 In-Fusion | CAAGAGGGCTCGGCA GGAGTCTCCCAGTCTCCCAGGTACAAAGTC |
| 466 | 5' TCRbV5-6 In-Fusion | CAAGAGGGCTCGGCA GGAGTCACCCAAAGTCCCACACACCT |
| 467 | 5' TCRbV6-8 In-Fusion | CAAGAGGGCTCGGCA GGTGTCACTCAGACCCCAAAATTCCACAT |
| 468 | 5' TCRbV7-7 In-Fusion | CAAGAGGGCTCGGCA GGAGTCTCCCAGTCTCCCAGGTACAAAGTC |
| 469 | 5' TCRbV5-7 In-Fusion | CAAGAGGGCTCGGCA GGAGTCACCCAAAGTCCCACACACCT |
| 470 | 5' TCRbV6-9 In-Fusion | CAAGAGGGCTCGGCA GGTGTCACTCAGACCCCAAAATTCCACAT |
| 471 | 5' TCRbV7-8 In-Fusion | CAAGAGGGCTCGGCA GGAGTCTCCCAGTCCCCTAGGTACAAAGTC |
| 472 | 5' TCRbV5-8 In-Fusion | CAAGAGGGCTCGGCA GGAGTCACACAAAGTCCCACACACCTGA |
| 473 | 5' TCRbV7-9 In-Fusion | CAAGAGGGCTCGGCA GGAGTCTCCCAGAACCCCAGACACAAG |
| 474 | 5' TCRbV13 In-Fusion | CAAGAGGGCTCGGCA GGAGTCATCCAGTCCCCAAGACATCTGAT |
| 475 | 5' TCRbV10-3In-Fusion | CAAGAGGGCTCGGCA GGAATCACCCAGAGCCCAAGACACAAG |
| 476 | 5' TCRbV11-3In-Fusion | CAAGAGGGCTCGGCAGGAGTGGTTCAGTCTCCCAGATATAAGATTATAGAGAA |
| 477 | 5' TCRbV12-3In-Fusion | CAAGAGGGCTCGGCA GGAGTTATCCAGTCACCCCGCCATG |
| 478 | 5' TCRbV12-4In-Fusion | CAAGAGGGCTCGGCA GGAGTTATCCAGTCACCCCGGCAC |
| 479 | 5' TCRbV12-5In-Fusion | CAAGAGGGCTCGGCA AGAGTCACCCAGACACCAAGGCACAAG |
| 480 | 5' TCRbV14 In-Fusion | CAAGAGGGCTCGGCA GGAGTTACTCAGTTCCCCAGCCACAGC |
| 481 | 5' TCRbV15 In-Fusion | CAAGAGGGCTCGGCA ATGGTCATCCAGAACCCAAGATACCAGGTT |
| 482 | 5' TCRbV17 In-Fusion | CAAGAGGGCTCGGCA GAGCCTGGAGTCAGCCAGACCCC |
| 483 | 5' TCRbV18 In-Fusion | CAAGAGGGCTCGGCA GGCGTCATGCAGAACCCAAGACAC |
| 484 | 5' TCRbV19 In-Fusion | CAAGAGGGCTCGGCA GGAATCACTCAGTCCCCAAAGTACCTGTTCA |
| 485 | 5' TCRbV20-1In-Fusion | CAAGAGGGCTCGGCA GCTGTCGTCTCTCAACATCCGAGCTG |
| 486 | 5' TCRbV22 In-Fusion | CAAGAGGGCTCGGCA ATTCCAGCTCACTGGGGCTGGATG |

TABLE 3-11-continued

Beta V Cloning Primers

| SEQ ID NO: | Primer | Sequence (5'-3') |
|---|---|---|
| 487 | 5' TCRbV23-1In-Fusion | CAAGAGGGCTCGGCA AAAGTCACACAGACTCCAGGACATTTGGTCA |
| 488 | 5' TCRbV24-1In-Fusion | CAAGAGGGCTCGGCA GATGTTACCCAGACCCCAAGGAATAGGATC |
| 489 | 5' TCRbV25-1In-Fusion | CAAGAGGGCTCGGCA GACATCTACCAGACCCCAAGATACCTTGTTATAGG |
| 490 | 5' TCRbV26 In-Fusion | CAAGAGGGCTCGGCA GTAGTTACACAATTCCCAAGACACAGAATCATTGG |
| 491 | 5' TCRbV27 In-Fusion | CAAGAGGGCTCGGCA CAAGTGACCCAGAACCCAAGATACCTCATC |
| 492 | 5' TCRbV28 In-Fusion | CAAGAGGGCTCGGCA TCGAGATATCTAGTCAAAAGGACGGGAGAGAAA |
| 493 | 5' TCRbV29-1In-Fusion | CAAGAGGGCTCGGCA GCTGTCATCTCTCAAAAGCCAAGCAGG |

TABLE 3-12

Beta J Cloning Primers

| SEQ ID NO: | Primer | Sequence (5'-3') |
|---|---|---|
| 494 | 3' TRBJ1-1 In-Fusion | AACACCTTGTTCAGGTCCT CTACAACTGTGAGTCTGGTGCCTTGTCCAAA |
| 495 | 3' TRBJ1-2 In-Fusion | AACACCTTGTTCAGGTCCT CTACAACGGTTAACCTGGTCCCCGAAC |
| 496 | 3' TRBJ1-3 In-Fusion | AACACCTTGTTCAGGTCCT CTACAACAGTGAGCCAACTTCCCTCTCCAA |
| 497 | 3' TRBJ1-4 In-Fusion | AACACCTTGTTCAGGTCCT CCAAGACAGAGAGCTGGGTTCCACTGC |
| 498 | 3' TRBJ1-5 In-Fusion | AACACCTTGTTCAGGTCCT CTAGGATGGAGAGTCGAGTCCCATCACCA |
| 499 | 3' TRBJ1-6 In-Fusion | AACACCTTGTTCAGGTCCT CTGTCACAGTGAGCCTGGTCCCGTTC |
| 500 | 3' TRBJ2-1 In-Fusion | AACACCTTGTTCAGGTCCT CTAGCACGGTGAGCCGTGTCCCTG |
| 501 | 3' TRBJ2-2 In-Fusion | AACACCTTGTTCAGGTCCT CCAGTACGGTCAGCCTAGAGCCTTCTCC |
| 502 | 3' TRBJ2-2P In-Fusion | AACACCTTGTTCAGGTCCT CCAGAACCAGGAGTCCTCCGCCC |
| 503 | 3' TRBJ2-3 In-Fusion | AACACCTTGTTCAGGTCCT CGAGCACTGTCAGCCGGGTGC |
| 504 | 3' TRBJ2-4 In-Fusion | AACACCTTGTTCAGGTCCT CCAGCACTGAGAGCCGGGTCCC |
| 505 | 3' TRBJ2-5 In-Fusion | AACACCTTGTTCAGGTCCT CGAGCACCAGGAGCCGCGTG |
| 506 | 3' TRBJ2-6 In-Fusion | AACACCTTGTTCAGGTCCT CCAGCACGGTCAGCCTGCTGC |
| 507 | 3' TRBJ2-7 In-Fusion | AACACCTTGTTCAGGTCCT CTGTGACCGTGAGCCTGGTGCC |

TABLE 3-13

Homologous Primers

| SEQ ID NO: | Primer | Sequence (5'-3') |
|---|---|---|
| 508 | 5' Alpha Ext-Universal In-Fusion | CGTGGT TACAGGAGGGCTCGGCA |
| 509 | 3' Alpha Ext-Universal In-Fusion | CACGGCAGG GTCAGGGTTCTGGATAT |
| 510 | 5' Beta Ext-Universal In-Fusion | TGGCTC AAGAGGGCTCGGCA |
| 511 | 3' Beta Ext-Universal In-Fusion | GGGTGGG AACACCTTGTTCAGGTCCT |

TABLE 3-14

TCR Isolation PCR Protocols

| Step | Temperature | Time |
|---|---|---|
| Protocol for Outer Primers (round 1) | | |
| 1 | 95° C. | 30 sec |
| 2 | 77° C. | 45 sec |
| 3 | 77° C. | 30 sec |
| 4 | 95° C. | 30 sec |
| 5 | 76° C. | 45 sec |
| 6 | 76° C. | 30 sec |
| 7 | 95° C. | 30 sec |
| 8 | 75° C. | 45 sec |
| 9 | 75° C. | 30 sec |
| 10 | 95° C. | 30 sec |
| 11 | 74° C. | 45 sec |
| 12 | 74° C. | 30 sec |
| 13 | 95° C. | 30 sec |
| 14 | 73° C. | 45 sec |
| 15 | 73° C. | 30 sec |
| 16 | 95° C. | 30 sec |
| 17 | 72° C. | 45 sec |
| 18 | 72° C. | 30 sec |
| 19 | 95° C. | 30 sec |
| 20 | 71° C. | 45 sec |
| 21 | 71° C. | 30 sec |
| 22 | 95° C. | 30 sec |
| 23 | 70° C. | 45 sec |
| 24 | 70° C. | 30 sec |
| 25 | 95° C. | 30 sec |
| 26 | 69° C. | 45 sec |
| 27 | 70° C. | 30 sec |
| 28 | 95° C. | 30 sec |
| 29 | 68° C. | 45 sec |
| 30 | 70° C. | 30 sec |
| 31 | 95° C. | 30 sec |
| 32 | 67° C. | 45 sec |
| 33 | 70° C. | 30 sec |
| 34 | 95° C. | 30 sec |
| 35 | 66° C. | 45 sec |
| 36 | 70° C. | 30 sec |
| Protocol for Inner Primers (round 2) | | |
| 1 | 95° C. | 30 sec |
| 2 | 77° C. | 4:00 min |
| 3 | 77° C. | 30 sec |
| 4 | 95° C. | 30 sec |
| 5 | 76° C. | 4:00 min |
| 6 | 76° C. | 30 sec |
| 7 | 95° C. | 30 sec |
| 8 | 75° C. | 4:00 min |
| 9 | 75° C. | 30 sec |
| 10 | 95° C. | 30 sec |
| 11 | 74° C. | 4:00 min |
| 12 | 74° C. | 30 sec |
| 13 | 95° C. | 30 sec |
| 14 | 73° C. | 4:00 min |
| 15 | 73° C. | 30 sec |
| 16 | 95° C. | 30 sec |
| 17 | 72° C. | 4:00 min |
| 18 | 72° C. | 30 sec |
| 19 | 95° C. | 30 sec |
| 20 | 71° C. | 4:00 min |
| 21 | 71° C. | 30 sec |
| 22 | 95° C. | 30 sec |
| 23 | 70° C. | 4:00 min |
| 24 | 70° C. | 30 sec |
| 25 | 95° C. | 30 sec |
| 26 | 69° C. | 4:00 min |
| 27 | 70° C. | 30 sec |
| 28 | 95° C. | 30 sec |
| 29 | 68° C. | 4:00 min |
| 30 | 70° C. | 30 sec |
| 31 | 95° C. | 30 sec |
| 32 | 67° C. | 4:00 min |
| 33 | 70° C. | 30 sec |
| 34 | 95° C. | 30 sec |
| 35 | 66° C. | 4:00 min |
| 36 | 70° C. | 30 sec |
| Protocol for Cloning Primers (round 3) | | |
| 1 | 95° C. | 30 sec |
| 2 | 77° C. | 4:00 min |
| 3 | 77° C. | 30 sec |
| 4 | 95° C. | 30 sec |
| 5 | 76° C. | 4:00 min |
| 6 | 76° C. | 30 sec |
| 7 | 95° C. | 30 sec |
| 8 | 75° C. | 4:00 min |
| 9 | 75° C. | 30 sec |
| 10 | 95° C. | 30 sec |
| 11 | 74° C. | 4:00 min |
| 12 | 74° C. | 30 sec |
| 13 | 95° C. | 30 sec |
| 14 | 73° C. | 4:00 min |
| 15 | 73° C. | 30 sec |
| 16 | 95° C. | 30 sec |
| 17 | 72° C. | 4:00 min |
| 18 | 72° C. | 30 sec |
| 19 | 95° C. | 30 sec |
| 20 | 71° C. | 4:00 min |
| 21 | 71° C. | 30 sec |
| 22 | 95° C. | 30 sec |
| 23 | 70° C. | 4:00 min |
| 24 | 70° C. | 30 sec |
| 25 | 95° C. | 30 sec |
| 26 | 69° C. | 4:00 min |
| 27 | 70° C. | 30 sec |
| 28 | 95° C. | 30 sec |
| 29 | 68° C. | 4:00 min |
| 30 | 70° C. | 30 sec |
| 31 | 95° C. | 30 sec |
| 32 | 67° C. | 4:00 min |
| 33 | 70° C. | 30 sec |
| Protocol for Homologous Primers (round 4) | | |
| 1 | 95° C. | 2:00 min |
| 2 | 95° C. | 20 sec |
| 3 | 65° C. | 10 sec |
| 4 | 70° C. | 10 sec |
| Go to Step 4 and Repeat 45 Cycles | | |
| 5 | 4° C. | Hold |

Example 4

NA-17 TCR Isolation

NA-17 is a melanoma-specific antigen. T Cells were obtained from a patient sample and stained with an NY-ESO specific tetramer. Genomic DNA from eight NA-17$^+$ CD3$^+$ cells was amplified and used as template for a TCR isolation protocol. These cells yielded four distinct alpha chains and five distinct beta chains: TRAV12-1J11, TRAV12-3J9, TRAV16J28, TRAV17J10, TRBV12-3J1-6, TRBV27J1-2, TRBV27J1-6, TRBV5-5J1-3, TRBV5-6J1-1. Some chains were found to be expressed in multiple cells. Without subscribing to any one theory, these results may indicate that the cells were clonal or that individual wells contained multiple cells, making pairing ambiguous.

What is claimed is:

1. A method of isolating DNA encoding the variable regions of a T cell receptor (TCR) alpha or beta chain, said method comprising: (a) isolating genomic DNA from a single T cell; (b) amplifying a gene segment encompassing the TCR alpha or beta chain variable region by an enrichment amplification reaction to produce an enrichment product comprising the V and J regions of the TCR alpha or beta chain from the single cell, the amplification reaction comprising incubating the isolated genomic DNA with a set of outer primers comprising at least one primer complementary to each of the V and J regions of the TCR alpha chain or TCR beta chain.

2. The method of claim 1 wherein the enrichment product is further amplified in an isolation amplification reaction to produce an isolation product, the isolation amplification reaction comprising incubating the enrichment product with a set of inner primers comprising at least one primer complementary to each of the V and J regions of the TCR alpha chain or TCR beta chain.

3. The method of claim 2 wherein the isolation product is further amplified in a cloning amplification reaction to produce a cloning product, the cloning amplification reaction comprising incubating the isolation product with a set of cloning primers comprising at least one primer complementary to each of the V and J regions of the TCR alpha chain or TCR beta chain, and wherein each cloning primer also comprises a vector region that is homologous to a vector.

4. The method of claim 3 wherein the cloning product is further amplified in a homologous amplification reaction to produce a homologous product, the homologous amplification reaction comprising incubating the cloning product with a set of homologous primers that are homologous to the vector region of the cloning primers.

5. The method of claim 1 wherein the amplification reaction comprises a PCR reaction.

6. The method of claim 5, wherein the PCR reaction utilizes a touchdown PCR protocol.

7. The method of claim 1, wherein isolating genomic DNA from a single T cell comprises whole genome amplification.

8. The method of claim 1 additionally comprising screening the isolated genomic DNA obtained in step (a) for the presence of T cell receptor constant regions prior to step (b).

9. The method of claim 1, wherein the outer primers anneal to a sequence about 5 to 40 base pairs upstream of the signal sequence junction of the alpha or beta V region or a sequence about 5 to 50 base pairs downstream of the exon/intron junction of the alpha or beta J region.

10. The method of claim 2, wherein the set of inner primers comprises forward and reverse inner primers, wherein each forward inner primer anneals to a sequence at the start of the first amino acid downstream of the signal sequence of the alpha or beta V region and each reverse inner primer anneals to a sequence at the downstream end of the alpha or beta J region.

11. The method of claim 3, wherein the vector region comprises about 15 bases of homology to the vector.

12. The method of claim 2, additionally comprising sequencing the isolation product.

13. The method of claim 3, additionally comprising inserting the cloning product into the vector.

14. The method of claim 13, wherein the vector is an expression vector.

15. A method of isolating the variable regions of a T-cell receptor (TCR) alpha or beta chain, said method comprising: (a) isolating a single T cell; (b) performing whole genome amplification to amplify the genomic DNA of the T cell; (c) incubating the amplified genomic DNA with a set of outer primers in a genomic TCR alpha enrichment amplification reaction or genomic TCR beta enrichment amplification reaction to produce an enrichment product, wherein the set of primers comprises at least one outer primer substantially complementary to each V and J region of the TCR alpha chain or TCR beta chain; and (d) incubating the enrichment product with a set of inner primers in an TCR alpha isolation amplification reaction or TCR beta isolation amplification reaction to produce an isolation product, wherein the set of inner primers comprises at least one inner primer complementary to each of the V and J regions of the TCR alpha chain or TCR beta chain.

16. The method of claim 15 comprising a step of (e) incubating the isolation product with a set of cloning primers in a cloning amplification reaction to produce a cloning product, wherein the set of cloning primers comprises at least one cloning primer complementary to each of the V and J regions of the TCR alpha chain or TCR beta chain.

17. The method of claim 16 comprising a step of (f) incubating the cloning product with a set of homologous primers in a homologous amplification reaction.

* * * * *